US007585847B2

(12) United States Patent
Bratzler et al.

(10) Patent No.: US 7,585,847 B2
(45) Date of Patent: Sep. 8, 2009

(54) IMMUNOSTIMULATORY NUCLEIC ACIDS FOR THE TREATMENT OF ASTHMA AND ALLERGY

(75) Inventors: Robert L. Bratzler, Concord, MA (US); Deanna M. Petersen, Newton, MA (US); Yves Fouron, Marlboro, MA (US)

(73) Assignee: Coley Pharmaceutical Group, Inc., New York, NY (US)

( * ) Notice: Subject to any disclaimer, the term of this patent is extended or adjusted under 35 U.S.C. 154(b) by 309 days.

(21) Appl. No.: 09/776,479

(22) Filed: Feb. 2, 2001

(65) Prior Publication Data
US 2004/0067902 A9   Apr. 8, 2004

Related U.S. Application Data

(60) Provisional application No. 60/179,991, filed on Feb. 3, 2000.

(51) Int. Cl.
*A61K 39/38* (2006.01)
*A61K 39/395* (2006.01)
*A61K 45/00* (2006.01)
*A61K 38/00* (2006.01)
*A61K 38/16* (2006.01)
*A61K 31/70* (2006.01)
*A01N 37/18* (2006.01)
*A01N 43/04* (2006.01)
*C07H 19/00* (2006.01)
*C07H 21/00* (2006.01)
*C07H 21/04* (2006.01)

(52) U.S. Cl. .............. 514/44; 514/2; 514/12; 514/8; 424/184.1; 424/130.1; 424/278.1; 424/279.1; 536/24.5; 536/22.1

(58) Field of Classification Search ............ 514/44; 536/23.1, 23.5, 24.5; 424/275.1
See application file for complete search history.

(56) References Cited

U.S. PATENT DOCUMENTS

| | | | |
|---|---|---|---|
| 3,906,092 A | 9/1975 | Hilleman et al. | |
| 5,023,243 A | 6/1991 | Tullis | |
| 5,093,318 A | 3/1992 | Goodman et al. | |
| 5,112,605 A | 5/1992 | Jardieu | |
| 5,248,670 A | 9/1993 | Draper et al. | |
| 5,498,410 A | 3/1996 | Gleich | |
| 5,585,479 A | 12/1996 | Hoke et al. | |
| 5,663,153 A | 9/1997 | Hutcherson et al. | |
| 5,679,647 A | 10/1997 | Carson et al. | |
| 5,681,555 A | 10/1997 | Gleich | |
| 5,723,335 A | 3/1998 | Hutcherson et al. | |
| 5,726,160 A | 3/1998 | McMichael | |
| 5,786,189 A | 7/1998 | Locht et al. | |
| 5,804,566 A | 9/1998 | Carson et al. | |
| 5,849,719 A | 12/1998 | Carson et al. | |
| 5,908,620 A | 6/1999 | Tu et al. | |
| 5,922,766 A | 7/1999 | Acosta et al. | |
| 5,932,556 A | 8/1999 | Tam | |
| 5,955,059 A | 9/1999 | Gilchrest et al. | |
| 5,955,442 A | 9/1999 | McMichael | |
| 5,958,378 A | 9/1999 | Waldrep et al. | |
| 5,994,315 A | 11/1999 | Nyce et al. | |
| 6,013,639 A | 1/2000 | Peyman et al. | |
| 6,025,339 A | 2/2000 | Nyce et al. | |
| 6,040,296 A | 3/2000 | Nyce et al. | |
| 6,086,898 A | 7/2000 | DeKruyff et al. | |
| 6,090,791 A | 7/2000 | Sato et al. | |
| 6,096,721 A | 8/2000 | McMichael | |
| 6,100,244 A | 8/2000 | McMichael | |
| 6,174,872 B1 | 1/2001 | Carson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,221,882 B1 | 4/2001 | Macfarlane | |
| 6,239,116 B1 | 5/2001 | Krieg et al. | |
| 6,339,068 B1 * | 1/2002 | Krieg et al. ............ 514/44 |
| 6,399,630 B1 | 6/2002 | Macfarlane | |
| 6,406,705 B1 * | 6/2002 | Davis et al. ......... 424/278.1 |
| 6,426,336 B1 * | 7/2002 | Carson et al. ........... 514/44 |
| 6,429,199 B1 * | 8/2002 | Krieg et al. ............ 514/44 |
| 6,479,504 B1 | 11/2002 | Macfarlane et al. | |
| 6,498,148 B1 * | 12/2002 | Raz ................... 514/44 |
| 6,514,948 B1 * | 2/2003 | Raz et al. .............. 514/44 |
| 6,521,637 B2 | 2/2003 | Macfarlane | |
| 6,552,006 B2 | 4/2003 | Raz et al. | |
| 6,558,670 B1 | 5/2003 | Friede et al. | |
| 6,562,798 B1 | 5/2003 | Schwartz | |
| 6,589,940 B1 | 7/2003 | Raz et al. | |
| 6,610,308 B1 | 8/2003 | Haensler et al. | |
| 6,610,661 B1 | 8/2003 | Carson et al. | |
| 6,635,624 B1 | 10/2003 | Davis et al. | |
| 6,653,292 B1 | 11/2003 | Krieg et al. | |
| 6,727,230 B1 | 4/2004 | Hutcherson et al. | |
| 6,787,524 B2 | 9/2004 | Chang et al. | |
| 6,821,957 B2 | 11/2004 | Krieg et al. | |
| 6,943,240 B2 | 9/2005 | Bauer et al. | |

(Continued)

FOREIGN PATENT DOCUMENTS

EP          0 302 758 B1    2/1989

(Continued)

OTHER PUBLICATIONS

Kline et al, Am. J. Physiol. Lung Cell Mol. Physiol., 2002, 283:L170-L179.*

(Continued)

*Primary Examiner*—N. M Minnifield
(74) *Attorney, Agent, or Firm*—Wolf, Greenfield & Sacks, P.C.; Gregg C. Benson

(57) ABSTRACT

The invention involves administration of an immunostimulatory nucleic acid alone or in combination with an asthma/allergy medicament for the treatment or prevention of asthma and allergy in subjects. The combination of drugs are administered in synergistic amounts or in various dosages or at various time schedules. The invention also relates to kits and compositions concerning the combination of drugs.

21 Claims, No Drawings

U.S. PATENT DOCUMENTS

| | | |
|---|---|---|
| 6,949,520 B1 | 9/2005 | Hartmann et al. |
| 6,951,845 B2 | 10/2005 | Carson et al. |
| 6,977,245 B2 | 12/2005 | Klinman et al. |
| 6,994,870 B2 | 2/2006 | Tsai |
| 7,001,890 B1 | 2/2006 | Wagner et al. |
| 7,034,007 B1 | 4/2006 | Nyce et al. |
| 7,208,478 B2 | 4/2007 | Carson et al. |
| 7,223,398 B1 | 5/2007 | Tuck et al. |
| 7,223,741 B2 | 5/2007 | Krieg |
| 7,271,156 B2 * | 9/2007 | Krieg et al. ............ 514/44 |
| 7,306,782 B2 | 12/2007 | Borel et al. |
| 7,354,711 B2 | 4/2008 | Macfarlane |
| 7,402,572 B2 | 7/2008 | Krieg et al. |
| 7,410,975 B2 | 8/2008 | Lipford et al. |
| 2001/0044416 A1 * | 11/2001 | McCluskie et al. ........ 514/44 |
| 2002/0086295 A1 | 7/2002 | Raz et al. |
| 2002/0091097 A1 | 7/2002 | Bratzler et al. |
| 2002/0102255 A1 | 8/2002 | Chang |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 * | 2/2003 | Krieg ............ 424/93.2 |
| 2003/0026801 A1 | 2/2003 | Weiner et al. |
| 2003/0027782 A1 | 2/2003 | Carson et al. |
| 2003/0049266 A1 | 3/2003 | Fearon et al. |
| 2003/0050261 A1 * | 3/2003 | Krieg et al. ............ 514/44 |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0064064 A1 | 4/2003 | Dina et al. |
| 2003/0078223 A1 * | 4/2003 | Raz et al. ............ 514/44 |
| 2003/0091599 A1 * | 5/2003 | Davis et al. ........ 424/278.1 |
| 2003/0092663 A1 * | 5/2003 | Raz ............ 514/44 |
| 2003/0100527 A1 | 5/2003 | Krieg et al. |
| 2003/0119773 A1 | 6/2003 | Raz et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0186921 A1 | 10/2003 | Carson et al. |
| 2003/0191079 A1 | 10/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0006034 A1 | 1/2004 | Raz et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0053880 A1 | 3/2004 | Krieg |
| 2004/0064064 A1 | 4/2004 | Zhou et al. |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 * | 11/2004 | Davis et al. ............ 514/44 |
| 2004/0235774 A1 * | 11/2004 | Bratzler et al. ........... 514/44 |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0248837 A1 | 12/2004 | Raz et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0042203 A1 | 2/2005 | Davis et al. |
| 2005/0043529 A1 | 2/2005 | Davis et al. |
| 2005/0049213 A1 * | 3/2005 | Agrawal ............ 514/44 |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0064401 A1 | 3/2005 | Olek et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0209183 A1 | 9/2005 | Kippenberger et al. |
| 2005/0209184 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 * | 7/2006 | Bratzler et al. ........... 514/44 |
| 2006/0171968 A1 | 8/2006 | Brimnes et al. |
| 2006/0172966 A1 | 8/2006 | Lipford et al. |

| | | | |
|---|---|---|---|
| 2006/0188913 A1* | 8/2006 | Krieg et al. ............... 435/6 |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1* | 2/2007 | Bratzler et al. ............ 514/44 |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2007/0243209 A1 | 10/2007 | Segal et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |

FOREIGN PATENT DOCUMENTS

| | | |
|---|---|---|
| EP | 0 468 520 A2 | 1/1992 |
| EP | 1 671 646 A2 | 6/2006 |
| WO | WO 91/12811 A1 | 9/1991 |
| WO | WO 92/03456 A1 | 3/1992 |
| WO | WO 92/18522 A1 | 10/1992 |
| WO | WO 92/21353 A1 | 12/1992 |
| WO | WO 94/19945 A1 | 9/1994 |
| WO | WO 95/05853 A1 | 3/1995 |
| WO | WO 95/26204 A1 | 10/1995 |
| WO | WO 96/02555 A1 | 2/1996 |
| WO | WO 96/24380 A1 | 8/1996 |
| WO | WO 96/32138 A1 | 10/1996 |
| WO | WO 96/35782 A1 | 11/1996 |
| WO | WO 96/40162 A1 | 12/1996 |
| WO | WO 97/28259 A1 | 8/1997 |
| WO | WO 98/14210 A1 | 4/1998 |
| WO | WO 98/16247 A1 | 4/1998 |
| WO | WO 98/18810 A1 | 5/1998 |
| WO | WO 98/29430 A1 | 7/1998 |
| WO | WO 98/37919 A1 | 9/1998 |
| WO | WO 98/40100 A1 | 9/1998 |
| WO | WO 98/49288 A1 | 11/1998 |
| WO | WO 98/52581 A1 | 11/1998 |
| WO | WO 98/55495 A2 | 12/1998 |
| WO | WO 98/55609 A1 | 12/1998 |
| WO | WO 99/11275 A2 | 3/1999 |
| WO | WO 99/51259 A2 | 10/1999 |
| WO | WO 99/52549 A1 | 10/1999 |
| WO | WO 99/56755 A1 | 11/1999 |
| WO | WO 99/58118 A2 | 11/1999 |
| WO | WO 99/62923 A2 | 12/1999 |
| WO | WO 00/06588 A1 | 2/2000 |
| WO | WO 00/14217 A2 | 3/2000 |
| WO | WO 00/14217 A3 | 3/2000 |
| WO | WO 00/15256 A2 | 3/2000 |
| WO | WO 00/16804 A1 | 3/2000 |
| WO | WO 00/20039 A1 | 4/2000 |
| WO | WO 00/54803 A2 | 9/2000 |
| WO | WO 00/61151 A2 | 10/2000 |
| WO | WO 00/62787 A1 | 10/2000 |
| WO | WO 00/67023 A1 | 11/2000 |
| WO | WO 01/02007 A1 | 1/2001 |
| WO | WO 01/12223 A2 | 2/2001 |
| WO | WO 01/22972 A2 | 4/2001 |
| WO | WO 01/22990 A2 | 4/2001 |
| WO | WO 01/35991 A2 | 5/2001 |
| WO | WO 01/45750 A1 | 6/2001 |
| WO | WO 02/28428 A2 | 4/2002 |
| WO | WO 03/043572 A2 | 5/2003 |
| WO | WO 2004/007743 A2 | 1/2004 |
| WO | WO 2004/026888 A2 | 4/2004 |
| WO | WO 2004/041183 A2 | 5/2004 |
| WO | WO 2004/094671 A2 | 11/2004 |
| WO | WO 2006/080946 A2 | 8/2006 |
| WO | WO 2006/096497 A2 | 9/2006 |
| WO | WO 2007/031877 A2 | 3/2007 |
| WO | WO 2007/038720 A2 | 4/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Aderem et al, Cell, 2000, 103:993-996.*
Spiegelberg et al, Current Opinion in Mol. Therapeutics, 2002, 4/1:64-71.*
Ikeda et al, In: Microbial DNA and Host Immunity, Editor, E. Raz, 2002, pp. 289-299.*
Horner et al, In: Microbial DNA and Host Immunity, Editor E. Raz, 2002, pp. 279-287.*
Kitagaki et al, In: Microbial DNA and Host Immunity, Editor E. Raz, 2002, pp. 301-314.*
Klinman et al, Drug News Perspect., Jun. 2000, 13/5:289-296.*
Broide et al, In: Immunostimulatory DNA Sequences, Editor E. Raz, 2001, pp. 117-124.*
Leonard et al, Biodrugs, 2003, 17/1:1-7.*
Tighe et al, J. Allergy Clin. Immunol., 2000, 106:124-134.*
Broide et al, J. Immunol., 1998, 161:7054-7062.*
Kohama et al, J. Allergy Clin. Immunol., 1999, 104/6:1231-1238.*
Hartmann et al, PNAS, USA, 1999, 96:9305-9310.*
Marshall et al, J. Allergy Clin. Immunol., 2001, 108:191-197.*
Tournoy et al, Clin. Exp. All., 2002, 31:17-29.*
Heeg et al, Int. Arch. Allergy Immunol., 2000, 121:87-97.*
Broide et al, Springer Semin. Immunopathol, 2000, 22:117-124.*
Peng et al, International Immunol., 2001, 13/1:3-11.*
Horner et al, J. Allergy Clin. Immunol., 2002, 110:413-420.*
Horner et al, J. Allergy Clin. Immunol., 2002, 110:706-712.*
Uhlmann et al, Current Opinion in Drug Discovery and Development, 2003, 6/2:204-217.*
Kandimalla et al, Current Opinion in Molecular Therapeutics, 2002, 4/2:122-129.*
Barnes, European J. Internal Medicine, 2000, 11/1:9-20 Abstract only.*
Sur et al, J. Immunology, 1999, 162:6284-6293.*
Park et al, J. Allergy Clin. Immunol., 2001, 108:570-576.*
Hansbro et al, Pharmacology and Therapeutics, 2004, 101:193-210.*
Bochner et al, J. Allergy Clin. Immunol., 2004, 113:868-875.*
Sampson, J. Allergy Clin. Immunol., 2004, 113:805-819.*
Mutwiri et al, J. Controlled Release, 2004, 97:1-17.*
Pink et al, Vaccine, 2004, 22:2097-2102.*
Farkas et al, J. Allergy Clin. Immunol., 2004, 114:436-443.*
Dalpke et al, International J. Medical Microbiology, 2004, 294:345-354.*
Krieg, Current Opinion in Immunology, 2000, 12:35-43.*
Agrawal et al, International Immunopharmacology, 2004, 4:127-138.*
Campbell et al, Clinical Immunology, 2000, 97/3:193-202.*
Herz et al, Current Opinion in Immunology, 2000, 12:632-640.*
Mutwiri et al, Vet. Immunology and Immunopathology, 2003, 91:89-103.*
Erb et al, Current Opinion in Immunology, 2002, 14:633-643.*
Weeratna et al, Vaccine, 2000, 18:1755-1762.*

Smit et al, European J. Pharmacology, 2003, 470:193-199.*
Fozard et al, Current Opinion in Pharmacology, 2003, 3:209-211.*
Casale, J. Allergy Clin. Immunol., 2004, 113:1036-1039.*
Broide et al, J. Immunology, 1998, 161:7054-7062.*
Kline et al, J. Immunology, 1998, 160:2555-2559.*
Norman, J. Allergy Clin. Immunology, 2004, 113:1013-1023.*
Metzger et al, J. Allergy Clin. Immunology, 1999, 104/2 Pt. 1:260-266 Abstract only.*
Kline, Current Opinion Allergy CLin. Immunology, Feb. 2002, 2/1:69-73.*
Dziadzio et al, Handbook Experimental Pharmacology, 2004, 161(Pharmacology and Therapeutics of Asthma and COPD):273-285, Abstract only.*
Silverman et al, Am. J. Respir. Cell Mol. Biol., 2003, 28:645-647.*
Jain et al, Clin. Exp. Allergy, 2003, 33:1330-1335.*
McCluskie et al, Molecular Med., 1999, 5/5:287-300.*
Wohllenben et al, Trends in Immunology, 2001, 22/11:618-626.*
Krieg et al, Immunology Today, 2000, 21/10:521-526.*
Kline et al, Am. J. Physiol. Lung Cell Mol. Physiol., 2002, 283:L1790-L179.*
Weiner, J. Leucocyte Biology, 2000, 68:456-463.*
Agrawal et al, Molecular Med. Today, 2000, 6:72-81.*
Satoh et al, Fukushima Igaku Zasshi, 2002, 52/3:237-250, Abstract only.*
Kuipers et al, Vaccine, 2005, 23:4577-4588.*
Leath et al, Drug Discover Today, Dec. 2005, 10(23/24):1647-1655.*
Cooper et al, Vaccine, 2004, 22:3136-3143.*
Halperin et al, Vaccine, 2003, 21:2461-2467.*
Speiser et al, J. Clinical Investigation, Mar. 2005, 115/3:739-746.*
Seigrist et al, Vaccine, 2004, 23:615-622.*
Simons et al, J. Allergy Clin. Immunol., 2004, 113:1144-1151.*
Socrates et al, Immunol. Allergy Clin. N. Am., 2004, 24:569-581.*
Cooper et al, J. Clinical Immunology, Nov. 2004, 24/6:693-701.*
Krieg et al, J. Immunotherapy, 2004, 27:460-471.*
Haczku, Pharmacology and Therapeutics, 2006, 110:14-34.*
Corry et al, J. Allergy Clin. Immunol., 2006, 117:S461-S464.*
Schaub et al, J. Allergy Clin. Immunol., 2006, 117:969-977.*
Hoffjan et al, Drug Discovery Today: Therapeutic Strategies, 2006, 3/3:317-324.*
Reinero et al, Vet. Immunol. and Immunopathol., 2006, 110:141-153.*
Hayashi et al, American J. Medicine, Oct. 2006, 119/10:896.e1-897.e6.*
Larche et al, Current Opinion in Immunology, 2006, 18:745-750.*
Heijink et al, Pharmacology and Therapeutics, 2006, 112:489-500.*
Higaki et al, J. Allergy Clin. Immunol., Feb. 2006, p. S156, Abstract #607.*
Uhlmann, Exp. Opin. Biol. Ther., 2001, 1/2:319-328.*
Hirose et al, Int. Arch. Allergy and Immunology, 2008, 147:6-16.*
Press Release, Jun. 2006, "Cytos Biotechnology updates on development of allergy vaccine".
Chisholm et al., Airway peptidoglycan and immunostimulatory DNA exposures have divergent effects on the development of airway allergen hypersensitivities J Allergy Clin Immunol. Mar. 2004;113(3):448-54.
Cho et al., Immunostimulatory DNA inhibits transforming growth factor-beta expression and airway remodeling. Am J Respir Cell Mol Biol. May 2004;30(5):651-61. Epub Nov. 14, 2003.
Creticos et al., New approaches in immunotherapy: allergen vaccination with immunostimulatory DNA. Immunol Allergy Clin North Am. Nov. 2004;24(4):569-81.
Fanucchi et al., Immunostimulatory oligonucleotides attenuate airways remodeling in allergic monkeys. Am J Respir Crit Care Med. Dec. 1, 2004;170(11):1153-7. Epub Aug. 11, 2004.
Hessel et al., Immunostimulatory oligonucleotides block allergic airway inflammation by inhibiting Th2 cell activation and IgE-mediated cytokine induction. J Exp Med. Dec. 5, 2005;202(11):1563-73.
Hussain et al. Modulation of murine allergic rhinosinusitis by CpG oligodeoxynucleotides. Laryngoscope. Oct. 2002;112(10):1819-26.
Kips et al., Interleukin-12 inhibits antigen-induced airway hyperresponsiveness in mice. Am J Respir Crit Care Med. Feb. 1996;153(2):535-9.

Kline et al. Eat dirt: CpG DNA and immunomodulation of asthma. Proc Am Thorac Soc. Jul. 2007;4(3):283-8. Review.
Kussebi et al., Advances in immunological treatment of allergy. Curr Med Chem. 2003;2:297-308.
Lee et al., Immunostimulatory DNA inhibits allergen-induced peribronchial angiogenesis in mice. J Allergy Clin Immunol. Mar. 2006;117(3):597-603. Epub Jan. 27, 2006.
Lewis et al., Allergy immunotherapy and inhibition of Th2 immune responses: a sufficient strategy? Curr Opin Immunol. Oct. 2002;14(5):644-51.
Liu et al., CpG directly induces T-bet expression and inhibits IgG1 and IgE switching in B cells. Nat Immunol. Jul. 2003;4(7):687-93. Epub May 25, 2003.
Racila et al., Perspectives in asthma: molecular use of microbial products in asthma prevention and treatment. J. Allergy Clin Immunol. Dec. 2005;116(6):1202-5.
Rhee et al., Allergen-independent immunostimulatory sequence oligodeoxynucleotide therapy attenuates experimental allergic rhinitis. Immunology. Sep. 2004;113(1):106-13.
Roy et al., Bacterial DNA in house and farm barn dust. J Allergy Clin Immunol. Sep. 2003;112(3):571-8.
Sandrasagra et al., Discovery and development of respirable antisense therapeutics for asthma. Antisense Nucleic Acid Drug Dev. Jun. 2002;12(3):177-81. Review.
Santeliz et al., Amb a 1-linked CpG oligodeoxynucleotides reverse established airway hyperresponsiveness in a murine model of asthma. J Allergy Clin Immunol. Mar. 2002;109(3):455-62.
Strieter, What differentiates normal lung repair and fibrosis? Inflammation, resolution of repair, and fibrosis. Proc Am Thorac Soc. Apr. 15, 2008;5(3):305-10.
Vollmer, TLR9 in health and disease. Int Rev Immunol. May-Aug. 2006;25(3-4):155-81.
Youn et al., Immunostimulatory DNA reverses established allergen-induced airway remodeling. J Immunol. Dec. 15, 2004;173(12):7556-64.
Zhu et al., Modulation of ovalbumin-induced Th2 responses by second-generation immunomodulatory oligonucleotides in mice. Int Immunopharmacol. Jul. 2004;4(7):851-62.
Iliev et al., Immunostimulatory oligodeoxynucleotide containing TTTCGTTT motif from Lactobacillus rhamnosus GG DNA potentially suppresses OVA-specific IgE production in mice. Scand J Immunol. Apr. 2008;67(4):370-6. Epub Feb. 1, 2008.
Klinman et al., Synthetic oligonucleotides as modulators of inflammation. J Leukoc Biol. Oct. 2008;84(4):1-7. Epub Apr. 22, 2008.
[No Author Listed] National Institute of Health, Publication No. 97-4051, Jul. 1997.
[No Author Listed] CpG oligonucleotide adjuvants modulate allergic response in mouse model. Allergy Medicine, NewsRx.com. Jan. 16, 2000. (Jahnschmid).
[No Author Listed] Compound decreases need for steroids and reduces asthma symptoms. Allergy Medicine, NewsRx.com. Jan. 16, 2000. (Milgrom).
Aderem et al., How do you see CG? Cell. Dec. 22, 2000;103(7):993-6.
Agrawal et al., Chapter 19: Pharmacokinetics and bioavailability of antisense oligonucleotides following oral and colorectal administrations in experimental animals. 1998:525-43.
Agrawal et al., Antisense therapeutics: is it as simple as complementary base recognition? Mol Med Today. Feb. 2000;6(2):72-81.
Agrawal et al., Novel immunomodulatory oligonucleotides prevent development of allergic airway inflammation and airwway hyperresponsiveness in asthma. Int Immunopharmacol. Jan. 2004;4(1):127-38.
Anitescu et al., Interleukin-10 functions in vitro and in vivo to inhibit bacterial DNA-induced secretion of interleukin-12. J Interferon Cytokine Res. Dec. 1997;17(12):781-8.
Askenase et al., Gee whiz: CpG DNA allergy therapy! J Allergy Clin Immunol. Jul. 2000;106(1 Pt 1):37-40.
Barnes et al., New treatments for asthma. European J Internal Medicine. 2000;11:9-20. Abstract Only.
Bauer et al., DNA activates human immune cells through a CpG sequence-dependent manner. Immunology. Aug. 1999;97(4):699-705.

Bohle et al., Oligodeoxynucleotides containing CpG motifs induce IL-12, IL-18 and IFN-gamma production in cells from allergic individuals and inhibit IgE synthesis in vitro. Eur J Immunol. Jul. 1999;29(7):2344-53.

Brazolot et al., CpG DNA can induce strong Th1 humoral and cell-mediated immune responses against hepatitis B surface antigen in young mice. Proc Natl Acad Sci U S A. Dec. 22, 1998;95(26):15553-8.

Broide et al., Immunostimulatory DNA sequences inhibit IL-5, eosinophilic inflammation, and airway hyperresponsiveness in mice. J Immunol. Dec. 15, 1998;161(12):7054-62.

Broide et al., Modulation of asthmatic response by immunostimulatory DNA sequences. Springer Semin Immunopathol. 2000;22(1-2):117-24.

Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.

Campbell et al., Allergen immunotherapy: novel approaches in the management of allergic diseases and asthma. Clin Immunol. Dec. 2000;97(3):193-202.

Carson et al., Oligonucleotide adjuvants for T helper 1 (Th1)-specific vaccination. J Exp Med. Nov. 17, 1997;186(10):1621-2.

Cella et al., Plasmacytoid dendritic cells activated by influenza virus and CD40L drive a potent TH1 polarization. Nat Immunol. Oct. 2000;1(4):305-10.

Cella et al., Plasmacytoid monocytes migrate to inflamed lymph nodes and produce large amounts of type I interferon. Nat Med. Aug. 1999;5(8):919-23.

Chace et al., Bacterial DNA-induced NK cell IFN-gamma production is dependent on macrophage secretion of IL-12. Clin Immunol Immunopathol. Aug. 1997;84(2):185-93.

Cooper et al., CPG 7909, an immunostimulatory TLR9 agonist oligodeoxynucleotide, as adjuvant to Engerix-B HBV vaccine in healthy adults: a double-blind phase I/II study. J Clin Immunol. Nov. 2004;24(6):693-701.

Cooper et al., Safety and immunogenicity of CPG 7909 injection as an adjuvant to Fluarix influenza vaccine. Vaccine. Aug. 13, 2004;22(23-24):3136-43.

Creticos et al., Immunotherapy with immunostimulatory oligonucleotides linked to purified ragweed Amb a 1 allergen: effects on antibody production, nasal allergen provocation, and ragweed seasonal rhinitis. J Allergy Clin Immunol. 2002:109(4):741-3.

Davis, Use of CpG DNA for enhancing specific immune responses. Curr Top Microbiol Immunol. 2000;247:171-83.

Davis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.

Durham et al., Immunotherapy and allergic inflammation. Clin Exp Allergy. Jan. 1991;21 Suppl 1:206-10.

Dziadzio et al., Handbook of Experimental Pharmacology, Pharmacology and Therapeutics of Asthma and COPD. 2004;161:273-85.

Fornadley et al., Allergy immunotherapy. Otolaryngol Clin North Am. Feb. 1998;31(1):111-27. Abstract Only.

Gallichan et al., Intranasal immunization with CpG oligodeoxynucleotides as an adjuvant dramatically increases IgA and protection against herpes simplex virus-2 in the gential tract. J Immunol. Mar. 1, 2001;166(5):3451-7.

Gao et al., Bacterial DNA and lipopolysaccharide induce synergistic production of TNF-alpha through a post-transcriptional mechanism. J Immunol. Jun. 1, 2001;166(11):6855-60.

Gouttefangeas et al., Problem solving for tumor immunotherapy. Nat Biotechnol. May 2000;18(5):491-2.

Grossman et al., Avoiding tolerance against prostatic antigens with subdominant peptide epitopes. J Immunother. May-Jun. 2001;24(3):237-41.

Hafner et al., Antimetastatic effect of CpG DNA mediated by type I IFN. Cancer Res. Jul. 15, 2001;61(14):5523-8.

Halperin et al., A phase I study of the safety and immunogenicity of recombinant hepatitis B surface antigen co-administered with an immunostimulatory phosphorothioate oligonucleotide adjuvant. Vaccine. Jun. 2, 2003;21(19-20):2461-7.

Hancock et al., CpG containing oligodeoxynucleotides are potent adjuvants for parenteral vaccination with the fusion (F) protein of respiratory syncytial virus (RSV). Vaccine. Sep. 14, 2001;19(32):4874-82.

Hartmann et al., CpG DNA and LPS induce distinct patterns of activation in human monocytes. Gene Ther. May 1999;6(5):893-903.

Hartmann et al., Mechanism and function of a newly identified CpG DNA motif in human primary B cells. J Immunol. Jan. 15, 2000;164(2):944-53.

Heeg et al., CpG DNA as a Th1 trigger. Int Arch Allergy Immunol. Feb. 2000;121(2):87-97.

Hogg et al., The pathology of asthma. APMIS. Oct. 1997;105(10):735-45.

Hopkin et al., Curbing the CpGs of Bacterial and Viral DNA. BioMedNet. Jun. 25, 1999; Issue 57.

Horner et al., Microbial DNA and Host Immunity. Chapter 22:DNA-based immunotherapeutics for allergic disease. p. 279-287, 2002; Ed.: E. Raz.

Horner et al., Optimized conjugation ratios lead to allergen immunostimulatory oligodeoxynucleotide conjugates with retained immunogenicity and minimal anaphylactogenicity. J Allergy Clin Immunol. Sep. 2002;110(3):413-20.

Horner et al., Immunostimulatory sequence oligodeoxynucleotide-based vaccination and immunomodulation: two unique but complementary strategies for the treatment of allergic diseases. J Allergy Clin Immunol. Nov. 2002;110(5):706-12.

Hussain et al., CpG oligodeoxynucleotides: a novel therapeutic approach for atopic disorders. Curr Drug Targets Inflamm Allergy. Sep. 2003;2(3):199-205.

Hussain et al., DNA, the immune system, and atopic disease. J Investig Dermatol Symp Proc. Jan. 2004;9(1):23-8.

Ikeda et al., Microbial DNA and Host Immunity. Chapter 23: Immunostimulatory DNA for allergic asthma. p. 289, 2002; Ed.: E. Raz pp. 289-299.

Infante-Duarte et al., Th1/Th2 balance in infection. Springer Semin Immunopathol. 1999;21(3):317-38.

Irwin et al., Asthma may be reduced by vaccine from soil. The Daily Telegraph. Sep. 5, 1999;6.

Jain et al., Mucosal immunotherapy with CpG oligodeoxynucleotides reverses a murine model of chronic asthma induced by repeated antigen exposure. Am J Physiol Lung Cell Mol Physiol. Nov. 2003;285(5):L1137-46.

Jain et al., CpG DNA and immunotherapy of allergic airway disease. Clin Exp Allergy. Oct. 2003;33(10):1330-5.

Jain et al., CpG DNA: immunomodulation and remodeling of the asthmatic airway. Expert Opin Biol Ther. Sep. 2004;4(9):1533-40.

Jain et al., CpG-oligodeoxynucleotides inhibit airway remodeling in a murine model of chronic asthma. J Allergy Clin Immunol. Dec. 2002;110(6):867-72.

Jain et al., The promise of CpG DNA in the treatment of asthma. Recent Res Develop Resp Crit Care Med. 2002;2:7-18.

Jakob et al., Activation of cutaneous dendritic cells by CpG-containing oligodeoxynucleotides: a role for dendritic cells in the augmentation of Th1 responses by immunostimulatory DNA. J Immunol. Sep. 15, 1998;161(6):3042-9.

Jakob et al., Bacterial DNA and CpG-containing oligodeoxynucleotides activate cutaneous dendritic cells and induce IL-12 production: implications for the augmentation of Th1 responses. Int Arch Allergy Immunol. Feb.-Apr. 1999;118(2-4):457-61.

Jilek et al., Antigen-independent suppression of the allergic immune response to bee venom phospholipase A(2) by DNA vaccination in CBA/J mice. J Immunol. Mar. 1, 2001;166(5):3612-21.

Kandimalla et al., Towards optimal design of second-generation immunomodulatory oligonucleotides. Curr Opin Mol Ther. Apr. 2002;4(2):122-9.

Kataoka et al., Immunotherapeutic potential in guinea-pig tumor model of deoxyribonucleic acid from Mycobacterium bovis BCG complexed with poly-L-lysine and carboxymethylcellulose. Jpn J Med Sci Biol. Oct. 1990;43(5):171-82.

Kitagaki et al., Immunomodulatory effects of CpG oligodeoxynucleotides on established th2 responses. Clin Diagn Lab Immunol. Nov. 2002;9(6):1260-9.

Kitagaki et al., Oral administration of CpG-ODNs suppresses antigen-induced asthma in mice. Clin Exp Immunol. Feb. 2006;143(2):249-59.

Kitagaki et al., CpG oligonucleotides in asthma Microbial DNA and Host Immunity. Chapter 24. p. 301, 2002; Ed.: E. Raz; pp. 301-314.

Kline et al., Modulation of airway inflammation by CpG oligodeoxynucleotides in a murine model of asthma. J Immunol. Mar 15, 1998;160(6):2555-9.

Kline et al., Induction of oral tolerance by CpG-ODNs in a murine model of asthma. J Allergy Clin Immunol. Feb. 2004;113(2):S254. Abstract 915.

Kline et al., DNA therapy for asthma. Curr Opin Allergy Clin Immunol. Feb. 2002;2(1):69-73.

Kline et al., T-lymphocyte dysregulation in asthma. Proc Soc Exp Biol Med. Dec. 1994;207(3):243-53.

Kline et al., Effects of CpG DNA on Th1/Th2 balance in asthma. Curr Top Microbiol Immunol. 2000;247:211-25.

Kline et al., Treatment of established asthma in a murine model using CpG oligodeoxynucleotides. Am J Physiol Lung Cell Mol Physiol. Jul. 2002;283(1):L170-9.

Klinman et al., CpG motifs as immune adjuvants. Vaccine. Jan. 1999;17(1):19-25.

Klinman et al., Immunotherapeutic applications of CpG-containing oligodeoxynucleotides. Drug News Perspect. Jun. 2000;13(5):289-96.

Kohama et al., Immunostimulatory oligodeoxynucleotide induces TH1 immune response and inhibition of IgE antibody production to cedar pollen allergens in mice. J Allergy Clin Immunol. Dec. 1999;104(6):1231-8.

Kovarik et al., CpG oligodeoxynucleotides can circumvent the Th2 polarization of neonatal responses to vaccines but may fail to fully redirect Th2 responses established by neonatal priming. J Immunol. Feb. 1, 1999;162(3):1611-7.

Krieg et al., Lymphocyte activation mediated by oligodeoxynucleotides or DNA containing novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).

Krieg et al., Lymphocyte activation by CpG dinucleotide motifs in prokaryotic DNA. Trends Microbiol. Feb. 1996;4(2):73-6.

Krieg et al., 1996 Meeting on Molecular Approaches to the Control of Infectious Diseases. Cold Spring Harbor Laboratory, Sep. 9-13, 1996: 116.

Krieg et al., Infection. In McGraw Hill Book. 1996: 242-3.

Krieg et al., Chapter 8: Immune Stimulation by Oligonucleotides. in Antisense Research and Application. Crooke, editor. 1998; 243-62.

Krieg et al., Sequence motifs in adenoviral DNA block immune activation by stimulatory CpG motifs. Proc Natl Acad Sci U S A. Oct. 13, 1998;95(21):12631-6.

Krieg et al., CpG DNA induces sustained IL-12 expression in vivo and resistance to Listeria monocytogenes challenge. J Immunol. Sep. 1, 1998;161(5):2428-34.

Krieg et al., The CpG motif: Implications for clinical immunology. BioDrugs. Nov. 1, 1998;10(5):341-6.

Krieg et al., CpG DNA: a novel immunomodulator. Trends Microbiol. Feb. 1999;7(2):64-5.

Krieg et al., Applications of immune stimulatory CpG DNA for antigen-specific and antigen-nonspecific cancer immunotherapy. Eur J Canc. Oct. 1999; 35/Suppl4:S10. Abstract #14.

Krieg et al., Mechanisms and applications of immune stimulatory CpG oligodeoxynucleotides. Biochim Biophys Acta. Dec. 10, 1999;1489(1):107-16.

Krieg, Signal transduction induced by immunostimulatory CpG DNA. Springer Semin Immunopathol. 2000;22(1-2):97-105.

Krieg et al., Causing a commotion in the blood: immunotherapy progresses from bacteria to bacterial DNA. Immunol Today. Oct. 2000;21(10):521-6.

Krieg et al., Mechanism of action of CpG DNA. Curr Top Microbiol Immunol. 2000;247:1-21.

Krieg, The role of CpG motifs in innate immunity. Curr Opin Immunol. Feb. 2000;12(1):35-43.

Krieg et al., Immune effects and therapeutic applications of CpG motifs in bacterial DNA. Immunopharmacology. Jul. 25, 2000;48(3):303-5.

Krieg et al., Enhancing vaccines with immune stimulatory CpG DNA. Curr Opin Mol Ther. Feb. 2001;3(1):15-24.

Krieg et al., Chapter 7: CpG oligonucleotides as immune adjuvants. Ernst Schering Research Found Workshop 2001; 30:105-18.

Krieg et al., Chapter 17:Immune stimulation by oligonucleotides. in Antisense Drug Tech. 2001;1394:471-515.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Krug et al., Toll-like receptor expression reveals CpG DNA as a unique microbial stimulus for plasmacytoid dendritic cells which synergizes with CD40 ligand to induce high amounts of IL-12. Eur J Immunol. Oct. 2001;31(10):3026-37.

Kuramoto et al., In situ infiltration of natural killer-like cells induced by intradermal injection of the nucleic acid from BCG. Microbiol Immunol. 1989;33(11):929-40.

Kuramoto et al., Induction of T-cell-mediated immunity against MethA fibrosarcoma by intratumoral injections of bacillus Calmette-Guerin nucleic acid fraction. Cancer Immunol Immunother. 1992;34(5):283-8.

Kuramoto et al., Changes of host cell infiltration into Meth A fibrosarcoma tumor during the course of regression induced by injections of a BCG nucleic acid fraction. Int J Immunopharmacol. Jul. 1992;14(5):773-82.

LeClerc et al., The preferential induction of a Th1 immune response by DNA-based immunization is mediated by the immunostimulatory effect of plasmid DNA. Cell Immunol. Aug. 1, 1997;179(2):97-106.

Lee et al., Immuno-stimulatory effects of bacterial-derived plasmids depend on the nature of the antigen in intramuscular DNA inoculations. Immunology. Jul. 1998;94(3):285-9.

Leonard et al., Interleukin-12: potential role in asthma therapy. BioDrugs. 2003;17(1):1-7.

Liu et al., CpG ODN is an effective adjuvant in immunization with tumor antigen. J Invest Med. Sep. 7, 1997;45(7):333A.

Lukacs et al., Interleukin-4-dependent pulmonary eosinophil infiltration in a murine model of asthma. Am J Respir Cell Mol Biol. May 1994;10(5):526-32.

Lukacs et al., C-C chemokine-induced eosinophil chemotaxis during allergic airway inflammation. J Leukoc Biol. Nov. 1996;60(5):573-8.

Marshall et al., Immunostimulatory sequence DNA linked to the Amb a 1 allergen promotes T(H)1 cytokine expression while downregulating T(H)2 cytokine expression in PBMCs from human patients with ragweed allergy. J Allergy Clin Immunol. Aug. 2001;108(2):191-7.

Martin-Orozco et al., Enhancement of antigen-presenting cell surface molecules involved in cognate interactions by immunostimulatory DNA sequences. Int Immunol. Jul. 1999;11(7):1111-8.

McCluskie et al., CpG DNA is a potent enhancer of systemic and mucosal immune responses against hepatitis B surface antigen with intranasal administration to mice. J Immunol. Nov. 1, 1998;161(9):4463-6.

McCluskie et al., Route and method of delivery of DNA vaccine influence immune responses in mice and non-human primates. Mol Med. May 1999;5(5):287-300.

McCluskie et al., CpG DNA as mucosal adjuvant. Vaccine, 18:231-237, 2000.

McCluskie et al., CpG DNA is an effective oral adjuvant to protein antigens in mice. Vaccine. Nov. 22, 2000;19(7-8):950-7.

McCluskie et al., The role of CpG in DNA vaccines. Springer Semin Immunopathol. 2000;22(1-2):125-32.

McCluskie et al., The use of CpG DNA as a mucosal vaccine adjuvant. Curr Opin Investig Drugs. Jan. 2001;2(1):35-9.

Metzger et al., Oligonucleotide therapy of allergic asthma. J Allergy Clin Immunol. Aug. 1999;104(2 Pt 1):260-6.

Mosmann et al., The expanding universe of T-cell subsets: Th1, Th2 and more. Immunol Today. Mar. 1996;17(3):138-46.

Norman et al., Immunotherapy: 1999-2004. J Allergy Clin Immunol. Jun. 2004;113(6):1013-23.

Padrid et al., CTLA4Ig inhibits airway eosinophilia and hyper-responsiveness by regulating the development of Th1/Th2 subsets in a murine model of asthma. Am J Respir Cell Mol Biol. Apr. 1998;18(4):453-62.

Park et al., The enhanced effect of a hexameric deoxyriboguanosine run conjugation to CpG oligodeoxynucleotides on protection against allergic asthma. J Allergy Clin Immunol. Oct. 2001;108(4):570-6.

Payette et al., History of vaccines and positioning of current trends. Curr Drug Targets Infect Disord. Nov. 2001;1(3):241-7.

Peng et al., CpG oligodeoxynucleotide vaccination suppresses IgE induction by may fail to down-regulate ongoing IgE responses in mice. Int Immunol. Jan. 2001;13(1):3-11.

Pisetsky et al., The influence of base sequence on the immunological properties of defined oligonucleotides. Immunopharmacology. Nov. 1998;40(3):199-208.

Pisetsky, The influence of base sequence on the immunostimulatory properties of DNA. Immunol Res. 1999;19(1):35-46.

Polanczyk et al., Immunostimulatory effects of DNA and CpG motifs. Cent Eur J of Immunol. 2000;25(3):160-6.

Rankin et al., CpG motif identification for veterinary and laboratory species demonstrates that sequence recognition is highly conserved. Antisense Nucleic Acid Drug Dev. Oct. 2001;11(5):333-40.

Ray et al., Oral pretreatment of mice with immunostimulatory CpG DNA induces reduced susceptibility to *Listeria monocytogenes*. Experimental Biology 2001. Orlando, Florida, USA. Mar. 31-Apr. 4, 2001. Abstracts, part II. FASEB J. Mar. 8, 2001;15(5):A1007.

Raz et al., Potential role of immunostimulatory DNA sequences (ISS) in genetic immunization and autoimmunity. ACR Poster Session C: Cytokines and Inflammatory Mediators. Oct. 20, 1996; Abstract No. 615.

Robinson et al., Predominant TH2-like bronchoalveolar T-lymphocyte population in atopic asthma. N Engl J Med. Jan. 30, 1992;326(5):298-304.

Roman et al., Gene immunization for allergic disorders. Springer Semin Immunopathol. 1997;19(2):223-32.

Saito et al., Allergen-induced murine upper airway inflammation: local and systemic changes in murine experimental allergic rhinitis. Immunology. Oct. 2001;104(2):226-34.

Satoh et al., Morphological and immunohistochemical characteristics of the heterogeneous prostate-like glands (paraurethral gland) seen in female Brown-Norway rats. Toxicol Pathol. Mar.-Apr. 2001;29(2):237-41.

Schwartz et al., Bacterial DNA or oligonucleotides containing unmethylated CpG motifs can minimize lipopolysaccharide-induced inflammation in the lower respiratory tract through an IL-12-dependent pathway. J Immunol. Jul. 1, 1999;163(1):224-31.

Serebrisky et al., CpG oligodeoxynucleotides can reverse Th2-associated allergic airway responses and alter the B7.1/B7.2 expression in a murine model of asthma. J Immunol. Nov. 15, 2000;165(10):5906-12.

Sester et al., Phosphorothioate backbone modification modulates macrophage activation by CpG DNA. J Immunol. Oct. 15, 2000;165(8):4165-73.

Siegrist et al., Co-administration of CpG oligonucleotides enhances the late affinity maturation process of human anti-hepatitis B vaccine response. Vaccine. Dec. 16, 2004;23(5):615-22.

Simons et al., Selective immune redirection in humans with ragweed allergy by injecting Amb a 1 linked to immunostimulatory DNA. J Allergy Clin Immunol. Jun. 2004;113(6):1144-51.

Sjolander et al., Iscoms containing purified *Quillaja saponins* upregulate both Th1-like and Th2-like immune responses. Cell Immunol. Apr. 10, 1997;177(1):69-76.

Sonehara et al., Hexamer palindromic oligonucleotides with 5'-CG-3' motif(s) induce production of interferon. J Interferon Cytokine Res. Oct. 1996;16(10):799-803.

Sparwasser et al., Bacterial DNA causes septic shock. Nature. Mar. 27, 1997;386(6623):336-7.

Sparwasser et al., Immunostimulatory CpG-oligodeoxynucleotides cause extramedullary murine hemopoiesis. J Immunol. Feb. 15, 1999;162(4):2368-74.

Speiser et al., Rapid and strong human CD8+ T cell responses to vaccination with peptide, IFA, and CpG oligonucleotide 7909. J Clin Invest. Mar. 2005;115(3):739-46.

Spiegelberg et al., DNA-based approaches to the treatment of allergies. Curr Opin Mol Ther. Feb. 2002;4(1):64-71.

Stein et al., Problems in interpretation of data derived from in vitro and in vivo use of antisense oligodeoxynucleotides. Antisense Res Dev. Summer 1994;4(2):67-9.

Stein et al., Non-antisense effects of oligodeoxynucleotides. Antisense Technology. 1997; ch11: 241-64.

Sun et al. Type I interferon-mediated stimulation of T cells by CpG DNA. J Exp Med. Dec. 21, 1998;188(12):2335-42.

Sur et al., Long term prevention of allergic lung inflammation in a mouse model of asthma by CpG oligonucleotides. J Immunol. May 15, 1999;162(10):6284-93.

Tighe et al., Conjugation of immunostimulatory DNA to the short ragweed allergen amb a 1 enhances its immunogenicity and reduces its allergenicity. J Allergy Clin Immunol. Jul. 2000;106(1 Pt 1):124-34.

Tighe et al., Conjugation of protein to immunostimulatory DNA results in a rapid, long-lasting and potent induction of cell-mediated and humoral immunity. Eur J Immunol. Jul. 2000;30(7):1939-47.

Tokunaga, Response of the organism to DNA—With a focus on immunostimulatory DNA. Kansen Ensho Meneki. 2001 Autumn; 31(3): 1-12. Japanese.

Tortora et al., Oral antisense that targets protein kinase A cooperates with taxol and inhibits tumor growth, angiogenesis, and growth factor production. Clin Cancer Res. Jun. 2000;6(6):2506-12.

Tournoy et al., Is Th1 the solution for Th2 in asthma? Clin Exp Allergy. Jan. 2002;32(1):17-29.

Uhlmann et al., Recent advances in the development of immunostimulatory oligonucleotides. Curr Opin Drug Discov Devel. Mar. 2003;6(2):204-17.

Van Ojik et al., Phase I/II study with CpG 7909 as adjuvant to vaccination with MAGE-3 protein in patients with MAGE-3 positive tumors. Ann Oncol. 2003;13:157. Abstract 579O.

Verthelyi et al., Human peripheral blood cells differentially recognize and respond to two distinct CPG motifs. J Immunol. Feb. 15, 2001;166(4):2372-7.

Weeratna et al., Reduction of antigen expression from DNA vaccines by coadministered oligodeoxynucleotides. Antisense Nucleic Acid Drug Dev. Aug. 1998;8(4):351-6.

Weeratna et al., CpG ODN can re-direct the Th bias of established Th2 immune responses in adult and young mice. FEMS Immunol Med Microbiol. Dec. 2001;32(1):65-71.

Weeratna et al., CpG DNA induces stronger immune responses with less toxicity than other adjuvants. Vaccine. Mar. 6, 2000;18(17):1755-62.

Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.

Weiner et al., The immunobiology and clinical potential of immunostimulatory CpG oligodeoxynucleotides. J Leukoc Biol. Oct. 2000;68(4):455-63.

Wohlleben et al., Atopic disorders: a vaccine around the corner! Trends Immunol. Nov. 2001;22(11):618-26.

Zhao et al., Pattern and kinetics of cytokin production following administration of phosphorothioate oligonucleotides in mice. Antisense Nucleic Acid Drug Dev. Oct. 1997;7(5):495-502.

Zimmermann et al., CpG oligodeoxynucleotides trigger protective and curative Th1 responses in lethal murine leishmaniasis. J Immunol. Apr. 15, 1998;160(8):3627-30.

Arkwright, P. et al., "Intradermal administration of a killed *Mycobacterium vaccae* suspension (SRL 172) is associated with improvemtn in atopic dermatitis in children with moderate-to-severe disease", *J. Allergy Clin. Immunol.*, Mar. 2001, pp. 531-534.

Hartmann, G. et al., "CpG DNA: A potent signal for growth, activation, and maturation of human dendritic cells", *Proc. Natl. Acad. Sci.*, Aug. 1999, vol. 96, pp. 9305-9310.

Hartmann, G. et al., "CpG DNA and LPS induce distinct patterns of activation in human monocytes", *Gene Therapy*, 1999, vol. 6, pp. 893-903.

Iho, S. et al., "Oligodeoxynucleotides containing palindrome sequences with internal 5'-CpG-3' act directly on human NK and activated T cells to induce IFN-γ production in vitro", *J Immunol.*, Oct. 1, 1999, vol. 163, No. 7, pp. 3642-3652.

Jakob, T. et al., "Bacterial DNA and CpG-containing oligodeoxynucleotides activate cutaneous dendritic cells and induce IL-12 production: implications for the augmentation of Th 1 Responses", *Int. Arch. Allergy Immunol.*, 1999, vol. 118, pp. 457-461.

Jakob, T. et al., "Activation of cutaneous dendritic cells by CpG-containing oligodeoxynucleotides: a role for dendritic cells in the augmentation of Th1 responses by immunostimulatory DNA", *J Immunol.*, 1998, vol. 161, No. 6, pp. 3042-3049.

Klinman, D. et al., "Contibution of CpG motifs to the immunogenicity of DNA vaccines", *J Immunol.*, 1997, vol. 158, No. 8, pp. 3635-3639.

Klinman, D. et al., "Immune recognition of foreign DNA: a cure for bioterrorism?", *Immunity*, Aug. 1999, vol. 11, pp. 123-129.

Kranzer K. et al., "CpG-oligodeoxynucleotides enhance T-cell receptor-triggered interferon-γ production and up-regulation of CD69 via induction of antigen-presenting cell-derived interferon type I and interleukin-12" *Immunology*, 2000, vol. 99, pp. 170-178.

Krieg, A. et al., "Mechanisms and therapeutic applications of immune stimulatory CpG DNA", *Pharmacology & Therapeutics*, 1999, vol. 84, pp. 113-120.

Arora et al., Immunomodulation by liposome entrapped allergen. Mol Cell Biochem. Sep. 21, 1990;97(2):173-9. Abstract Only.

Cho et al., Immunostimulatory DNA sequences inhibit respiratory syncytial viral load, airway inflammation, and mucus secretion. J Allergy Clin Immunol. Nov. 2001;108(5):697-702.

Doerschug et al., Asthma guidelines: an assessment of physician understanding and practice. Am J Respir Crit Care Med. Jun. 1999;159(6):1735-41.

Fonseca et al., Use of CpG oligonucleotides in treatment of asthma and allergic disease. Adv Drug Deliv Rev. Jan. 9, 2009. [Epub ahead of print]. 7 pages.

Gavett et al., Interleukin 12 inhibits antigen-induced airway hyper-responsiveness, inflammationm, and Th2 cytokine expression in mice. J Exp Med. Nov. 1, 1995;182(5):1527-36.

Kline, Effects of CpG DNA on Th1/Th2 balance in asthma. In Immunobiology of Bacterial CpG-DNA, Ed. H. Wagner. Springer. 2000;247:211-25..

Kline et al., Ch. 26: DNA Immunomodulation of asthma. In Inflammatory Mechanisms in Allergic Diseases. Ed., Zeiman et al. Marcel Dekker, Inc. 2002;551-64.

Kline, Immunotherapy of asthma using CpG oligodeoxynucleotides. Immunol Res. 2007;39(1-3):279-86. Review.

Kline et al., Toll-like receptor 9 activation with CpG oligodeoxynucleotides for asthma therapy. Drug News Perspect. Oct. 2008;21(8):434-9.

Kou et al., [Analysis and regulation of interferon-gamma production by peripheral blood lymphocytes from patients with bronchial asthma] Arerugi. Mar. 1994;43(3):482-91. Japanese. Abstract Only.

Krieg et al., CpG motifs in bacterial DNA and their immune effects. Annu Rev Immunol. 2002;20:709-60.

Krieg et al., P-chirality-dependent immune activation by phosphorothioate CpG oligodeoxynucleotides. Oligonucleotides. 2003;13(6):491-9.

Krieg et al., Unmethylated CpG DNA protects mice from lethal listeria monocytogenes challenge. Vaccines. 1997;97:77-9.

Krieg, Antiinfective applications of toll-like receptor 9 agonists. Proc Am Thorac Soc. Jul. 2007;4(3):289-94.

Krieg, Development of TLR9 agonists for cancer therapy. J Clin Invest. May 2007;117(5):1184-94.

Krieg, Direct immunologic activities of CpG DNA and implications for gene therapy. J Gene Med. Jan.-Feb. 1999;1(1):56-63.

Krieg, How to exclude immunostimulatory and other nonantisense effects of antisense oligonucleotides. Manual of Antisense. 1999:79-89.

Krieg, Immune effects and mechanisms of action of CpG motifs. Vaccine. Nov. 8, 2001;19(6):618-22.

Krieg, Now I know my CpGs. Trends Microbiol. Jun. 2001;9(6):249-52.

Krieg, Therapeutic potential of Toll-like receptor 9 activation. Nat Rev Drug Discov. Jun. 2006;5(6):471-84.

Krieg, Toll-like receptor 9 (TLR9) agonists in the treatment of cancer. Oncogene. Jan. 7, 2008;27(2):161-7. Review.

Milgrom et al., Treatment of allergic asthma with monoclonal anti-IgE antibody. rhuMAb-E25 Study Group. N Engl J Med. Dec. 23, 1999;341(26):1966-73. Abstract only.

Sjölander et al., Iscoms containing purified *Quillaja saponins* upregulate both Th1-like and Th2-like immune responses. Cell Immunol. Apr. 10, 1997;177(1):69-76.

Guidelines for the Diagnosis and Management of Asthma, "Pharmacology Therapy: The Medications", *NIH Publication* No. 97-4051, 1997, pp. 59-79.

"Vaccine adjuvants in medicine and the role of SRL172", SR Parama Company Profile 3 Pages, Dec. 10, 1999, srpharma.com/comp_prof.html.

Adya, N. et al., "Expansion of CREB's DNA recognition specificity by Tax results from interaction with Ala-Ala-Arg at positions 282-284 near the conserved DNA-binding domain of CREB", *Proc. Natl. Acad. Sci USA*. Jun. 1994. pp. 5642-5646. vol. 91.

Agrawal, S., "Antisense oligonucleotides: towards clinical trials", *TIBTECH*, Oct. 1996, pp. 376-387. vol. 14. Reprints from Elsevier Trends Journals U.K.

Anderson, G.P. et al., "$T_H2$ and '$T_H2$-like' cells in allergy and asthma: pharmacological perspectives", *TIPS*. Sep. 1994, pp. 324-332, vol. 15.

Angier, N., "Microbe DNA Seen as Alien By Immune Cells", *New York Times Science*, Apr. 11, 1995, pp. B5 and B9.

Azad, R.F. et al., "Antiviral Activity of a Phosphorothioate Oligonucleotide Complementary to RNA of the Human Cytomegalovirus Major Immediate-Early Region", *Antimicrobial Agents and Chemotherapy*, Sep. 1993, pp. 1945-1954, vol. 37, No. 9, American Society of Microbiology.

Azuma, I., "Biochemical and Immunological Studies on Cellular Components of *Tubercle bacilli*", *Kekkaku*, 1992, pp. 625-635, vol. 67, No. 9.

Ballas, Z.K. et al., "Induction of NK Activity in Murine and Human Cells by CpG Motifs in Oligodeoxynucleotides and Bacterial DNA", *The Journal of Immunology*, 1996, pp. 1840-1845, vol. 157, No. 5, The American Association of Immunologists.

Bates, P.J. et al., "Antiproliferative Activity of G-rich Oligonucleotides Correlates with Protein Binding", *The Journal of Biological Chemistry*, Sep. 10, 1999, pp. 26369-26377, vol. 274, No. 37, The American Society for Biochemistry and Molecular Biology, Inc. USA.

Bayever, E. et al., "Systemic Administration of a Phosphorothioate Oligonucleotide with a Sequence Complementary to p53 for Acute Myelogenous Leukemia and Myelodysplastic Syndrome: Initial Results of a Phase 1 Trial", *Antisense Research and Development*, 1993, pp. 383-390, vol. 3, Mary Ann Liebert, Inc.

Benimetskaya, L. et al., "Formation of a G-tetrad and higher order structures correlates with biological activity of a RelA (NF-kB p65) 'antisense' oligonucleotide", *Nucleic Acids Research*, 1997, pp. 2648-2656, vol. 25, No. 13, Oxford University Press.

Bennett, R.M. et al., "DNA Binding to Human Leukocytes—Evidence for a Receptor-mediated Association, Internalization, and Degradation of DNA", *J. Clin. Invest.*, Dec. 1985. pp. 2182-2190. vol. 76, The American Society for Clinical Investigation, Inc.

Berg, D.J. et al., "Interleukin-10 is a Central Regulator of the Response to LPS in Murine Models of Endotoxic Shock and the Shwartzman Reaction but not Endotoxin Tolerance", *J. Clin. Invest.*, Nov. 1995, pp. 2339-2347, vol. 96, The American Society for Clinical Investigation, Inc.

Bishop, J.S. et al., "Intramolecular G-quartet Motifs Confer Nuclease Resistance to a Potent Anti-HIV Oligonucleotide", *The Journal of Biological Chemistry*, Mar. 8, 1996, pp. 5698-5703. vol. 271, No. 10, The American Society for Biochemistry and Molecular Biology, Inc. USA.

Blanchard, D.K. et al., "Interferon-γ Induction by Lipopolysaccharide: Dependence on Interleukin 2 and Macrophages", *The Journal of Immunology*, Feb. 1, 1986, pp. 963-970. vol. 136, No. 3, The American Association of Immunologists USA.

Blaxter, M.L. et al., "Genes expressed in *Brugia malayi* infective third stage larvae", *Molecular and Biochemical Parasitology*, 1996, pp. 77-93, vol. 77, Elsevier Science B.V.

Boggs, R.T. et al., "Characterization and Modulation of Immune Stimulation by Modified Oligonucleotides", *Antisense & Nucleic Acid Drug Development*, 1997, pp. 461-471, vol. 7, Mary Ann Liebert, Inc.

Branda, R.F. et al., "Immune Stimulation by an Antisense Oligomer Complementary to the *rev* Gene of HIV-1", *Biochemical Pharmacology*, 1993, pp. 2037-2043, vol. 45, No. 10, Pergamon Press Ltd.

Branda, R.F. et al., "Amplification of antibody production by phosphorothioate oligodeoxynucleotides", *J. Lab. Clin. Med.*, Sep. 1996, pp. 329-338, vol. 128, No. 3, Mosyb-Year Book, Inc.

Briskin, M. et al., "Lipopolysaccharide-Unresponsive Mutant Pre-B-Cell Lines Blocked in NF-κB Activation", *Molecular and Cellular Biology*, Jan. 1990, pp. 422-425, vol. 10. No. 1, American Society of Microbiology.

Broide, D. et al., "DNA-Based Immunization for Asthma", *Int. Arch. Allergy Immunol.*, 1999, pp. 453-456, vol. 118, S. Karger AG, Basel.

Burgess, T.L. et al., "The antiproliferation activity of c-myb and c-myc antisense oligonucleotides in smooth muscle cells in caused by a nonantisense mechanism", *Proc. Natl. Acad. Sci. USA*, Apr. 1995, pp. 4051-4055, vol. 92.

Chace. J.H. et al., "Regulation of Differentiation in CD5+ and Conventional B Cells—Sensitivity to LPS-Induced Differentiation and Interferon-γ-Mediated Inhibition of Differentiation", *Clinical Immunology and Immunopathology*, Sep. 1993, pp. 327-332, vol. 68, No. 3, Academic Press, Inc.

Chang. Y.N. et al., "The Palindromic Series I Repeats in the Simian Cytomegalovirus Major Immediate-Early Promoter Behave as Both Strong Basal Enhancers and Cyclic AMP Response Elements", *Journal of Virology*, Jan. 1990, pp. 264-277, vol. 64. No. 1, American Society of Microbiology.

Chu, R.S. et al., "CpG Oligodeoxynucleotides Act as Adjuvants that Switch on T Helper I (Th1) Immunity", *J. Exp. Med.*, Nov. 17, 1997, pp. 1623-1631, vol. 186, No. 10, The Rockefeller University Press.

Constant, P. et al., "Stimulation of Human γδ T Cells by Nonpeptidic Mycobacterial Ligands", Science, Apr. 8, 1994, pp. 267-270, vol. 264.

Constant, S.L. et al., "Induction of TH1 and TH2 CD4+ T Cell Responses: The Alternative Approaches", *Annu. Rev. Immunol.*, 1997, pp. 297-322, vol. 15, Annual Reviews, Inc.

Cowdery, J.S. et al., "Bacterial DNA Induces NK Cells to Produce IFN-γ In Vivo and Increases the Toxicity of Lipopolysaccharides", *The Journal of Immunology*, 1996, pp. 4570-4575, vol. 156, No. 12, The American Society of Immunologists.

Croft, M. et al., "Generation of Polarized Antigen-specific CD8 Effector Populations: Reciprocal Action of Interleukin (IL)-4 and IL-12 in Promoting Type 2 Versus Type 1 Cytokine Profiles", *J. Exp. Med.*, Nov. 1994, pp. 1715-1726, vol. 180, The Rockefeller University Press.

Crosby, S.D. et al., "The Early Response Gene NGFI-C Encodes a Zinc Finger Transcriptional Activator and is a Member of the GCGGGGGCG (GSG) Element-Binding Protein Family", *Mol. Cell. Biol.*, 1991, pp. 3835-3841, vol. 11, American Society for Microbiology.

Crystal, R.G., "Transfer of Genes to Humans: Early Lessons and Obstacles to Success", *Science*, 1995, pp. 404-410, vol. 270.

D'Andrea, A. et al., "Interleukin 10 (IL-10) Inhibits Human Lymphocyte Interferon γ-Production by Suppressing Natural Killer Cell Stimulatory Factor/IL-12 Synthesis in Accessory Cells", *J. Exp. Med.*, Sep. 1993, pp. 1041-1048, vol. 178, The Rockefeller University Press.

Dapic, V. et al., "Antiproliferative Activity of G-Quartet Forming Oligonucleotides with Backbone and Sugar Modifications", *Proceedings of the AACR*, Mar. 2001, 1 Page, vol. 42, American Association for Cancer Research.

Davis, H.L., "Plasmid DNA expression systems for the purpose of immunization", *Curr. Opin. Biotechnol.*, Oct. 1997, pp. 635-640, vol. 8, No. 5.

Davis, H.L. et al., "CpG DNA is a Potent Enhancer of Specific Immunity in Mice Immunized with Recombinant Hepatitis B Surface Antigen", *J. Immunol.*, 1998, pp. 870-876, vol. 160, No. 2, The American Association of Immunologists.

Elkins, K.L. et al., "Bacterial DNA Containing CpG Motifs Stimulates Lymphocyte-Dependent Protection of Mice Against Lethal Infection with Intracellular Bacteria", *The Journal of Immunology*, 1999, pp. 2291-2298, vol. 162, The American Association of Immunologists.

Englisch, U. et al., "Chemically Modified Oligonucleotides as Probes and Inhibitors", *Angew. Chem. Int. Ed. Eng.*, Jun. 1991, pp. 613-629, vol. 30, No. 6, VCH Verlagsgesellschaft mbH.

Erb, K.J. et al., "Infection of Mice with *Mycobacterium bovis*-Bacillus Calmette-Guerin (BCG) Suppresses Allergen-induced Airway Eosinophilia", *J. Exp. Med.*, Feb. 16, 1998, pp. 561-569, vol. 187, No. 4, The Rockefeller University Press.

Etlinger, H.M., "Carrier sequence selection—one key to successful vaccines", *Immunology Today*, 1992, pp. 52-55, vol. 13, No. 2.

Fox, R.I., "Mechanism of Action of Hydroxychloroquine as an Antirheumatic Drug", *Seminars in Arthritis and Rheumatism*, Oct. 1993, pp. 82-91, vol. 23, No. 2, Suppl. 1, W. B. Saunders Company.

Gura, T., "Antisense Has Growing Pains", *Science*, Oct. 27, 1995, pp. 575-576, vol. 270.

Hadden, J.W. et al., "Chapter 24: Immunopharmacology—Immunomodulation and Immunotherapy", *JAMA*, Nov. 25, 1992, pp. 2964-2969, vol. 268, No. 20.

Hadden, J.W., "Immunomodulation—Immunostimulants", *TIPS*, May 1993, pp. 169-174, vol. 14, Elsevier Science Publishers Ltd. (UK).

Halpern, M.D. et al., "Bacterial DNA Induces Murine Interferon-γ Production by Stimulation of Interleukin-12 and Tumor Necrosis Factorα", *Cellular Immunology*, 1996, pp. 72-78, vol. 167, Article No. 0009, Academic Press, Inc.

Hartmann, G. et al., "Delineation of a CpG Phosphorothioate Oligodeoxynucleotide for Activating Primate Immune Responses In Vitro and In Vivo", *J. Immunol.*, 2000, pp. 1617-1624, vol. 164, The American Association of Immunologists.

Hatzfeld, J. et al., "Release of Early Human Hematopoietic Progenitors from Quiescence by Antisense Transforming Growth Factor β1 or Rb Oligonucleotides", *J. Exp. Med.*, Oct. 1991, pp. 925-929, vol. 174, The Rockefeller University Press.

Hawkes, N. et al., "Answer to asthma may lie in the soil", *The Times of London News International*, Sep. 18, 1999, p. 18, Times Newspapers Ltd.

Highfield, P.E., "Sepsis: The More, the Murkier", *Bio/Technology*, Aug. 1994, p. 828, vol. 12.

Hoeffler, J.P. et al., "Identification of Multiple Nuclear Factors That Interact with Cyclic Adenosine 3', 5'-Monophosphate Response Element-Binding Protein and Activating Transcription Factor-2 by Protein-Protein Interactions", *Molecular Endocrinology*, 1991, pp. 256-266, vol. 5, No. 2, The Endocrine Society.

Huang. L.Y. et al., "Induction and Regulation of Th1-Inducing Cytokines by Bacterial DNA, Lipopolysaccharide, and Heat-Inactivated Bacteria", *Infection and Immunity*, Dec. 1999, pp. 6257-6263, vol. 67, No. 12, American Society of Microbiology.

Hughes, J. a. et al., "Influence of Base Composition on Membrane Binding and Cellular Uptake of 10-mer Phosphorothioate Oligonucleotides in Chinese Hamster Ovary ($CH^RC5$) Cells", *Antisense Research and Development*, 1994, pp. 211-215, vol. 4, Mary Ann Liebert, Inc.

Iguchi-Ariga, S.M.M. et al., "CpG methylation of the cAMP-responsive enhancer/promoter sequence TGACGTCA abolishes specific factor binding as well as transcriptional activation", *Genes & Development*, 1989, pp. 612-619, vol. 3, Cold Spring Harbor Laboratory Press.

Irwin, A. et al., "Asthma may be reduced by vaccine from soil", *The Daily Telegraph*, p. 6, Sep. 18, 1999, The Daily Telegraph; Source: World Reporter.

Ishikawa, R. et al., "IFN Induction and Associated Changes in Splenic Leukocyte Distribution", *J. Immunol.*, May 1, 1993, pp. 3713-3727, vol. 150, No. 9, The American Association of Immunologists USA.

Iversen, P.L. et al., "Pharmacokinetics of an Antisense Phosphorothioate Oligodeoxynucleotide against *rev* from Human Immunodeficiency Virus Type 1 in the Adult Male Rat Following Single Injections and Continuous Infusion", *Antisense Research and Development*, 1994, pp. 43-52, vol. 4, Mary Ann Liebert, Inc.

Press Release from NewsRx.com, Jahnschmid. B. et al., "Type 1 allergy immunotherapy could get a boost from CpG oligodeoxynucleotide adjuvants", *Allergy Medicine (Animal Models)*, Jan. 16, 2000.

Jakway, J.P. et al., "Growth Regulation of the B Lymphoma Cell Line WEH1-231 by Anti-Immunoglobulin, Lipopolysaccharide, and Other Bacterial Products", *J. Immunol.*, Oct. 1, 1986, pp. 2225-2231, vol. 137, No. 7, The American Association of Immunologists USA.

Jaroszewski, J.W. et al., "Cellular uptake of antisense oligodeoxynucleotides", *Advanced Drug Delivery Reviews*, 1991, pp. 235-250, vol. 6, Elsevier.

Kataoka, T. et al., "Antitumor Activity of Synthetic Oligonucleotides with Sequences from cDNA Encoding Proteins of *Mycobacterium bovis* BCG", *Jpn. J. Cancer Res.*, Mar. 1992, pp. 244-247, vol. 83.

Kimura, Y. et al., "Binding of Oligoguanylate to Scavenger Receptors is Required for Oligonucleotides to Augment NK Cell Activity and Induce IFN", *J. Biochem.*, 1994, pp. 991-994, vol. 116, No. 5.

Kline, J.N. et al., "CpG Motif Oligonucleotides are Effective in Prevention of Bosinophilic Inflammation in a Murine Model of Asthma", *Journal of Investigative Medicine*, 1996, pp. 380A, vol. 44, No. 7.

Kline, J.N. et al., "Immune Redirection by CpG Oligonucleotides: Conversion of a Th2 Response to a Th1 Response in a Murine Model of Asthma", *Journal of Investigative Medicine*, 1997, pp. 282A, vol. 45, No. 3.

Kline, J.N. et al., "CpG Oligonucleotides can Reserve as Well as Prevent TH2-Mediated Inflammation in a Murine Model of Asthma", *Journal of Investigative Medicine*, 1997, p. 298A, vol. 45, No. 7.

Kline, J.N. et al., "CpG oligodeoxynucleotides do not require $T_{H1}$ cytokines to prevent eosinophilic airway inflammation in a murine model of asthma", *J. Allergy Clin. Immunol.*, Dec. 1999, pp. 1258-1264, vol. 104, No. 6.

Klinman, D.M. et al., "CpG motifs present in bacterial DNA rapidly induce lymphocytes to secrete interleukin 6, interleukin 12, and interferon γ", *Proc. Natl. Acad. Sci. USA*, Apr. 1996, pp. 2879-2883, vol. 93.

Klinman, D.M. et al., "CpG motifs as immune adjuvants", *Vaccine*, 1999, pp. 19-25, vol. 17, Elsevier Science Ltd.

Kou, K. et al., "Analysis and regulation of interferon-gamma production by peripheral blood lymphocytes from patients with bronchial asthma", *Arerugi.*, Mar. 1994, pp. 482-491, vol. 43, No. 3, Abstract.

Krieg, A.M. et al., "A Role for Endogenous Retroviral Sequences in the Regulation of Lymphocyte Activation", *The Journal of Immunology*, Oct. 1989, pp. 2448-2451, vol. 143, No. 8, The American Association of Immunologists.

Krieg, A.M. et al., "Uptake of Oligodeoxyribonucleotides by Lymphoid Cells is Heterogenous and Inducible", *Antisense Research and Development*, 1991, pp. 161-171, vol. 1, Mar Ann Liebert, Inc.

Krieg, A.M. et al., "Modification of antisense phosphodiester oligodeoxynucleotides by a 5' cholesteryl moiety increases cellular association and improves efficacy", *Proc. Natl. Acad. Sci. USA*, Feb. 1993, pp. 1048-1052, vol. 90.

Krieg, A.M. et al., "Phosphorothioate Oligodeoxynucleotides: Antisense or Anti-Protein?", *Antisense Research and Development*, 1995, p. 241, vol. 5, Mary Ann Liebert, Inc.

Krieg, A.M., "CpG DNA: A Pathogenic Factor in Systemic Lupus Erythematosus?", *Journal of Clinical Immunology*, 1995, pp. 284-292, vol. 15, No. 6.

Krieg, A.M. et al., "CpG motifs in bacterial DNA trigger direct B-cell activation", *Nature*, Apr. 6, 1995, pp. 546-549, vol. 374.

Krieg, A.M. et al., "Oligodeoxynucleotide Modifications Determine the Magnitude of B Cell Stimulation by CpG Motifs", *Antisense & Nucleic Acid Drug Development*, 1996, pp. 133-139, vol. 6. Mary Ann Liebert, Inc.

Krieg, A.M., "An innate immune defense mechanism based on the recognition of CpG motifs in microbial DNA", *J. Lab. Clin. Med.*, 1996, pp. 128-133, vol. 128.

Krieg, A.M., "Chapter 24: Leukocyte Stimulation by Oligodeoxynucleotides", *Applied Antisense Oligonucleotide Technology*, 1998, pp. 431-448, Wiley-Liss, Inc.

Krieg, A.M. et al., "The role of CpG dinucleotides in DNA vaccines", *Trends in Microbiology*, Jan. 1998, pp. 23-27, vol. 6, No. 1, Elsevier Science Ltd.

Krieg, A.M. et al., "Immune effects and therapeutic applications of CpG motifs in bacterial DNA", *Immunopharmacology*, 2000, pp. 303-305, vol. 48, Elsevier Science B.V.

Kuramoto, E. et al., "Oligonucleotide Sequences Required for Natural Killer Cell Activation", *Jpn. J. Cancer Res.*, Nov. 1992, pp. 1128-1131, vol. 83.

Lang, R. et al., "Guanosine-rich oligodeoxynucleotides induce proliferation of macrophage progenitors in cultures of murine bone marrow cells", *Eur. J. Immunol.*, 1999, pp. 3496-3506, vol. 29, Wiley-VCH Verlag GmbH.

Lederman, S. et al., "Polydeoxyguanine Motifs in a 12-mer Phosphorothioate Oligodeoxynucleotide Augment Binding to the v3 Loop of HIV-1 gp120 and Potency of HIV-1 Inhibition Independently of G-Tetrad Formation", *Antisense & Neucleic Acid Drug Development*, 1996, pp. 281-289, vol. 6, Mary Ann Liebert, Inc.

Lee, P.P. et al., "An Oligonucleotide Blocks Interferon-γ Signal Transduction", *Transplantation*, Nov. 15, 1996, pp. 1297-1301, vol. 62, No. 9, Williams & Wilkins USA.

Leonard, G.A. et al., "Conformation of Guanine-8-Oxoadenine Base Pairs in the Crystal Structure of d(CGCGAATT(O8A)GCG)", *Biochemistry*,1992, pp. 8415-8420, vol. 31, No. 36, American Chemical Society.

Lipford, G.B. et al., "CpG-containing synthetic oligonucleotides promote B and cytotoxic T cell responses to protein antigen: a new class of vaccine adjuvants", *Eur. J. Immunol.*, 1997, pp. 2340-2344, vol. 27, Wiley-VCH Verlag GmbH.

Lipford, G.B. et al., "Immunostimulatory DNA: sequence-dependent production of potentially harmful or useful cytokines", *Eur. J. Immunol.*, 1997, pp. 3420-3426, vol. 27, Wiley-VCH Verlag GmbH.

Lipford, G.B. et al., "Bacterial DNA as immune cell activator", *Trends Microbiol.*, 1998, pp. 496-500, vol. 6, No. 12, Elsevier Science.

Macaya, R.F. et al., "Thromin-binding DNA aptamer forms a unimolecular quadruplex structure in solution", *Proc. Natl. Acad. Sci. USA*, Apr. 1993, pp. 3745-3749, vol. 90.

MacFarlane, D.E. et al., "Antagonism of Immunostimulatory CpG-Oligodeoxynucleotides by Quinacrine, Chloroquine, and Structurally Related Compounds", *The Journal of Immunology*, 1998, pp. 1122-1131, vol. 160, No. 3, The American Association of Immunologists.

Maltese, J.Y. et al., "Sequence context of antisense RelA/NF-κB phosphorothioates determines specificity", *Nucleic Acids Research*, 1995, pp. 1146-1151, vol. 23, No. 7, Oxford University Press.

Mastrangelo, M.J. et al., "Gene Therapy for Human Cancer: An Essay for Clinicians", *Seminars in Oncology*, Feb. 1996, pp. 4-21, vol. 23 No. 1.

Matson, S. et al., "Nonspecific Suppression of [$^3$H]Thymidine Incorporation by "Control" Oligonucleotides", *Antisense Research and Development*, 1992, pp. 325-330, vol. 2, Mary Ann Liebert, Inc.

Matsukura, M. et al., "Regulation of viral expression of human immunodeficiency virus in vitro by an antisense phosphorothioate oligodeoxynucleotide against rev (art/trs) in chronically infected cells", *Proc. Natl. Acad. Sci. USA*, Jun. 1989, pp. 4244-4248, vol. 86.

McCluskie, M.J. et al., "Oral, intrarectal and intranasal immunizations using CpG and non-CpG oligodeoxynucleotides as adjuvants", *Vaccine*, 2001, pp. 413-422, vol. 19, Elsevier Science Ltd.

McCluskie, M.J. et al., "The potential of oligodeoxynucleotides as mucosal and partenteral adjuvants", *Vaccine*, 2001, pp. 2657-2660, vol. 19, Elsevier Science Ltd.

McIntyre, K.W. et al., "A Sense Phosphorothioate Oligonucleotide Directed to the Initiation Codon of Transcription Factor NF-κB p65 Causes Sequence-Specific Immune Stimulation", *Antisense Research and Development*, 1993, pp. 309-322, vol. 3, Mary Ann Liebert, Inc.

Messina, J.P. et al., "Stimulation of In Vitro Murine Lymphocyte Proliferation by Bacterial DNA", *The Journal of Immunology*, Sep. 15, 1991, pp. 1759-1764, vol. 147, No. 6, The American Association of Immunologists USA.

Messina, J.P. et al., "The Influence of DNA Structure on the in Vitro Stimulation of Murine Lymphocytes by Natural and Synthetic Polynucleotide Antigens", *Cellular Immunology*, 1993, pp. 148-157, vol. 147, Academic Press, Inc.

Press Release from NewsRx.com, Milgrom, H., "Treatment of Allergic Asthma with Monoclonal Anti-IgE Antibody", *The New England Journal of Medicine*, 1999, pp. 1966-1973, vol. 341.

Mojcik, C.F. et al., "Administration of a Phosphorothioate Oligonucleotide Antisense to Murine Endogenous Retroviral MCF env Causes Immune Effects in Vivo in a Sequence-Specific Manner", *Clinical Immunology and Immunopathology*, May 1993, pp. 130-136, vol. 67, No. 2, Academic Press, Inc.

Mottram, J.C. et al., "A Novel CDC2-related Protein Kinase from *Leishmania mexicana*, LmmCRK1, is Post-translationally Regulated during the Life Cycle", *The Journal of Biological Chemistry*, Oct. 5, 1993, pp. 21044-21052, vol. 268, No. 28, The American Society of Biochemistry and Molecular Biology, Inc. USA.

New England Biolabs, 1988-1989 Catalog.

Nyce, J.W. et al., "DNA antisense therapy for asthma in an animal model", *Nature*, Feb. 20, 1997, pp. 721-725, vol. 385.

Parronchi, P. et al., "Phosphorothioate Oligodeoxynucleotides Promote the In Vitro Development of Human Allergen-Specific CD4+ T Cells into Th1 Effectors", *J. Immunol.*, 1999, pp. 5946-5953, vol. 163.

Pisetsky, D.S. et al., "Stimulation of Murine Lymphocyte Proliferation by a Phosphorothioate Oligonucleotide with Antisense Activity for Herpes Simplex Virus", *Life Sciences*, 1994, pp. 101-107, vol. 54, Pergamon Press Ltd. USA.

Pisetsky, D.S. et al., "Stimulation of in vitro proliferation of murine lymphocytes by synthetic oligodeoxynucleotides", *Molecular Biology Reports*, 1993, pp. 217-221, vol. 18, Kluwer Academic Publishers Belgium.

Pisetsky, D.S., "Immunologic Consequences of Nucleic Acid Therapy", *Antisense Research and Development*, 1995, pp. 219-225, vol. 5, Mary Ann Liebert, Inc.

Pisetsky, D.S., "The Immunologic Properties of DNA", *J. Immunol.*, 1996. pp. 421-423, vol. 156, No. 2, The American Association of Immunologists.

Prasad, V. et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide", *Antimicrobial Agents and Chemotherapy*, Nov. 1999, pp. 2689-2696, vol. 43, No. 11, American Society of Microbiology.

Quddus, J. et al., "Treating Activated CD4+ T cells with Either of Two Distinct DNA Methyltransferase Inhibitors, 5-Azacytidine or Procainamide, is Sufficient to Cause a Lupus-like Disease in Syngeneic Mice", *The Journal of Clinical Investigation, Inc.*, Jul. 1993, pp. 38-53, vol. 92.

Ramanathan, M. et al., "Inhibition of Interferon-γ-Induced Major Histocompatibility Complex Class I Expression by Certain Oligodeoxynucleotides", *Transplantation*, Feb. 1994, pp. 612-615, vol. 57, No. 4, Williams & Wilkins USA.

Ramanathan, M. et al., "Characterization of the Oligodeoxynucleotide-mediated Inhibition of Interferon-γ-induced Major Histocompatibility Complex Class I and Intercellular Adhesion Molecule-1", *The Journal of Biological Chemistry*, Oct. 7, 1994, pp. 24564-24574, vol. 269, No. 40, The American Society of Biochemistry and Molecular Biology, Inc. USA.

Raz, E. et al., "Preferential induction of a $Th_1$ immune response and inhibition of specific IgE antibody formation by plasmid DNA immunization", *Proc. Natl. Acad. Sci. USA*, May 1996, pp. 5141-5145, vol. 93.

Ricci. M. et al., "T cells, cytokine, IgE and allergic airways inflammation", *J. Invest. Allergol. Clin. Immunol.*, Sep.-Oct. 1994, pp. 214-220, vol. 4, No. 5.

Rojanasakul, Y., "Antisense oligonucleotide therapeutics: drug delivery and targeting", *Advanced Drug Delivery Reviews*, 1996, pp. 115-131, vol. 18, Elsevier Science B.V.

Roman, M. et al., "Immunostimulatory DNA sequences function as T helper-1-promoting adjuvants", *Nature Medicine*, Aug. 1997, pp. 849-854, vol. 3, No. 8.

Sarmiento, U.M. et al., "In Vivo Toxicological Effects of rel A Antisense Phosphorothioates in CD-1 Mice", *Antisense Research and Development*, 1994, pp. 99-107, vol. 4, Mary Ann Liebert, Inc.

Sato, Y. et al., "Immunostimulatory DNA Sequences Necessary for Effective Intradermal Gene Immunization", *Science*, Jul. 19, 1996, pp. 352-354, vol. 273.

Schnell, N. et al., "Indentification and characterization of a *Saccharomyces cerevisiae* gene (PAR1) conferring resistance to iron chelators", *Eur. J. Biochem.*, 1991, pp. 487-493, vol. 200, FEBS.

Schwartz, D.A. et al., "Endotoxin responsiveness and grain dust-induced inflammation in the lower respiratory tract", *Am. J. Physiol.*, 1994, pp. L609-L617, vol. 267(5 Pt 1), American Physiological Society.

Schwartz, D.A. et al., "The Role of Endotoxin in Grain Dust-Induced Lung Disease", *Am. J. Respir. Crit. Care Med.*, 1995, pp. 603-608, vol. 152.

Schwartz, D.A. et al., "CpG Motifs in Bacterial DNA Cause Inflammation in the Lower Respiratory Tract", *The Journal of Clinical Investigation*, Jul. 1997, pp. 68-73, vol. 100, No. 1.

Segal, B.M. et al., "Microbial Products Induce Autoimmune Disease by an IL-12-Dependent Pathway", *J. Immunol.*, 1997, pp. 5087-5090, vol. 158, The American Association of Immunologists.

Shirakawa, T. et al., "The Inverse Association Between Tuberculin Responses and Atopic Disorder", *Science*, Jan. 3, 1997, pp. 77-79, vol. 275.

Sparwasser, T. et al., "Macrophages sense pathogens via DNA motifs: induction of tumor necrosis factor-α-mediated shock", *Eur. J. Immunl.*, 1997, pp. 1671-1679, vol. 27, VCH Verlagsgesellschaft mbH.

Spiegelberg. H.L. et al., "Recognition of T Cell Epitopes and Lymphokine Secretion by Rye Grass Allergen *Lolium perenne* 1-Specific Human T Cell Clones", *J. Immunol.*, May 1, 1994, pp. 4706-4711, vol. 152, No. 9, The American Association of Immunologists.

Stein, C.A. et al., "Oligodeoxynucleotides as Inhibitors of Gene Expression: A Review", *Cancer Research*, May 15, 1988, pp. 2659-2668, vol. 48.

Stuart, M., "Marketplace Strategies: The Asthma Challenge", *Start-Up*, Apr. 1999, pp. 12-20.

Stull, R.A. et al., "Antigene, Ribozyme and Aptamer Nucleic Acid Drugs: Progress and Prospects", *Pharmaceutical Research*, 1995, pp. 465-483, vol. 12, No. 4, Plenum Publishing Corp.

Subramanian, P.S. et al., "Theoretical considerations on the "spine of hydration" in the minor groove of d(CGCGAATTCGCG)•d(GCGCTTAAGCGC): Monte Carlo computer simulation", *Proc. Natl. Acad. Sci. USA*, Mar. 1988, pp. 1836-1840, vol. 85.

Sun, S. et al., "Mitogenicity of DNA from Different Organisms for Murine B Cells", *J. Immunol.*, 1997, pp. 3119-3125, vol. 159, The American Association of Immunologists.

Sun, S. et al., "Multiple effects of immunostimulatory DNA on T cells and the role of type 1 interferons", *Springer Semin Immunophathol.*, 2000, pp. 77-84, vol. 22, Springer-Verlag.

Talmadge, J.E. et al., "Immunomodulatory Effects in Mice of Polyinosinic-Polycytidylic Acid Complexed with Poly-L-lysine and Carboxymethylocellulose", *Cancer Research*, Mar. 1985, pp. 1058-1065, vol. 45.

Tanaka, T. et al., "An Antisense Oligonucleotide Complementary to a Sequence in Iγ2b Increases γ2b Germline Transcripts, Stimulates B Cell DNA Synthesis, and Inhibits Immunoglobulin Secretion", *The Journal of Experimental Medicine*, Feb. 1992, pp. 597-607, vol. 175.

Thorne, P.S., "Experimental Grain Dust Atmospheres Generated by Wet and Dry Aerosolization Techniques", *American Journal of Industrial Medicine*, 1994, pp. 109-112, vol. 25, Wiley-Liss, Inc.

Threadgill, D.S. et al., "Mitogenic synthetic polynucleotides suppress the antibody response to a bacterial polysaccharide", *Vaccine*, 1998, pp. 76-82, vol. 16, No. 1, Elsevier Science Ltd. Great Britain.

Tokunaga, T. et al, "A Synthetic Single-Stranded DNA, Poly(dG.dC), Induces Interferon-α/β and -γ, Augments Natural Killer Activity, and Suppresses Tumor Growth", *Jpn. J. Cancer Res. (Gann)*. Jun. 1988. pp. 682-686, vol. 79.

Tokunaga, T. et al., "Synthetic Oligonucleotides with Particular Base Sequences from the cDNA Encoding Proteins of *Mycobacterium*

*bovis* BCG Induce Interferons and Activate Natural Killer Cells", 1992, *Microbiol. Immunol.*, 1992, pp. 55-66, vol. 36, No. 1.

Uhlmann, E. et al., "Antisense Oligonucleotides: A New Therapeutic Principle", *Chemical Reviews*, Jun. 1990, pp. 544-584, vol. 90, No. 4.

Vallin, H. et al., "Anti-Double-Stranded DNA Antibodies and Immunostimulatory Plasmid DNA in Combination with Mimic the Endogenous IFN-α Inducer in Systemic Lupus Erythematosus", *J. Immunol.*, Dec. 1, 1999, pp. 6306-6313, vol. 163, No. 11, The American Association of Immunologists.

Van Uden, J. et al., "Immunostimulatory DNA and applications to allergic disease", *J. Allergy Clin. Immunol.*, Nov. 1999, pp. 902-910, vol. 104, No. 5, Mosby, Inc.

Wagner, R.W., "Gene inhibition using antisense oligodeoxynucleotides", *Nature*, Nov. 24, 1994, pp. 333-335, vol. 372.

Walker, C. et al., "Activated T Cells and Cytokines in Bronchoalveolar Lavages from Patients with Various Lung Diseases Associated with Eosinophila", *Am. J. Respir. Crit. Care Med.*, 1994, pp. 1038-1048, vol. 150.

Wallace, R.B. et al., "Oligonucleotide Probes for the Screening of Recombinant DNA Libraries", *Methods in Enzymology*, 1987, pp. 432-442, vol. 152, Academic Press, Inc.

Weiss, R., "Upping the Antisense Ante—Scientists bet on profits from reverse genetics", *Science News*, Feb. 16, 1991, pp. 108-109, vol. 139.

Whalen, R.G., "DNA Vaccines for Emerging Infectious Diseases: What If?", *Emerging Infectious Diseases*, Jul.-Sep. 1996, pp. 168-175. vol, 2, No. 3.

Wloch, M.K. et al., "The Influence of DNA Sequence on the Immunostimulatory Properties of Plasmid DNA Vectors", *Human Gene Therapy*, Jul. 1, 1998, pp. 1436-1447, vol. 9, Mary Ann Liebert, Inc.

Wooldridge, J.E. et al., "Select unmethylated CpG oligodeoxynucleotide improve antibody-dependent cellular cytotoxicity in vitro and in vivo", *Proceedings of the American Association of Cancer Research* No. 3253, Mar. 1996, p. 477, vol. 37.

Wu, G.Y. et al., "Receptor-mediated Gene Delivery and Expression in Vivo", *The Journal of Biological Chemistry*, Oct. 15, 1988, pp. 14621-14624, vol. 263, No. 29, The American Society of Biochemistry and Molecular Biology, Inc. USA.

Wu-Pong, S., "Oligonucleotides: Opportunities for Drug Therapy and Research", *Pharmaceutical Technology*, Oct. 1994, pp. 102-114, vol. 18.

Yamamoto, S. et al., "In vitro Augmentation of Natural Killer Cell Activity and Production of Interferon-α/β and -γ with Deoxyribonucleic Acid Fraction from *Mycobacterium bovis* BCG", *Jpn. J. Cancer Res. (Gann)*, Jul. 1988, pp. 866-873, vol. 79.

Yamamoto, S. et al., "DNA from Bacteria, but Not from Vertebrates, Induces Interferons, Activates Natural Killer Cells and Inhibits Tumor Growth", *Microbiol. Immunol.*, 1992, pp. 983-997, vol. 36, No. 9.

Yamamoto, S. et al., "Unique Palindromic Sequences in Synthetic Oligonucleotides are Required to Induce INF and Augment INF-Mediated Natural Killer Activity", *The Journal of Immunology*, Jun. 15, 1992, pp. 4072-4076, vol. 148, No. 12, The American Association of Immunologists USA.

Yamamoto, S., "Mode of Action of Oligonucleotide Fraction Extracted from *Mycobaterium bovis* BCG", *Kekkaku*, 1994, pp. 29-32, vol. 69, No. 9.

Yamamoto, T. et al., "Synthetic Oligonucleotides with Certain Palindromes Stimulate Interferon Production of Human Peripheral Blood Lymphocytes in vitro", *Jpn. J. Cancer Res.*, Aug. 1994, pp. 775-779, vol. 85.

Yamamoto, T. et al., "Ability of Oligonucleotides with Certain Palindromes to Induce Interferon Production and Augment Natural Killer Cell Activity is Associated with Their Base Length", *Antisense Research and Development*, 1994, pp. 119-123, vol. 4, Mary Ann Liebert, Inc.

Yamamoto, T. et al., "Lipofection of Synthetic Oligodeoxyribonucleotide Having a Palindromic Sequence of AACGTT to Murine Splenocytes Enhances Interferon Production and Natural Killer Activity", *Microbiol. Immunol.*, 1994, pp. 831-836, vol. 38, No. 10.

Yi, A.K. et al., "IFN-γ Promotes IL-6 and IgM Secretion in Response to CpG Motifs in Bacterial DNA and Oligodeoxynucleotides", *The Journal of Immunology*, 1996, pp. 558-564, vol. 156, No. 2, The American Association of Immunologists.

Yi, A.K. et al., "Rapid Immune Activation by CpG Motifs in Bacterial DNA-Systemic Induction of IL-6 Transcription Through an Antioxidant-Sensitive Pathway", *The Journal of Immunology*, 1996, pp. 5394-5402, vol. 157, The American Association of Immunologists.

Yi, A.K. et al., "Cutting Edge: Rapid Induction of Mitogen-Activated Protein Kinases by Immune Stimulatory CpG DNA", *The Journal of Immunology*, Nov. 1, 1998, pp. 4493-4497, vol. 161, No. 9, The American Association of Immunologists.

Yi, A.K. et al., "CpG Oligodeoxyribonucleotides Rescue Mature Spleen B Cells from Spontaneous Apoptosis and Promote Cell Cycle Entry", *The Journal of Immunology*, 1998, pp. 5898-5906, vol. 160, No. 12, The American Association of Immunologists.

Zhao, Q. et al., "Comparison of Cellular Binding and Uptake of Antisense Phosphodiester, Phosphorothioate, and Mixed Phosphorothioate and Methylphosphonate Oligonucleotides", *Antisense Research and Development*, 1993, pp. 53-66, vol. 3, Mary Ann Liebert, Inc.

Zhao, Q. et al., "Stage-Specific Oligonucleotide Uptake in Murine Bone Marrow B-Cell Precursors", *Blood*, Dec. 1, 1994, pp. 3660-3666, vol. 84, No. 11.

Zhao, Q. et al., "Site of Chemical Modifications in CpG Containing Phosphorothioate Oligodeoxynucleotide Modulates Its Immunostimulatory Activity", *Bioorg. Med. Chem. Lett.*, Dec. 20, 1999, pp. 3453-3458, vol. 9, No. 24.

\* cited by examiner

SEQUENCE LISTING

<160> NUMBER OF SEQ ID NOS: 1093

<210> SEQ ID NO 1
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1
tctcccagcg tgcgccat                                              18

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
ataatccagc ttgaaccaag                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
ataatcgacg ttcaagcaag                                            20

<210> SEQ ID NO 4
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 4
taccgcgtgc gaccctct                                              18

<210> SEQ ID NO 5
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 5 ggggagggt                                                         9

<210> SEQ ID NO 6
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 6 ggggagggg                                                         9

<210> SEQ ID NO 7
<211> LENGTH: 9

```
<212> TYPE: DNA
<213> ORGANISM: Artificial Sequence
<220> FEATURE:
<223> OTHER INFORMATION: Synthetic Sequence

<400> SEQUENCE: 7 ggtgaggtg                                                                            9

<210> SEQ ID NO 8
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 8
tccatgtngt tcctgatgct                                                               20

<210> SEQ ID NO 9
<211> LENGTH: 15
<212> TYPE: DNA
<213> ORGANISM: Artificial Sequence
<220> FEATURE:
<221> NAME/KEY: modified_base
<222> LOCATION: (11)...(11)
<223> OTHER INFORMATION: m5c
<220> FEATURE:
<223> OTHER INFORMATION: Synthetic Sequence

<400> SEQUENCE: 9
gctaccttag ngtga                                                                    15

<210> SEQ ID NO 10
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 10
tccatgangt tcctgatgct                                                               20

<210> SEQ ID NO 11
<211> LENGTH: 20
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
<220> FEATURE:
<223> OTHER INFORMATION: Synthetic Sequence

<400> SEQUENCE: 11
tccatgacgt tcntgatgct                                                               20

<210> SEQ ID NO 12
<211> LENGTH: 15
<212> TYPE: DNA
<213> ORGANISM: Artificial Sequence
<220> FEATURE:
```

```
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 12
gctagangtt agtgt                                                          15

<210> SEQ ID NO 13
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 13
agctccatgg tgctcactg                                                      19

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 14
ccacgtcgac cctcaggcga                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 15
gcacatcgtc ccgcagccga                                                     20

<210> SEQ ID NO 16
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 16
gtcactcgtg gtacctcga                                                      19

<210> SEQ ID NO 17
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 17
gttggataca ggccagactt tgttg                                               25

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 18
```

-continued gattcaactt gcgctcatct taggc                                    25

<210> SEQ ID NO 19
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 19
accatggacg aactgtttcc cctc                                     24

<210> SEQ ID NO 20
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 20
accatggacg agctgtttcc cctc                                     24

<210> SEQ ID NO 21
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 21
accatggacg acctgtttcc cctc                                     24

<210> SEQ ID NO 22
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 22
accatggacg tactgtttcc cctc                                     24

<210> SEQ ID NO 23
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 23
accatggacg gtctgtttcc cctc                                     24

<210> SEQ ID NO 24
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 24
accatggacg ttctgtttcc cctc                                     24

<210> SEQ ID NO 25
<211> LENGTH: 25
<212> TYPE: DNA

```
<213> ORGANISM: Artificial Sequence
<220> FEATURE:
<223> OTHER INFORMATION: Synthetic Sequence

<400> SEQUENCE: 25
ccactcacat ctgctgctcc acaag                                              25

<210> SEQ ID NO 26
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 26
acttctcata gtccctttgg tccag                                              25

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
tccatgagct tcctgagtct                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (9)...(9)
<223> OTHER INFORMATION: I
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (15)...(15)
<223> OTHER INFORMATION: I

<400> SEQUENCE: 28
gaggaaggng nggangacgt                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (7)...(7)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (18)...(18)
<223> OTHER INFORMATION: I

<400> SEQUENCE: 29
gtgaatncgt tcncgggnct                                                    20
```

```
<210> SEQ ID NO 30
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 30 aaaaaa                                                                      6

<210> SEQ ID NO 31
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 31 cccccc                                                                      6

<210> SEQ ID NO 32
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 32 ctgtca                                                                      6

<210> SEQ ID NO 33
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 33 tcgtag                                                                      6

<210> SEQ ID NO 34
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 34 tcgtgg                                                                      6

<210> SEQ ID NO 35
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 35 cgtcgt                                                                      6

<210> SEQ ID NO 36
<211> LENGTH: 20
<212> TYPE: DNA
<213> ORGANISM: Artificial Sequence
<220> FEATURE:
```

<223> OTHER INFORMATION: Synthetic Sequence

<400> SEQUENCE: 36
tccatgtcgg tcctgagtct                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
tccatgccgg tcctgagtct                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
tccatgacgg tcctgagtct                                                  20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
tccatgacgg tcctgagtct                                                  20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
tccatgtcga tcctgagtct                                                  20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
tccatgtcgc tcctgagtct                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 42
tccatgtcgt tcctgagtct                                                  20

```
<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
tccatgacgt tcctgagtct                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
tccataacgt tcctgagtct                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
tccatgacgt ccctgagtct                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 46
tccatcacgt gcctgagtct                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
tccatgctgg tcctgagtct                                               20

<210> SEQ ID NO 48
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 48
tccatgtngg tcctgagtct                                               20

<210> SEQ ID NO 49
<211> LENGTH: 39
<212> TYPE: DNA
```

<213> ORGANISM: Artificial Sequence
<220> FEATURE:
<223> OTHER INFORMATION: Synthetic Sequence

<400> SEQUENCE: 49
ccgcttcctc cagatgagct catgggtttc tccaccaag                              39

<210> SEQ ID NO 50
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 50
cttggtggag aaacccatga gctcatctgg aggaagcgg                              39

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
ccccaaaggg atgagaagtt                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 52
agatagcaaa tcggctgacg                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 53
ggttcacgtg ctcatggctg                                                   20

<210> SEQ ID NO 54
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 54
tctcccagcg tgcgccat                                                     18

<210> SEQ ID NO 55
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 55
tctcccagcg tgcgccat                                                     18

```
<210> SEQ ID NO 56
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 56
taccgcgtgc gaccctct                                                 18

<210> SEQ ID NO 57
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 57
ataatccagc ttgaaccaag                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 58
ataatcgacg ttcaagcaag                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 59
tccatgattt tcctgatttt                                               20

<210> SEQ ID NO 60
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 60 ttgtttttt gttttttgt tttt                                            24

<210> SEQ ID NO 61
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 61
ttttttttgt ttttttgttt tt                                            22

<210> SEQ ID NO 62
<211> LENGTH: 24
<212> TYPE: DNA
<213> ORGANISM: Artificial Sequence
<220> FEATURE:
```

```
<223> OTHER INFORMATION: Synthetic Sequence

<400> SEQUENCE: 62
tgctgctttt gtgcttttgt gctt                                          24

<210> SEQ ID NO 63
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 63
tgctgcttgt gcttttgtgc tt                                            22

<210> SEQ ID NO 64
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 64
gcattcatca ggcgggcaag aat                                           23

<210> SEQ ID NO 65
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 65
taccgagctt cgacgagatt tca                                           23

<210> SEQ ID NO 66
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 66
gcatgacgtt gagct                                                    15

<210> SEQ ID NO 67
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 67
cacgttgagg ggcat                                                    15

<210> SEQ ID NO 68
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 68
ctgctgagac tggag                                                    15
```

```
<210> SEQ ID NO 69
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 69
tccatgacgt tcctgacgtt                                          20

<210> SEQ ID NO 70
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 70
gcatgagctt gagctga                                             17

<210> SEQ ID NO 71
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 71
tcagcgtgcg cc                                                  12

<210> SEQ ID NO 72
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 72
atgacgttcc tgacgtt                                             17

<210> SEQ ID NO 73
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 73
ttttggggtt ttggggtttt                                          20

<210> SEQ ID NO 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
tctaggcttt ttaggcttcc                                          20

<210> SEQ ID NO 75
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 75
tgcatttttt aggccaccat                                           20

<210> SEQ ID NO 76
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 76
tctcccagcg tgcgtgcgcc at                                        22

<210> SEQ ID NO 77
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 77
tctcccagcg ggcgcat                                              17

<210> SEQ ID NO 78
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 78
tctcccagcg agcgccat                                             18

<210> SEQ ID NO 79
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 79
tctcccagcg cgcgccat                                             18

<210> SEQ ID NO 80
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 80
ggggtgacgt tcagggggg                                            19

<210> SEQ ID NO 81
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 81
ggggtccagc gtgcgccatg gggg                                      24

<210> SEQ ID NO 82
<211> LENGTH: 19

```
<212> TYPE: DNA
<213> ORGANISM: Artificial Sequence
<220> FEATURE:
<223> OTHER INFORMATION: Synthetic Sequence

<400> SEQUENCE: 82
ggggtgtcgt tcagggggg                                                  19

<210> SEQ ID NO 83
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 83
tccatgtcgt tcctgtcgtt                                                 20

<210> SEQ ID NO 84
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 84
tccatagcgt tcctagcgtt                                                 20

<210> SEQ ID NO 85
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 85
tcgtcgctgt ctccgcttct t                                               21

<210> SEQ ID NO 86
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 86
gcatgacgtt gagct                                                      15

<210> SEQ ID NO 87
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 87
tctcccagcg tgcgccatat                                                 20

<210> SEQ ID NO 88
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<221> NAME/KEY: modified_base
```

```
<222> LOCATION: (17)...(17)
<223> OTHER INFORMATION: m5c
<220> FEATURE:
<223> OTHER INFORMATION: Synthetic Sequence

<400> SEQUENCE: 88
tccatgangt tcctgangtt                                              20

<210> SEQ ID NO 89
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 89
gcatgangtt gagct                                                   15

<210> SEQ ID NO 90
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 90
tccagcgtgc gccata                                                  16

<210> SEQ ID NO 91
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 91
tctcccagcg tgcgccat                                                18

<210> SEQ ID NO 92
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 92
tccatgagct tcctgagtct                                              20

<210> SEQ ID NO 93
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 93
gcatgtcgtt gagct                                                   15

<210> SEQ ID NO 94
<211> LENGTH: 19
<212> TYPE: DNA
<213> ORGANISM: Artificial Sequence
<220> FEATURE:
```

-continued

```
<223> OTHER INFORMATION: Synthetic Sequence

<400> SEQUENCE: 94
tcctgacgtt cctgacgtt                                              19

<210> SEQ ID NO 95
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 95
gcatgatgtt gagct                                                  15

<210> SEQ ID NO 96
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 96
gcatttcgag gagct                                                  15

<210> SEQ ID NO 97
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 97
gcatgtagct gagct                                                  15

<210> SEQ ID NO 98
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 98
tccaggacgt tcctagttct                                             20

<210> SEQ ID NO 99
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 99
tccaggagct tcctagttct                                             20

<210> SEQ ID NO 100
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 100
tccaggatgt tcctagttct                                             20
```

```
<210> SEQ ID NO 101
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 101
tccagtctag gcctagttct                                                   20

<210> SEQ ID NO 102
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 102
tccagttcga gcctagttct                                                   20

<210> SEQ ID NO 103
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 103
gcatggcgtt gagct                                                        15

<210> SEQ ID NO 104
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 104
gcatagcgtt gagct                                                        15

<210> SEQ ID NO 105
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 105
gcattgcgtt gagct                                                        15

<210> SEQ ID NO 106
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 106
gcttgcgttg cgttt                                                        15

<210> SEQ ID NO 107
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 107
tctcccagcg ttgcgccata t                                              21

<210> SEQ ID NO 108
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 108
tctcccagcg tgcgttatat                                                20

<210> SEQ ID NO 109
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 109
tctccctgcg tgcgccatat                                                20

<210> SEQ ID NO 110
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 110
tctgcgtgcg tgcgccatat                                                20

<210> SEQ ID NO 111
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 111
tctcctagcg tgcgccatat                                                20

<210> SEQ ID NO 112
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 112
tctcccagcg tgcgcctttt                                                20

<210> SEQ ID NO 113
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_difference
<222> LOCATION: (5)...(5)
<223> OTHER INFORMATION: n is a or g or c or t/u
<220> FEATURE:
<221> NAME/KEY: misc_difference
<222> LOCATION: (6)...(6)
<223> OTHER INFORMATION: d is a or g or t/u; not c
```

```
<220> FEATURE:
<221> NAME/KEY: misc_difference
<222> LOCATION: (9)...(10)
<223> OTHER INFORMATION: h is a or c or t/u; not g

<400> SEQUENCE: 113
gctandcghh agc                                                          13

<210> SEQ ID NO 114
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 114
tcctgacgtt ccc                                                          13

<210> SEQ ID NO 115
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 115
ggaagacgtt aga                                                          13

<210> SEQ ID NO 116
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 116
tcctgacgtt aga                                                          13

<210> SEQ ID NO 117
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 117
tcagaccagc tggtcgggtg ttcctga                                           27

<210> SEQ ID NO 118
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 118
tcaggaacac ccgaccagct ggtctga                                           27

<210> SEQ ID NO 119
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 119
```
gctagtcgat agc                                                    13

<210> SEQ ID NO 120
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 120
gctagtcgct agc                                                    13

<210> SEQ ID NO 121
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 121
gcttgacgtc tagc                                                   14

<210> SEQ ID NO 122
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 122
gcttgacgtt tagc                                                   14

<210> SEQ ID NO 123
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 123
gcttgacgtc aagc                                                   14

<210> SEQ ID NO 124
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 124
gctagacgtt tagc                                                   14

<210> SEQ ID NO 125
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 125
tccatgacat tcctgatgct                                             20

<210> SEQ ID NO 126
<211> LENGTH: 14
<212> TYPE: DNA
<213> ORGANISM: Artificial Sequence

```
<220> FEATURE:
<223> OTHER INFORMATION: Synthetic Sequence

<400> SEQUENCE: 126
gctagacgtc tagc                                                         14

<210> SEQ ID NO 127
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 127
ggctatgtcg ttcctagcc                                                    19

<210> SEQ ID NO 128
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 128
ggctatgtcg atcctagcc                                                    19

<210> SEQ ID NO 129
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 129
ctcatgggtt tctccaccaa g                                                 21

<210> SEQ ID NO 130
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 130
cttggtggag aaacccatga g                                                 21

<210> SEQ ID NO 131
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 131
tccatgacgt tcctagttct                                                   20

<210> SEQ ID NO 132
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 132
ccgcttcctc cagatgagct catg                                              24
```

<210> SEQ ID NO 133
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 133
catgagctca tctggaggaa gcgg                                    24

<210> SEQ ID NO 134
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 134
ccagatgagc tcatgggttt ctcc                                    24

<210> SEQ ID NO 135
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 135
ggagaaaccc atgagctcat ctgg                                    24

<210> SEQ ID NO 136
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 136
agcatcagga acgacatgga                                         20

<210> SEQ ID NO 137
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 137
tccatgacgt tcctgacgtt                                         20

<210> SEQ ID NO 138
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 138
gcgcgcgcgc gcgcgcgcg                                          19

<210> SEQ ID NO 139
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 139
ccggccggcc ggccggccgg                                               20

<210> SEQ ID NO 140
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 140
ttccaatcag ccccacccgc tctggcccca ccctcaccct cca                     43

<210> SEQ ID NO 141
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 141
tggagggtga gggtggggcc agagcgggtg gggctgattg gaa                     43

<210> SEQ ID NO 142
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 142
tcaaatgtgg gattttccca tgagtct                                       27

<210> SEQ ID NO 143
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 143
agactcatgg gaaaatccca catttga                                       27

<210> SEQ ID NO 144
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 144
tgccaagtgc tgagtcacta ataaaga                                       27

<210> SEQ ID NO 145
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 145
tctttattag tgactcagca cttggca                                       27

<210> SEQ ID NO 146

<211> LENGTH: 31
<212> TYPE: DNA
<213> ORGANISM: Artificial Sequence
<220> FEATURE:
<223> OTHER INFORMATION: Synthetic Sequence

<400> SEQUENCE: 146
tgcaggaagt ccgggttttc cccaacccccc c                          31

<210> SEQ ID NO 147
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 147 gggggggttgg ggaaaacccg gacttcctgc a                          31

<210> SEQ ID NO 148
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 148
ggggactttc cgctggggac tttccagggg gactttcc                    38

<210> SEQ ID NO 149
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 149
tccatgacgt tcctctccat gacgttcctc tccatgacgt tcctc            45

<210> SEQ ID NO 150
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 150
gaggaacgtc atggagagga acgtcatgga gaggaacgtc atgga            45

<210> SEQ ID NO 151
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 151
ataatagagc ttcaagcaag                                        20

<210> SEQ ID NO 152
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 152

```
tccatgacgt tcctgacgtt                                                    20

<210> SEQ ID NO 153
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 153
tccatgacgt tcctgacgtt                                                    20

<210> SEQ ID NO 154
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 154
tccaggactt tcctcaggtt                                                    20

<210> SEQ ID NO 155
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 155
tcttgcgatg ctaaaggacg tcacattgca caatcttaat aaggt                        45

<210> SEQ ID NO 156
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 156
accttattaa gattgtgcaa tgtgacgtcc tttagcatcg caaga                        45

<210> SEQ ID NO 157
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 157
tcctgacgtt cctggcggtc ctgtcgct                                           28

<210> SEQ ID NO 158
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 158
tcctgtcgct cctgtcgct                                                     19

<210> SEQ ID NO 159
<211> LENGTH: 15
<212> TYPE: DNA
```

<213> ORGANISM: Artificial Sequence
<220> FEATURE:
<223> OTHER INFORMATION: Synthetic Sequence

<400> SEQUENCE: 159
tcctgacgtt gaagt                                                            15

<210> SEQ ID NO 160
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 160
tcctgtcgtt gaagt                                                            15

<210> SEQ ID NO 161
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 161
tcctggcgtt gaagt                                                            15

<210> SEQ ID NO 162
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 162
tcctgccgtt gaagt                                                            15

<210> SEQ ID NO 163
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 163
tccttacgtt gaagt                                                            15

<210> SEQ ID NO 164
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 164
tcctaacgtt gaagt                                                            15

<210> SEQ ID NO 165
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 165
tcctcacgtt gaagt                                                            15

<210> SEQ ID NO 166
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 166
tcctgacgat gaagt                                                          15

<210> SEQ ID NO 167
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 167
tcctgacgct gaagt                                                          15

<210> SEQ ID NO 168
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 168
tcctgacggt gaagt                                                          15

<210> SEQ ID NO 169
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 169
tcctgacgta gaagt                                                          15

<210> SEQ ID NO 170
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 170
tcctgacgtc gaagt                                                          15

<210> SEQ ID NO 171
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 171
tcctgacgtg gaagt                                                          15

<210> SEQ ID NO 172
<211> LENGTH: 15
<212> TYPE: DNA
<213> ORGANISM: Artificial Sequence
<220> FEATURE:

<223> OTHER INFORMATION: Synthetic Sequence

<400> SEQUENCE: 172
tcctgagctt gaagt                                                          15

<210> SEQ ID NO 173
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 173
gggggacgtt ggggg                                                          15

<210> SEQ ID NO 174
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 174
tcctgacgtt ccttc                                                          15

<210> SEQ ID NO 175
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 175
tctcccagcg agcgagcgcc at                                                  22

<210> SEQ ID NO 176
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 176
tcctgacgtt cccctggcgg tcccctgtcg ct                                       32

<210> SEQ ID NO 177
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 177
tcctgtcgct cctgtcgctc ctgtcgct                                            28

<210> SEQ ID NO 178
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 178
tcctggcggg gaagt                                                          15

```
<210> SEQ ID NO 179
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 179
tcctgangtt gaagt                                                    15

<210> SEQ ID NO 180
<211> LENGTH: 15
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<220> FEATURE:
<223> OTHER INFORMATION: Synthetic Sequence

<400> SEQUENCE: 180
tcntgacgtt gaagt                                                    15

<210> SEQ ID NO 181
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 181
tcctagcgtt gaagt                                                    15

<210> SEQ ID NO 182
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 182
tccagacgtt gaagt                                                    15

<210> SEQ ID NO 183
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 183
tcctgacggg gaagt                                                    15

<210> SEQ ID NO 184
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 184
tcctggcggt gaagt                                                    15
```

<210> SEQ ID NO 185
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 185
ggctccgggg agggaattttt tgtctat                                    27

<210> SEQ ID NO 186
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 186
atagacaaaa attccctccc cggagcc                                     27

<210> SEQ ID NO 187
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 187
tccatgagct tccttgagtc t                                           21

<210> SEQ ID NO 188
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 188
tcgtcgctgt ctccgcttct t                                           21

<210> SEQ ID NO 189
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 189
tcgtcgctgt ctccgcttct t                                           21

<210> SEQ ID NO 190
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 190
tcgagacatt gcacaatcat ctg                                         23

<210> SEQ ID NO 191
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 191
cagattgtgc aatgtctcga                                                    20

<210> SEQ ID NO 192
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 192
tccatgtcgt tcctgatgcg                                                    20

<210> SEQ ID NO 193
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 193
gcgatgtcgt tcctgatgct                                                    20

<210> SEQ ID NO 194
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 194
gcgatgtcgt tcctgatgcg                                                    20

<210> SEQ ID NO 195
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 195
tccatgtcgt tccgcgcgcg                                                    20

<210> SEQ ID NO 196
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 196
tccatgtcgt tcctgccgct                                                    20

<210> SEQ ID NO 197
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 197
tccatgtcgt tcctgtagct                                                    20

<210> SEQ ID NO 198

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 198
gcggcgggcg gcgcgcgccc                                                    20

<210> SEQ ID NO 199
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 199
atcaggaacg tcatgggaag c                                                  21

<210> SEQ ID NO 200
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 200
tccatgagct tcctgagtct                                                    20

<210> SEQ ID NO 201
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 201 tcaacgtt                                                                  8

<210> SEQ ID NO 202
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 202 tcaagctt                                                                  8

<210> SEQ ID NO 203
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 203
tcctgtcgtt cctgtcgtt                                                     19

<210> SEQ ID NO 204
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 204
```

```
tccatgtcgt ttttgtcgtt                                              20
```

<210> SEQ ID NO 205
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 205

```
tcctgtcgtt ccttgtcgtt                                              20
```

<210> SEQ ID NO 206
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 206

```
tccttgtcgt tcctgtcgtt                                              20
```

<210> SEQ ID NO 207
<211> LENGTH: 29
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 207

```
tccattccat gacgttcctg atgcttcca                                    29
```

<210> SEQ ID NO 208
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 208

```
tcctgtcgtt ttttgtcgtt                                              20
```

<210> SEQ ID NO 209
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 209

```
tcgtcgctgt ctccgcttct t                                            21
```

<210> SEQ ID NO 210
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 210

```
tcgtcgctgt ctgcccttct t                                            21
```

<210> SEQ ID NO 211
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 211
tcgtcgctgt tgtcgtttct t                                              21

<210> SEQ ID NO 212
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 212
tcctgtcgtt cctgtcgttg gaacgacagg                                     30

<210> SEQ ID NO 213
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 213
tcctgtcgtt cctgtcgttt caacgtcagg aacgacagga                          40

<210> SEQ ID NO 214
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 214
ggggtctgtc gttttggggg g                                              21

<210> SEQ ID NO 215
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 215
ggggtctgtg cttttggggg g                                              21

<210> SEQ ID NO 216
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 216
tccggccgtt gaagt                                                     15

<210> SEQ ID NO 217
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 217
tccggacggt gaagt                                                    15

<210> SEQ ID NO 218
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 218
tcccgccgtt gaagt                                                    15

<210> SEQ ID NO 219
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 219
tccagacggt gaagt                                                    15

<210> SEQ ID NO 220
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 220
tcccgacggt gaagt                                                    15

<210> SEQ ID NO 221
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 221
tccagagctt gaagt                                                    15

<210> SEQ ID NO 222
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<221> NAME/KEY: modified_base
<222> LOCATION: (17)...(17)
<223> OTHER INFORMATION: m5c
<220> FEATURE:
<223> OTHER INFORMATION: Synthetic Sequence

<400> SEQUENCE: 222
tccatgtngt tcctgtngtt                                               20

<210> SEQ ID NO 223
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 223
tccatgacgt tcctgacgtt                                              20

<210> SEQ ID NO 224
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 224
ggggttgacg ttttgggggg                                              20

<210> SEQ ID NO 225
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 225
tccaggactt ctctcaggtt                                              20

<210> SEQ ID NO 226
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 226
tttttttttt tttttttttt                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 227
tccatgccgt tcctgccgtt                                              20

<210> SEQ ID NO 228
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 228
tccatggcgg gcctggcggg                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 229
tccatgacgt tcctgccgtt                                              20

<210> SEQ ID NO 230
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 230
tccatgacgt tcctggcggg                                           20

<210> SEQ ID NO 231
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 231
tccatgacgt tcctgcgttt                                           20

<210> SEQ ID NO 232
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 232
tccatgacgg tcctgacggt                                           20

<210> SEQ ID NO 233
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 233
tccatgcgtg cgtgcgtttt                                           20

<210> SEQ ID NO 234
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 234
tccatgcgtt gcgttgcgtt                                           20

<210> SEQ ID NO 235
<211> LENGTH: 30
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 235
tccattccat tctaggcctg agtcttccat                                30

<210> SEQ ID NO 236
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 236
tccatagcgt tcctagcgtt                                               20

<210> SEQ ID NO 237
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 237
tccatgtcgt tcctgtcgtt                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 238
tccatagcga tcctagcgat                                               20

<210> SEQ ID NO 239
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 239
tccattgcgt tccttgcgtt                                               20

<210> SEQ ID NO 240
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 240
tccatagcgg tcctagcggt                                               20

<210> SEQ ID NO 241
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 241
tccatgattt tcctgcagtt cctgattt                                      29

<210> SEQ ID NO 242
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 242
tccatgacgt tcctgcagtt cctgacgtt                                     29
```

```
<210> SEQ ID NO 243
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 243
ggcggcggcg gcggcggcgg                                           20

<210> SEQ ID NO 244
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 244
tccacgacgt tttcgacgtt                                           20

<210> SEQ ID NO 245
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 245
tcgtcgttgt cgttgtcgtt                                           20

<210> SEQ ID NO 246
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 246
tcgtcgtttt gtcgttttgt cgtt                                      24

<210> SEQ ID NO 247
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 247
tcgtcgttgt cgttttgtcg tt                                        22

<210> SEQ ID NO 248
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 248
gcgtgcgttg tcgttgtcgt t                                         21

<210> SEQ ID NO 249
<211> LENGTH: 19
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (6)...(6)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (15)...(15)
<223> OTHER INFORMATION: m5c

<400> SEQUENCE: 249
cnggcnggcn gggcnccgg                                                  19

<210> SEQ ID NO 250
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 250
gcggcgggcg gcgcgcgccc                                                 20

<210> SEQ ID NO 251
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (8)...(8)
<223> OTHER INFORMATION: I
<220> FEATURE:
<221> NAME/KEY: modified_base
<222> LOCATION: (14)...(14)
<223> OTHER INFORMATION: I

<400> SEQUENCE: 251
agncccgnga acgnattcac                                                 20

<210> SEQ ID NO 252
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 252
tgtcgtttgt cgtttgtcgt t                                               21

<210> SEQ ID NO 253
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 253
```

-continued

| tgtcgttgtc gttgtcgttg tcgtt | 25 |

```
<210> SEQ ID NO 254
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 254
```

| tgtcgttgtc gttgtcgttg tcgtt | 25 |

```
<210> SEQ ID NO 255
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 255
```

| tcgtcgtcgt cgtt | 14 |

```
<210> SEQ ID NO 256
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 256
```

| tgtcgttgtc gtt | 13 |

```
<210> SEQ ID NO 257
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 257
```

| cccccccccc cccccccccc | 20 |

```
<210> SEQ ID NO 258
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 258
```

| tctagcgttt ttagcgttcc | 20 |

```
<210> SEQ ID NO 259
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 259
```

| tgcatccccc aggccaccat | 20 |

```
<210> SEQ ID NO 260
<211> LENGTH: 23
<212> TYPE: DNA
<213> ORGANISM: Artificial Sequence
```

```
<220> FEATURE:
<223> OTHER INFORMATION: Synthetic Sequence

<400> SEQUENCE: 260
tcgtcgtcgt cgtcgtcgtc gtt                                          23

<210> SEQ ID NO 261
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 261
tcgtcgttgt cgttgtcgtt                                              20

<210> SEQ ID NO 262
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 262
tcgtcgtttt gtcgttttgt cgtt                                         24

<210> SEQ ID NO 263
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 263
tcgtcgttgt cgttttgtcg tt                                           22

<210> SEQ ID NO 264
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 264
ggggagggag gaacttctta aaattccccc agaatgttt                         39

<210> SEQ ID NO 265
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 265
aaacattctg ggggaatttt aagaagttcc tccctcccc                         39

<210> SEQ ID NO 266
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 266
atgtttactt cttaaaattc ccccagaatg ttt                               33
```

<210> SEQ ID NO 267
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 267
aaacattctg ggggaattttt aagaagtaaa cat                        33

<210> SEQ ID NO 268
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 268
atgtttacta gacaaaattc ccccagaatg ttt                         33

<210> SEQ ID NO 269
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 269
aaacattctg ggggaattttt gtctagtaaa cat                        33

<210> SEQ ID NO 270
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 270
aaaattgacg ttttaaaaaa                                        20

<210> SEQ ID NO 271
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 271 cccctttgacg ttttccccccc                                       20

<210> SEQ ID NO 272
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 272
ttttcgttgt ttttgtcgtt                                        20

<210> SEQ ID NO 273
<211> LENGTH: 24
<212> TYPE: DNA
<213> ORGANISM: Artificial Sequence
<220> FEATURE:
<223> OTHER INFORMATION: Synthetic Sequence

```
<400> SEQUENCE: 273
tcgtcgtttt gtcgttttgt cgtt                                            24

<210> SEQ ID NO 274
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 274
ctgcagcctg ggac                                                       14

<210> SEQ ID NO 275
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 275
acccgtcgta attatagtaa aaccc                                           25

<210> SEQ ID NO 276
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 276
ggtacctgtg gggacattgt g                                               21

<210> SEQ ID NO 277
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 277
agcaccgaac gtgagagg                                                   18

<210> SEQ ID NO 278
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 278
tccatgccgt tcctgccgtt                                                 20

<210> SEQ ID NO 279
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 279
tccatgacgg tcctgacggt                                                 20

<210> SEQ ID NO 280
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 280
tccatgccgg tcctgccggt                                          20

<210> SEQ ID NO 281
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 281
tccatgcgcg tcctgcgcgt                                          20

<210> SEQ ID NO 282
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 282
ctggtctttc tggttttttt ctgg                                     24

<210> SEQ ID NO 283
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 283 tcagggtgg ggggaacctt                                           20

<210> SEQ ID NO 284
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 284
tccatgangt tcctagttct                                          20

<210> SEQ ID NO 285
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 285
tccatgatgt tcctagttct                                          20

<210> SEQ ID NO 286
<211> LENGTH: 26
<212> TYPE: DNA
<213> ORGANISM: Artificial Sequence
```

```
<220> FEATURE:
<223> OTHER INFORMATION: Synthetic Sequence

<400> SEQUENCE: 286
cccgaagtca tttcctctta acctgg                                              26

<210> SEQ ID NO 287
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 287
ccaggttaag aggaaatgac ttcggg                                              26

<210> SEQ ID NO 288
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 288
tcctggnggg gaagt                                                          15

<210> SEQ ID NO 289
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (9)...(9)
<223> OTHER INFORMATION: m5c
<220> FEATURE:
<221> NAME/KEY: modified_base
<222> LOCATION: (12)...(12)
<223> OTHER INFORMATION: m5c
<220> FEATURE:
<221> NAME/KEY: modified_base
<222> LOCATION: (14)...(14)
<223> OTHER INFORMATION: m5c
<221> NAME/KEY: modified_base
<222> LOCATION: (16)...(16)
<223> OTHER INFORMATION: m5c
<220> FEATURE:
<223> OTHER INFORMATION: Synthetic Sequence

<400> SEQUENCE: 289
gnggngggng gngngngccc                                                     20

<210> SEQ ID NO 290
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 290
```

-continued tccatgtgct tcctgatgct                                          20

<210> SEQ ID NO 291
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 291
tccatgtcct tcctgatgct                                          20

<210> SEQ ID NO 292
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 292
tccatgtcgt tcctagttct                                          20

<210> SEQ ID NO 293
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 293
tccaagtagt tcctagttct                                          20

<210> SEQ ID NO 294
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 294
tccatgtagt tcctagttct                                          20

<210> SEQ ID NO 295
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 295
tcccgcgcgt tccgcgcgtt                                          20

<210> SEQ ID NO 296
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 296
tcctggcggt cctggcggtt                                          20

<210> SEQ ID NO 297
<211> LENGTH: 15
<212> TYPE: DNA

```
<213> ORGANISM: Artificial Sequence
<220> FEATURE:
<223> OTHER INFORMATION: Synthetic Sequence

<400> SEQUENCE: 297
tcctggaggg gaagt                                                    15

<210> SEQ ID NO 298
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 298
tcctgggggg gaagt                                                    15

<210> SEQ ID NO 299
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 299
tcctggtggg gaagt                                                    15

<210> SEQ ID NO 300
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 300
tcgtcgtttt gtcgttttgt cgtt                                          24

<210> SEQ ID NO 301
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 301
ctggtctttc tggttttttt ctgg                                          24

<210> SEQ ID NO 302
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 302
tccatgacgt tcctgacgtt                                               20

<210> SEQ ID NO 303
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 303
tccaggactt ctctcaggtt                                               20
```

<210> SEQ ID NO 304
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 304
tngtngtttt gtngttttgt ngtt                                        24

<210> SEQ ID NO 305
<211> LENGTH: 29
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 305
tcgtcgtttt gtcgttttgt cgtttttt                                    29

<210> SEQ ID NO 306
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 306
gctatgacgt tccaaggg                                               18

<210> SEQ ID NO 307
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 307 tcaacgtt                                                           8

<210> SEQ ID NO 308
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 308

-continued tccaggactt tcctcaggtt                                        20

<210> SEQ ID NO 309
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 309
ctctctgtag gcccgcttgg                                        20

<210> SEQ ID NO 310
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 310
ctttccgttg gacccctggg                                        20

<210> SEQ ID NO 311
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 311
gtccgggcca ggccaaagtc                                        20

<210> SEQ ID NO 312
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 312
gtgcgcgcga gcccgaaatc                                        20

<210> SEQ ID NO 313
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: I
<221> NAME/KEY: modified_base
<222> LOCATION: (17)...(17)
<223> OTHER INFORMATION: I
<220> FEATURE:
<223> OTHER INFORMATION: Synthetic Sequence

<400> SEQUENCE: 313
tccatgangt tcctgangtt                                        20

<210> SEQ ID NO 314
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 314

-continued aatagtcgcc ataacaaaac                                            20

<210> SEQ ID NO 315
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 315
aatagtcgcc atggcggggc                                            20

<210> SEQ ID NO 316
<211> LENGTH: 28
<212> TYPE: DNA
<213> ORGANISM: Artificial Sequence
<220> FEATURE:
<221> NAME/KEY: misc_difference
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 316
tttttccatg tcgttcctga tgcttttt                                   28

<210> SEQ ID NO 317
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 317
tcctgtcgtt gaagtttttt                                            20

<210> SEQ ID NO 318
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 318
gctagcttta gagctttaga gctt                                       24

<210> SEQ ID NO 319
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 319
tgctgcttcc cccccccccc                                            20

<210> SEQ ID NO 320
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 320
tcgacgttcc cccccccccc                                            20

```
<210> SEQ ID NO 321
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 321
tcgtcgttcc cccccccccc                                                   20

<210> SEQ ID NO 322
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 322
tcgtcgttcc cccccccccc                                                   20

<210> SEQ ID NO 323
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 323
tcgccgttcc cccccccccc                                                   20

<210> SEQ ID NO 324
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 324
tcgtcgatcc cccccccccc                                                   20

<210> SEQ ID NO 325
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 325
tcctgacgtt gaagt                                                        15

<210> SEQ ID NO 326
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 326
tcctgccgtt gaagt                                                        15

<210> SEQ ID NO 327
<211> LENGTH: 15
<212> TYPE: DNA
<213> ORGANISM: Artificial Sequence
<220> FEATURE:
<223> OTHER INFORMATION: Synthetic Sequence
```

```
<400> SEQUENCE: 327
tcctgacggt gaagt                                              15

<210> SEQ ID NO 328
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 328
tcctgagctt gaagt                                              15

<210> SEQ ID NO 329
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 329
tcctggcggg gaagt                                              15

<210> SEQ ID NO 330
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 330
aaaatctgtg cttttaaaaa a                                       21

<210> SEQ ID NO 331
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 331
gatccagtca cagtgacctg gcagaatctg gat                          33

<210> SEQ ID NO 332
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 332
gatccagatt ctgccaggtc actgtgactg gat                          33

<210> SEQ ID NO 333
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 333
gatccagtca cagtgactca gcagaatctg gat                          33

<210> SEQ ID NO 334
<211> LENGTH: 33
```

```
<212> TYPE: DNA
<213> ORGANISM: Artificial Sequence
<220> FEATURE:
<223> OTHER INFORMATION: Synthetic Sequence

<400> SEQUENCE: 334
gatccagatt ctgctgagtc actgtgactg gat                              33

<210> SEQ ID NO 335
<211> LENGTH: 20
<212> TYPE: DNA
<213> ORGANISM: Artificial Sequence
<220> FEATURE:
<221> NAME/KEY: modified_base
<222> LOCATION: (16)...(16)
<223> OTHER INFORMATION: m5c
<220> FEATURE:
<223> OTHER INFORMATION: Synthetic Sequence

<400> SEQUENCE: 335
tcgtcgttcc ccccncccc                                               20

<210> SEQ ID NO 336
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 336
tngtngttcc cccccccccc                                              20

<210> SEQ ID NO 337
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 337
tngtcgttcc cccccccccc                                              20

<210> SEQ ID NO 338
<211> LENGTH: 20
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 338
tcgtngttcc cccccccccc                                              20

<210> SEQ ID NO 339
<211> LENGTH: 20
```

<212> TYPE: DNA
<213> ORGANISM: Artificial Sequence
<220> FEATURE:
<223> OTHER INFORMATION: Synthetic Sequence

<400> SEQUENCE: 339
tcgtcgctcc cccccccccc                                          20

<210> SEQ ID NO 340
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 340
tcgtcggtcc cccccccccc                                          20

<210> SEQ ID NO 341
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 341
tcggcgttcc cccccccccc                                          20

<210> SEQ ID NO 342
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 342
ggccttttcc cccccccccc                                          20

<210> SEQ ID NO 343
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 343
tcgtcgtttt gacgttttgt cgtt                                     24

<210> SEQ ID NO 344
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 344
tcgtcgtttt gacgttttga cgtt                                     24

<210> SEQ ID NO 345
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 345
ccgtcgttcc cccccccccc                      20

<210> SEQ ID NO 346
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 346
gcgtcgttcc cccccccccc                      20

<210> SEQ ID NO 347
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 347
tcgtcattcc cccccccccc                      20

<210> SEQ ID NO 348
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 348
acgtcgttcc cccccccccc                      20

<210> SEQ ID NO 349
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 349
ctgtcgttcc cccccccccc                      20

<210> SEQ ID NO 350
<211> LENGTH: 24
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 350
tttttcgtcg ttcccccccc cccc                 24

<210> SEQ ID NO 351
<211> LENGTH: 20
<212> TYPE: DNA
<213> ORGANISM: Artificial Sequence
<220> FEATURE:
<221> NAME/KEY: misc_feature
<222> LOCATION: (18)...(20)
<223> OTHER INFORMATION: Biotin moiety attached at 3' end of sequence.
<220> FEATURE:
<223> OTHER INFORMATION: Synthetic Sequence

<400> SEQUENCE: 351
tcgtcgttcc cccccccccc                              20

<210> SEQ ID NO 352
<211> LENGTH: 24
<212> TYPE: DNA
<213> ORGANISM: Artificial Sequence
<220> FEATURE:
<221> NAME/KEY: misc_feature
<222> LOCATION: (22)...(24)
<223> OTHER INFORMATION: Biotin moiety attached at 3' end of sequence.
<220> FEATURE:
<223> OTHER INFORMATION: Synthetic Sequence

<400> SEQUENCE: 352
tcgtcgtttt gtcgttttgt cgtt                         24

<210> SEQ ID NO 353
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 353
tccagttcct tcctcagtct                              20

<210> SEQ ID NO 354
<211> LENGTH: 24
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 354
tngtcgtttt gtcgttttgt cgtt                         24

<210> SEQ ID NO 355
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 355
tcctggaggg gaagt                                   15

<210> SEQ ID NO 356
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 356
tcctgaaaag gaagt                                   15

<210> SEQ ID NO 357
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 357
tcgtcgttcc ccccccc                                          17

<210> SEQ ID NO 358
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 358
tngtngtttt gtngttttgt ngtt                                  24

<210> SEQ ID NO 359
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 359
ggggtcaagc ttgagggggg                                       20

<210> SEQ ID NO 360
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 360
tgctgcttcc cccccccccc                                       20

<210> SEQ ID NO 361
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 361
tcgtcgtcgt cgtt                                             14

<210> SEQ ID NO 362
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 362
tcgtcgtcgt cgtt                                             14

<210> SEQ ID NO 363
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 363
tcgtcgtcgt cgtt                                                    14

<210> SEQ ID NO 364
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 364
tcaacgttga                                                         10

<210> SEQ ID NO 365
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 365 tcaacgtt                                                            8

<210> SEQ ID NO 366
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 366
atagttttcc attttttac                                               20

<210> SEQ ID NO 367
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 367
aatagtcgcc atcgcgcgac                                              20

<210> SEQ ID NO 368
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 368
aatagtcgcc atcccgggac                                              20

<210> SEQ ID NO 369
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 369
aatagtcgcc atcccccccc                                                     20

<210> SEQ ID NO 370
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 370
tgctgctttt gtgcttttgt gctt                                                24

<210> SEQ ID NO 371
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 371
ctgtgctttc tgtgttttc tgtg                                                 24

<210> SEQ ID NO 372
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 372
ctaatctttc taattttttt ctaa                                                24

<210> SEQ ID NO 373
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 373
tcgtcgttgg tgtcgttggt gtcgtt                                              26

<210> SEQ ID NO 374
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 374
tcgtcgttgg ttgtcgtttt ggtt                                                24

<210> SEQ ID NO 375
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 375
accatggacg agctgtttcc cctc                                                24

```
<210> SEQ ID NO 376
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 376
tcgtcgtttt gcgtgcgttt                                            20

<210> SEQ ID NO 377
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 377
ctgtaagtga gcttggagag                                            20

<210> SEQ ID NO 378
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 378
gagaacgctg gaccttcc                                              18

<210> SEQ ID NO 379
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 379
cgggcgactc agtctatcgg                                            20

<210> SEQ ID NO 380
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 380
gttctcagat aaagcggaac cagcaacaga cacagaa                         37

<210> SEQ ID NO 381
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 381
ttctgtgtct gttgctggtt ccgctttatc tgagaac                         37

<210> SEQ ID NO 382
<211> LENGTH: 23
<212> TYPE: DNA
<213> ORGANISM: Artificial Sequence
<220> FEATURE:
<223> OTHER INFORMATION: Synthetic Sequence
```

```
<400> SEQUENCE: 382
cagacacaga agcccgatag acg                                      23

<210> SEQ ID NO 383
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 383
agacagacac gaaacgaccg                                          20

<210> SEQ ID NO 384
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 384
gtctgtccca tgatctcgaa                                          20

<210> SEQ ID NO 385
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 385
gctggccagc ttacctcccg                                          20

<210> SEQ ID NO 386
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 386
ggggcctcta tacaacctgg g                                        21

<210> SEQ ID NO 387
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 387
ggggtccctg agactgcc                                            18

<210> SEQ ID NO 388
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 388
gagaacgctg gaccttccat                                          20

<210> SEQ ID NO 389
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 389
tccatgtcgg tcctgatgct                                              20

<210> SEQ ID NO 390
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 390
ctcttgcgac ctggaaggta                                              20

<210> SEQ ID NO 391
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 391
aggtacagcc aggactacga                                              20

<210> SEQ ID NO 392
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 392
accatggacg acctgtttcc cctc                                         24

<210> SEQ ID NO 393
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 393
accatggatt accttttcc cctt                                          24

<210> SEQ ID NO 394
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 394
atggaaggtc cagcgttctc                                              20

<210> SEQ ID NO 395
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 395
```
agcatcagga ccgacatgga 20

<210> SEQ ID NO 396
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 396
ctctccaagc tcacttacag 20

<210> SEQ ID NO 397
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 397
tccctgagac tgccccacct t 21

<210> SEQ ID NO 398
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 398
gccaccaaaa cttgtccatg 20

<210> SEQ ID NO 399
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 399
gtccatggcg tgcgggatga 20

<210> SEQ ID NO 400
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 400
cctctataca acctgggac 19

<210> SEQ ID NO 401
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 401
cgggcgactc agtctatcgg 20

<210> SEQ ID NO 402
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 402
gcgctaccgg tagcctgagt                                                    20

<210> SEQ ID NO 403
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 403
cgactgccga acaggatatc ggtgatcagc actgg                                   35

<210> SEQ ID NO 404
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 404
ccagtgctga tcaccgatat cctgttcggc agtcg                                   35

<210> SEQ ID NO 405
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 405
ccaggttgta tagaggc                                                       17

<210> SEQ ID NO 406
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 406
tctcccagcg tacgccat                                                      18

<210> SEQ ID NO 407
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 407
tctcccagcg tgcgtttt                                                      18

<210> SEQ ID NO 408
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 408
tctcccgacg tgcgccat                                                      18
```

```
<210> SEQ ID NO 409
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 409
tctcccgtcg tgcgccat                                                       18

<210> SEQ ID NO 410
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 410
ataatcgtcg ttcaagcaag                                                     20

<210> SEQ ID NO 411
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 411
tcgtcgtttt gtcgttttgt cgt                                                 23

<210> SEQ ID NO 412
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 412
tcgtcgtttt gtcgttttgt cgtt                                                24

<210> SEQ ID NO 413
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 413
tcgtcgtttt gtcgttttgt cgtt                                                24

<210> SEQ ID NO 414
<211> LENGTH: 24
<212> TYPE: DNA
<213> ORGANISM: Artificial Sequence
<220> FEATURE:
<221> NAME/KEY: misc_difference
<222> LOCATION: (3)...(3)
<223> OTHER INFORMATION: n is a or c or g or t/u
<220> FEATURE:
<221> NAME/KEY: misc_difference
<222> LOCATION: (8)...(8)
<223> OTHER INFORMATION: n is a or c or g or t/u
<220> FEATURE:
<221> NAME/KEY: misc_difference
<222> LOCATION: (11)...(11)
<223> OTHER INFORMATION: n is a or c or g or t/u
<220> FEATURE:
<221> NAME/KEY: misc_difference
```

```
<222> LOCATION: (16)...(16)
<223> OTHER INFORMATION: n is a or c or g or t/u
<220> FEATURE:
<221> NAME/KEY: misc_difference
<222> LOCATION: (19)...(19)
<223> OTHER INFORMATION: n is a or c or g or t/u
<221> NAME/KEY: misc_difference
<222> LOCATION: (24)...(24)
<223> OTHER INFORMATION: n is a or c or g or t/u
<220> FEATURE:
<223> OTHER INFORMATION: Synthetic Sequence

<400> SEQUENCE: 414
tcntcgtntt ntcgtnttnt cgtn                                        24

<210> SEQ ID NO 415
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 415
tctcccagcg tcgccat                                                17

<210> SEQ ID NO 416
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 416
tctcccatcg tcgccat                                                17

<210> SEQ ID NO 417
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 417
ataatcgtgc gttcaagaaa g                                           21

<210> SEQ ID NO 418
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 418
ataatcgacg ttcccccccc                                             20

<210> SEQ ID NO 419
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 419
tctatcgacg ttcaagcaag                                             20

<210> SEQ ID NO 420
<211> LENGTH: 14
```

```
<212> TYPE: DNA
<213> ORGANISM: Artificial Sequence
<220> FEATURE:
<223> OTHER INFORMATION: Synthetic Sequence

<400> SEQUENCE: 420
tcctgacggg gagt                                                      14

<210> SEQ ID NO 421
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 421
tccatgacgt tcctgatcc                                                 19

<210> SEQ ID NO 422
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 422
tccatgacgt tcctgatcc                                                 19

<210> SEQ ID NO 423
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 423
tccatgacgt tcctgatcc                                                 19

<210> SEQ ID NO 424
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 424
tcctggcgtg gaagt                                                     15

<210> SEQ ID NO 425
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 425
tccatgacgt tcctgatcc                                                 19

<210> SEQ ID NO 426
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 426
```
tcgtcgctgt tgtcgtttct t                                    21

<210> SEQ ID NO 427
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 427
agcagcttta gagctttaga gctt                                 24

<210> SEQ ID NO 428
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 428
cccccccccc cccccccccc cccc                                 24

<210> SEQ ID NO 429
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 429
tcgtcgtttt gtcgttttgt cgttttgtcg tt                        32

<210> SEQ ID NO 430
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 430
tcgtcgtttt ttgtcgtttt ttgtcgtt                             28

<210> SEQ ID NO 431
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 431
tcgtcgtttt tttttttttt                                      20

<210> SEQ ID NO 432
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 432
tttttcaacg ttgatttttt                                      20

<210> SEQ ID NO 433
<211> LENGTH: 24
<212> TYPE: DNA
<213> ORGANISM: Artificial Sequence

```
<220> FEATURE:
<223> OTHER INFORMATION: Synthetic Sequence

<400> SEQUENCE: 433
tttttttttt tttttttttt tttt                                              24

<210> SEQ ID NO 434
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 434
ggggtcgtcg ttttggggggg                                                  20

<210> SEQ ID NO 435
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 435
tcgtcgtttt gtcgttttgg gggg                                              24

<210> SEQ ID NO 436
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 436
tcgtcgctgt ctccgcttct tcttgcc                                           27

<210> SEQ ID NO 437
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 437
tcgtcgctgt ctccg                                                        15

<210> SEQ ID NO 438
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 438
ctgtaagtga gcttggagag                                                   20

<210> SEQ ID NO 439
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 439
gagaacgctg gaccttccat                                                   20
```

```
<210> SEQ ID NO 440
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 440
ccaggttgta tagaggc                                              17

<210> SEQ ID NO 441
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 441
gctagacgtt agcgtga                                              17

<210> SEQ ID NO 442
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 442
ggagctcttc gaacgccata                                           20

<210> SEQ ID NO 443
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 443
tctccatgat ggttttatcg                                           20

<210> SEQ ID NO 444
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 444
aaggtggggc agtctcaggg a                                         21

<210> SEQ ID NO 445
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 445
atcggaggac tggcgcgccg                                           20

<210> SEQ ID NO 446
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 446
ttaggacaag gtctagggtg                                          20

<210> SEQ ID NO 447
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 447
accacaacga gaggaacgca                                          20

<210> SEQ ID NO 448
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 448
ggcagtgcag gctcaccggg                                          20

<210> SEQ ID NO 449
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 449
gaaccttcca tgctgtt                                             17

<210> SEQ ID NO 450
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 450
gctagacgtt agcgtga                                             17

<210> SEQ ID NO 451
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 451
gcttggaggg cctgtaagtg                                          20

<210> SEQ ID NO 452
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 452
gtagccttcc ta                                                  12

<210> SEQ ID NO 453
```

```
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 453
cggtagcctt ccta                                                        14

<210> SEQ ID NO 454
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 454
cacggtagcc ttccta                                                      16

<210> SEQ ID NO 455
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 455
agcacggtag ccttccta                                                    18

<210> SEQ ID NO 456
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 456
gaacgctgga ccttccat                                                    18

<210> SEQ ID NO 457
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 457
gaccttccat                                                             10

<210> SEQ ID NO 458
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 458
tggaccttcc at                                                          12

<210> SEQ ID NO 459
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 459
```

```
gctggacctt ccat                                                    14

<210> SEQ ID NO 460
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 460
acgctggacc ttccat                                                  16

<210> SEQ ID NO 461
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 461
taagctctgt caacgccagg                                              20

<210> SEQ ID NO 462
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 462
gagaacgctg gaccttccat gt                                           22

<210> SEQ ID NO 463
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 463
tccatgtcgg tcctgatgct                                              20

<210> SEQ ID NO 464
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 464
ttcatgcctt gcaaaatggc g                                            21

<210> SEQ ID NO 465
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 465
tgctagctgt gcctgtacct                                              20

<210> SEQ ID NO 466
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 466
agcatcagga ccgacatgga                                               20

<210> SEQ ID NO 467
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 467
gaccttccat gtcggtcctg at                                            22

<210> SEQ ID NO 468
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 468
acaaccacga gaacgggaac                                               20

<210> SEQ ID NO 469
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 469
gaaccttcca tgctgttccg                                               20

<210> SEQ ID NO 470
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 470
caatcaatct gaggagaccc                                               20

<210> SEQ ID NO 471
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 471
tcagctctgg tactttttca                                               20

<210> SEQ ID NO 472
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 472
tggttacggt ctgtcccatg                                               20
```

```
<210> SEQ ID NO 473
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 473
gtctatcgga ggactggcgc                                              20

<210> SEQ ID NO 474
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 474
cattttacgg gcgggcgggc                                              20

<210> SEQ ID NO 475
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 475
gaggggacca ttttacgggc                                              20

<210> SEQ ID NO 476
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 476
tgtccagccg aggggaccat                                              20

<210> SEQ ID NO 477
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 477
cgggcttacg gcggatgctg                                              20

<210> SEQ ID NO 478
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 478
tggaccttct atgtcggtcc                                              20

<210> SEQ ID NO 479
<211> LENGTH: 20
<212> TYPE: DNA
<213> ORGANISM: Artificial Sequence
<220> FEATURE:
```

-continued

<223> OTHER INFORMATION: Synthetic Sequence

<400> SEQUENCE: 479
tgtcccatgt ttttagaagc  20

<210> SEQ ID NO 480
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 480
gtggttacgg tcgtgcccat  20

<210> SEQ ID NO 481
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 481
cctccaaatg aaagaccccc  20

<210> SEQ ID NO 482
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 482
ttgtactctc catgatggtt  20

<210> SEQ ID NO 483
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 483
ttccatgctg ttccggctgg  20

<210> SEQ ID NO 484
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 484
gaccttctat gtcggtcctg  20

<210> SEQ ID NO 485
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 485
gagaccgctc gaccttcgat  20

```
<210> SEQ ID NO 486
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 486
ttgccccata ttttagaaac                                               20

<210> SEQ ID NO 487
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 487
ttgaaactga ggtgggac                                                 18

<210> SEQ ID NO 488
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 488
ctatcggagg actggcgcgc c                                             21

<210> SEQ ID NO 489
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 489
cttggagggc ctcccggcgg                                               20

<210> SEQ ID NO 490
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 490
gctgaacctt ccatgctgtt                                               20

<210> SEQ ID NO 491
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 491
tagaaacagc attcttcttt tagggcagca ca                                 32

<210> SEQ ID NO 492
<211> LENGTH: 24
<212> TYPE: DNA
<213> ORGANISM: Artificial Sequence
<220> FEATURE:
<223> OTHER INFORMATION: Synthetic Sequence
```

```
<400> SEQUENCE: 492
agatggttct cagataaagc ggaa                                          24

<210> SEQ ID NO 493
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 493
ttccgcttta tctgagaacc atct                                          24

<210> SEQ ID NO 494
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 494
gtcccaggtt gtatagaggc tgc                                           23

<210> SEQ ID NO 495
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 495
gcgccagtcc tccgatagac                                               20

<210> SEQ ID NO 496
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 496
atcggaggac tggcgcgccg                                               20

<210> SEQ ID NO 497
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 497
ggtctgtccc atatttttag                                               20

<210> SEQ ID NO 498
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 498
tttttcaacg ttgagggggg                                               20

<210> SEQ ID NO 499
<211> LENGTH: 21
```

```
<212> TYPE: DNA
<213> ORGANISM: Artificial Sequence
<220> FEATURE:
<223> OTHER INFORMATION: Synthetic Sequence

<400> SEQUENCE: 499
tttttcaagc gttgattttt t                                              21

<210> SEQ ID NO 500
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 500
ggggtcaacg ttgattttt                                                 20

<210> SEQ ID NO 501
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 501
ggggttttca acgttttgag ggggg                                          25

<210> SEQ ID NO 502
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 502
ggttacggtc tgtcccatat                                                20

<210> SEQ ID NO 503
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 503
ctgtcccata tttttagaca                                                20

<210> SEQ ID NO 504
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 504
accatcctga ggccattcgg                                                20

<210> SEQ ID NO 505
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 505
```

```
cgtctatcgg gcttctgtgt ctg                                    23

<210> SEQ ID NO 506
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 506
ggccatccca cattgaaagt t                                      21

<210> SEQ ID NO 507
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 507
ccaaatatcg gtggtcaagc ac                                     22

<210> SEQ ID NO 508
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 508
gtgcttgacc accgatattt gg                                     22

<210> SEQ ID NO 509
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 509
gtgctgatca ccgatatcct gttcgg                                 26

<210> SEQ ID NO 510
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 510
ggccaacttt caatgtggga tggcctc                                27

<210> SEQ ID NO 511
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 511
ttccgccgaa tggcctcagg atggtac                                27

<210> SEQ ID NO 512
<211> LENGTH: 36
<212> TYPE: DNA
<213> ORGANISM: Artificial Sequence
```

```
<220> FEATURE:
<223> OTHER INFORMATION: Synthetic Sequence

<400> SEQUENCE: 512
tatagtccct gagactgccc caccttctca acaacc                              36

<210> SEQ ID NO 513
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 513
gcagcctcta tacaacctgg gacggga                                        27

<210> SEQ ID NO 514
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 514
ctatcggagg actggcgcgc cg                                             22

<210> SEQ ID NO 515
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 515
tatcggagga ctggcgcgcc g                                              21

<210> SEQ ID NO 516
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 516
gatcggagga ctggcgcgcc g                                              21

<210> SEQ ID NO 517
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 517
ccgaacagga tatcggtgat cagcac                                         26

<210> SEQ ID NO 518
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 518
ttttggggtc aacgttgagg gggg                                           24
```

-continued

<210> SEQ ID NO 519
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 519
ggggtcaacg ttgagggggg                    20

<210> SEQ ID NO 520
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 520
cgcgcgcgcg cgcgcgcgcg                    20

<210> SEQ ID NO 521
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 521
ggggcatgac gttcggggggg                   20

<210> SEQ ID NO 522
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 522
ggggcatgac gttcaaaaaa                    20

<210> SEQ ID NO 523
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 523
ggggcatgag cttcggggggg                   20

<210> SEQ ID NO 524
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 524
ggggcatgac gttcggggggg                   20

<210> SEQ ID NO 525
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 525
aaaacatgac gttcaaaaaa                                              20

<210> SEQ ID NO 526
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 526
aaaacatgac gttcggggggg                                             20

<210> SEQ ID NO 527
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 527
ggggcatgac gttcaaaaaa                                              20

<210> SEQ ID NO 528
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 528
accatggacg atctgtttcc cctc                                         24

<210> SEQ ID NO 529
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 529
gccatggacg aactgttccc cctc                                         24

<210> SEQ ID NO 530
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 530
cccccccccc cccccccccc                                              20

<210> SEQ ID NO 531
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 531
gggggggggg gggggggggg                                              20

<210> SEQ ID NO 532

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 532
gctgtaaaat gaatcggccg                                                  20

<210> SEQ ID NO 533
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 533
ttcgggcgga ctcctccatt                                                  20

<210> SEQ ID NO 534
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 534
tatgccgcgc ccggacttat                                                  20

<210> SEQ ID NO 535
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 535
ggggtaatcg atcagggggg                                                  20

<210> SEQ ID NO 536
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 536
tttgagaacg ctggaccttc                                                  20

<210> SEQ ID NO 537
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 537
gatcgctgat ctaatgctcg                                                  20

<210> SEQ ID NO 538
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 538
```
gtcggtcctg atgctgttcc					20

<210> SEQ ID NO 539
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 539
tcgtcgtcag ttcgctgtcg					20

<210> SEQ ID NO 540
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 540
ctggaccttc catgtcgg					18

<210> SEQ ID NO 541
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 541
gctcgttcag cgcgtct					17

<210> SEQ ID NO 542
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 542
ctggaccttc catgtc					16

<210> SEQ ID NO 543
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 543
cactgtcctt cgtcga					16

<210> SEQ ID NO 544
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 544
cgctggacct tccatgtcgg					20

<210> SEQ ID NO 545
<211> LENGTH: 20
<212> TYPE: DNA

```
<213> ORGANISM: Artificial Sequence
<220> FEATURE:
<223> OTHER INFORMATION: Synthetic Sequence

<400> SEQUENCE: 545
gctgagctca tgccgtctgc                                                20

<210> SEQ ID NO 546
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 546
aacgctggac cttccatgtc                                                20

<210> SEQ ID NO 547
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 547
tgcatgccgt acacagctct                                                20

<210> SEQ ID NO 548
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 548
ccttccatgt cggtcctgat                                                20

<210> SEQ ID NO 549
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 549
tactcttcgg atcccttgcg                                                20

<210> SEQ ID NO 550
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 550
ttccatgtcg gtcctgat                                                  18

<210> SEQ ID NO 551
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 551
ctgattgctc tctcgtga                                                  18
```

```
<210> SEQ ID NO 552
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 552
ggcgttattc ctgactcgcc                                                    20

<210> SEQ ID NO 553
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 553
cctacgttgt atgcgcccag ct                                                 22

<210> SEQ ID NO 554
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 554
ggggtaatcg atgaggggg                                                     20

<210> SEQ ID NO 555
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 555
ttcgggcgga ctcctccatt                                                    20

<210> SEQ ID NO 556
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 556
tttttttttt tttttttttt                                                    20

<210> SEQ ID NO 557
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 557
gggggttttt tttttggggg                                                    20

<210> SEQ ID NO 558
<211> LENGTH: 20
<212> TYPE: DNA
<213> ORGANISM: Artificial Sequence
<220> FEATURE:
```

<223> OTHER INFORMATION: Synthetic Sequence

<400> SEQUENCE: 558
tttttggggg ggggttttt                                              20

<210> SEQ ID NO 559
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 559
gggggggggg ggggggggt                                              19

<210> SEQ ID NO 560
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 560
aaaaaaaaaa aaaaaaaaaa                                             20

<210> SEQ ID NO 561
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 561
cccccaaaaa aaaaccccc                                              20

<210> SEQ ID NO 562
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 562
aaaaaccccc cccccaaaaa                                             20

<210> SEQ ID NO 563
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 563
tttgaattca ggactggtga ggttgag                                     27

<210> SEQ ID NO 564
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 564
tttgaatcct cagcggtctc cagtggc                                     27

```
<210> SEQ ID NO 565
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 565
aattctctat cggggcttct gtgtctgttg ctggttccgc tttat            45

<210> SEQ ID NO 566
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 566
ctagataaag cggaaccagc aacagacaca gaagccccga tagag            45

<210> SEQ ID NO 567
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 567
ttttctagag aggtgcacaa tgctctgg                               28

<210> SEQ ID NO 568
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 568
tttgaattcc gtgtacagaa gcgagaagc                              29

<210> SEQ ID NO 569
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 569
tttgcggccg ctagacttaa cctgagagat a                           31

<210> SEQ ID NO 570
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 570
tttgggccca cgagagacag agacacttc                              29

<210> SEQ ID NO 571
<211> LENGTH: 29
<212> TYPE: DNA
<213> ORGANISM: Artificial Sequence
<220> FEATURE:
<223> OTHER INFORMATION: Synthetic Sequence
```

<400> SEQUENCE: 571
tttgggcccg cttctcgctt ctgtacacg					29

<210> SEQ ID NO 572
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 572
gagaacgctg gaccttccat					20

<210> SEQ ID NO 573
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 573
tccatgtcgg tcctgatgct					20

<210> SEQ ID NO 574
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 574 ctgtcg					6

<210> SEQ ID NO 575
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 575 tcgtga					6

<210> SEQ ID NO 576
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 576 cgtcga					6

<210> SEQ ID NO 577
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 577 agtgct					6

<210> SEQ ID NO 578
<211> LENGTH: 6

```
<212> TYPE: DNA
<213> ORGANISM: Artificial Sequence
<220> FEATURE:
<223> OTHER INFORMATION: Synthetic Sequence

<400> SEQUENCE: 578 ctgtcg                                                                      6

<210> SEQ ID NO 579
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 579 agtgct                                                                      6

<210> SEQ ID NO 580
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 580 cgtcga                                                                      6

<210> SEQ ID NO 581
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 581 tcgtga                                                                      6

<210> SEQ ID NO 582
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 582
gagaacgctc cagcttcgat                                                      20

<210> SEQ ID NO 583
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 583
gctagacgta agcgtga                                                         17

<210> SEQ ID NO 584
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 584
```

-continued gagaacgctc gaccttccat                                           20

<210> SEQ ID NO 585
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 585
gagaacgctg gacctatcca t                                         21

<210> SEQ ID NO 586
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 586
gctagaggtt agcgtga                                              17

<210> SEQ ID NO 587
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 587
gagaacgctg gacttccat                                            19

<210> SEQ ID NO 588
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 588
tcacgctaac gtctagc                                              17

<210> SEQ ID NO 589
<211> LENGTH: 17
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 589
gctagacgtt agcgtga                                              17

<210> SEQ ID NO 590
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 590
atggaaggtc gagcgttctc                                           20

```
<210> SEQ ID NO 591
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 591
gagaacgctg gaccttcgat                                               20

<210> SEQ ID NO 592
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 592
gagaacgatg gaccttccat                                               20

<210> SEQ ID NO 593
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 593
gagaacgctg gatccat                                                  17

<210> SEQ ID NO 594
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 594
gagaacgctc cagcactgat                                               20

<210> SEQ ID NO 595
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 595
tccatgtcgg tcctgctgat                                               20

<210> SEQ ID NO 596
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 596
atgtcctcgg tcctgatgct                                               20

<210> SEQ ID NO 597
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 597
gagaacgctc caccttccat                                                    20

<210> SEQ ID NO 598
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 598
gagaacgctg gaccttcgta                                                    20

<210> SEQ ID NO 599
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 599
atggaaggtc cagcgttctc                                                    20

<210> SEQ ID NO 600
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 600 tcctga                                                                    6

<210> SEQ ID NO 601
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 601 tcaacgtt                                                                  8

<210> SEQ ID NO 602
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 602 aacgtt                                                                    6

<210> SEQ ID NO 603
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 603 aacgttga                                                                  8

<210> SEQ ID NO 604
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 604
tcacgctaac ctctagc                                                    17

<210> SEQ ID NO 605
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 605
gagaacgctg gaccttgcat                                                 20

<210> SEQ ID NO 606
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 606
gctggacctt ccat                                                       14

<210> SEQ ID NO 607
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 607
gagaacgctg gacctcatcc at                                              22

<210> SEQ ID NO 608
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 608
gagaacgctg gacgctcatc cat                                             23

<210> SEQ ID NO 609
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 609
aacgttgagg ggcat                                                      15

<210> SEQ ID NO 610
<211> LENGTH: 15
<212> TYPE: DNA
<213> ORGANISM: Artificial Sequence
<220> FEATURE:

```
<223> OTHER INFORMATION: Synthetic Sequence

<400> SEQUENCE: 610
atgcccctca acgtt                                                    15

<210> SEQ ID NO 611
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 611
tcaacgttga                                                          10

<210> SEQ ID NO 612
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 612
gctggacctt ccat                                                     14

<210> SEQ ID NO 613
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 613 caacgtt                                                              7

<210> SEQ ID NO 614
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 614
acaacgttga                                                          10

<210> SEQ ID NO 615
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 615 tcacgt                                                               6

<210> SEQ ID NO 616
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 616 tcaagctt                                                             8
```

```
<210> SEQ ID NO 617
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 617 tcgtca                                                                    6

<210> SEQ ID NO 618
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 618 aggatatc                                                                  8

<210> SEQ ID NO 619
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 619 tagacgtc                                                                  8

<210> SEQ ID NO 620
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 620 gacgtcat                                                                  8

<210> SEQ ID NO 621
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 621 ccatcgat                                                                  8

<210> SEQ ID NO 622
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 622 atcgatgt                                                                  8

<210> SEQ ID NO 623
<211> LENGTH: 8
<212> TYPE: DNA
<213> ORGANISM: Artificial Sequence
<220> FEATURE:
<223> OTHER INFORMATION: Synthetic Sequence
```

```
<400> SEQUENCE: 623 atgcatgt                                                              8

<210> SEQ ID NO 624
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 624 ccatgcat                                                              8

<210> SEQ ID NO 625
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 625 agcgctga                                                              8

<210> SEQ ID NO 626
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 626 tcagcgct                                                              8

<210> SEQ ID NO 627
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 627 ccttcgat                                                              8

<210> SEQ ID NO 628
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 628
gtgccggggt ctccgggc                                                  18

<210> SEQ ID NO 629
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 629
gctgtggggc ggctcctg                                                  18

<210> SEQ ID NO 630
<211> LENGTH: 8
```

```
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 630 tcaacgtt                                                              8

<210> SEQ ID NO 631
<211> LENGTH: 8
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to FITC moiety.
<220> FEATURE:
<223> OTHER INFORMATION: Synthetic Sequence

<400> SEQUENCE: 631 tcaacgtt                                                              8

<210> SEQ ID NO 632
<211> LENGTH: 8
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to FITC moiety.
<220> FEATURE:
<223> OTHER INFORMATION: Synthetic Sequence

<400> SEQUENCE: 632 aacgttga                                                              8

<210> SEQ ID NO 633
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 633 tcaacgt                                                               7

<210> SEQ ID NO 634
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 634 aacgttg                                                               7

<210> SEQ ID NO 635
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 635
```

```
cgacga                                                                     6
```

<210> SEQ ID NO 636
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 636

```
tcaacgtt                                                                   8
```

<210> SEQ ID NO 637
<211> LENGTH: 5
<212> TYPE: DNA
<213> ORGANISM: Artificial Sequence
<220> FEATURE:
<223> OTHER INFORMATION: Synthetic Sequence

<400> SEQUENCE: 637

```
tcgga                                                                      5
```

<210> SEQ ID NO 638
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 638

```
agaacgtt                                                                   8
```

<210> SEQ ID NO 639
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 639

```
tcatcgat                                                                   8
```

<210> SEQ ID NO 640
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 640

```
taaacgtt                                                                   8
```

<210> SEQ ID NO 641
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 641

```
ccaacgtt                                                                   8
```

<210> SEQ ID NO 642
<211> LENGTH: 6
<212> TYPE: DNA
<213> ORGANISM: Artificial Sequence

```
<220> FEATURE:
<223> OTHER INFORMATION: Synthetic Sequence

<400> SEQUENCE: 642 gctcga                                                                    6

<210> SEQ ID NO 643
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 643 cgacgt                                                                    6

<210> SEQ ID NO 644
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 644 cgtcgt                                                                    6

<210> SEQ ID NO 645
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 645 acgtgt                                                                    6

<210> SEQ ID NO 646
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 646 cgttcg                                                                    6

<210> SEQ ID NO 647
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 647
gagcaagctg gaccttccat                                                    20

<210> SEQ ID NO 648
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 648 cgcgta                                                                    6
```

```
<210> SEQ ID NO 649
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 649 cgtacg                                                                      6

<210> SEQ ID NO 650
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 650 tcaccggt                                                                    8

<210> SEQ ID NO 651
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 651
caagagatgc taacaatgca                                                      20

<210> SEQ ID NO 652
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 652
acccatcaat agctctgtgc                                                      20

<210> SEQ ID NO 653
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 653 ccatcgat                                                                    8

<210> SEQ ID NO 654
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 654 tcgacgtc                                                                    8

<210> SEQ ID NO 655
<211> LENGTH: 8
<212> TYPE: DNA
<213> ORGANISM: Artificial Sequence
<220> FEATURE:
<223> OTHER INFORMATION: Synthetic Sequence
```

<400> SEQUENCE: 655 ctagcgct                                                                    8

<210> SEQ ID NO 656
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 656 taagcgct                                                                    8

<210> SEQ ID NO 657
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 657
tcgcgaattc gcg                                                             13

<210> SEQ ID NO 658
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 658
atggaaggtc cagcgttct                                                       19

<210> SEQ ID NO 659
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 659
actggacgtt agcgtga                                                         17

<210> SEQ ID NO 660
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 660
cgcctggggc tggtctgg                                                        18

<210> SEQ ID NO 661
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 661
gtgtcggggt ctccgggc                                                        18

<210> SEQ ID NO 662

```
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 662
gtgccggggt ctccgggc                                                    18

<210> SEQ ID NO 663
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 663
cgccgtcgcg gcggttgg                                                    18

<210> SEQ ID NO 664
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 664
gaagttcacg ttgaggggca t                                                21

<210> SEQ ID NO 665
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 665
atctggtgag ggcaagctat g                                                21

<210> SEQ ID NO 666
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 666
gttgaaaccc gagaacatca t                                                21

<210> SEQ ID NO 667
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 667 gcaacgtt                                                                8

<210> SEQ ID NO 668
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 668
```

```
gtaacgtt                                                        8

<210> SEQ ID NO 669
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 669 cgaacgtt                                                        8

<210> SEQ ID NO 670
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 670 gaaacgtt                                                        8

<210> SEQ ID NO 671
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 671 caaacgtt                                                        8

<210> SEQ ID NO 672
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 672 ctaacgtt                                                        8

<210> SEQ ID NO 673
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 673 ggaacgtt                                                        8

<210> SEQ ID NO 674
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 674 tgaacgtt                                                        8

<210> SEQ ID NO 675
<211> LENGTH: 8
<212> TYPE: DNA
```

```
<213> ORGANISM: Artificial Sequence
<220> FEATURE:
<223> OTHER INFORMATION: Synthetic Sequence

<400> SEQUENCE: 675 acaacgtt                                                                      8

<210> SEQ ID NO 676
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 676 ttaacgtt                                                                      8

<210> SEQ ID NO 677
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 677 aaaacgtt                                                                      8

<210> SEQ ID NO 678
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 678 ataacgtt                                                                      8

<210> SEQ ID NO 679
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 679 aacgttct                                                                      8

<210> SEQ ID NO 680
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 680 tccgatcg                                                                      8

<210> SEQ ID NO 681
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 681 tccgtacg                                                                      8
```

```
<210> SEQ ID NO 682
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 682
gctagacgct agcgtga                                                  17

<210> SEQ ID NO 683
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 683
gagaacgctg gacctcatca tccat                                         25

<210> SEQ ID NO 684
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 684
gagaacgcta gaccttctat                                               20

<210> SEQ ID NO 685
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 685
actagacgtt agtgtga                                                  17

<210> SEQ ID NO 686
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 686
cacaccttgg tcaatgtcac gt                                            22

<210> SEQ ID NO 687
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 687
tctccatcct atggttttat cg                                            22

<210> SEQ ID NO 688
<211> LENGTH: 15
<212> TYPE: DNA
<213> ORGANISM: Artificial Sequence
<220> FEATURE:
```

<223> OTHER INFORMATION: Synthetic Sequence

<400> SEQUENCE: 688
cgctggacct tccat                                                        15

<210> SEQ ID NO 689
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 689
caccaccttg gtcaatgtca cgt                                               23

<210> SEQ ID NO 690
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 690
gctagacgtt agctgga                                                      17

<210> SEQ ID NO 691
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 691
agtgcgattg cagatcg                                                      17

<210> SEQ ID NO 692
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 692
ttttcgtttt gtggttttgt ggtt                                              24

<210> SEQ ID NO 693
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 693
ttttcgtttg tcgttttgtc gtt                                               23

<210> SEQ ID NO 694
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 694
tttttgtttt gtggttttgt ggtt                                              24

```
<210> SEQ ID NO 695
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 695
accgcatgga ttctaggcca                                               20

<210> SEQ ID NO 696
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 696
gctagacgtt agcgt                                                    15

<210> SEQ ID NO 697
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 697
aacgctggac cttccat                                                  17

<210> SEQ ID NO 698
<211> LENGTH: 8
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 698 tcaangtt                                                             8

<210> SEQ ID NO 699
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 699 ccttcgat                                                             8

<210> SEQ ID NO 700
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 700
actagacgtt agtgtga                                                  17

<210> SEQ ID NO 701
<211> LENGTH: 17
<212> TYPE: DNA
```

```
<213> ORGANISM: Artificial Sequence
<220> FEATURE:
<223> OTHER INFORMATION: Synthetic Sequence

<400> SEQUENCE: 701
gctagaggtt agcgtga                                                  17

<210> SEQ ID NO 702
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 702
atggactctc cagcgttctc                                               20

<210> SEQ ID NO 703
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 703
atcgactctc gagcgttctc                                               20

<210> SEQ ID NO 704
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 704
gctagacgtt agc                                                      13

<210> SEQ ID NO 705
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 705 gctagacgt                                                            9

<210> SEQ ID NO 706
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 706
agtgcgattc gagatcg                                                  17

<210> SEQ ID NO 707
<211> LENGTH: 8
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence
```

```
<400> SEQUENCE: 707 tcagngct                                                                        8

<210> SEQ ID NO 708
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 708
ctgattgctc tctcgtga                                                             18

<210> SEQ ID NO 709
<211> LENGTH: 8
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 709 tnaacgtt                                                                        8

<210> SEQ ID NO 710
<211> LENGTH: 20
<212> TYPE: DNA
<213> ORGANISM: Artificial Sequence
<220> FEATURE:
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 710
gagaangctg gaccttccat                                                           20

<210> SEQ ID NO 711
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 711
gctagacgtt aggctga                                                              17

<210> SEQ ID NO 712
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 712
gctacttagc gtga                                                                 14

<210> SEQ ID NO 713
<211> LENGTH: 15
<212> TYPE: DNA
<213> ORGANISM: Artificial Sequence
<220> FEATURE:
```

<223> OTHER INFORMATION: Synthetic Sequence

<400> SEQUENCE: 713
gctaccttag cgtga                                                        15

<210> SEQ ID NO 714
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 714
atcgacttcg agcgttctc                                                    19

<210> SEQ ID NO 715
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 715
atgcactctg cagcgttctc                                                   20

<210> SEQ ID NO 716
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 716
agtgactctc cagcgttctc                                                   20

<210> SEQ ID NO 717
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 717
gccagatgtt agctgga                                                      17

<210> SEQ ID NO 718
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 718
atcgactcga gcgttctc                                                     18

<210> SEQ ID NO 719
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 719
atcgatcgag cgttctc                                                      17

```
<210> SEQ ID NO 720
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 720
gagaacgctc gaccttcgat                                               20

<210> SEQ ID NO 721
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 721
gctagacgtt agctgga                                                  17

<210> SEQ ID NO 722
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 722
atcgactctc gagcgttctc                                               20

<210> SEQ ID NO 723
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 723
tagacgttag cgtga                                                    15

<210> SEQ ID NO 724
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 724
cgactctcga gcgttctc                                                 18

<210> SEQ ID NO 725
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 725
ggggtcgacc ttggaggggg g                                             21

<210> SEQ ID NO 726
<211> LENGTH: 16
<212> TYPE: DNA
```

<213> ORGANISM: Artificial Sequence
<220> FEATURE:
<223> OTHER INFORMATION: Synthetic Sequence

<400> SEQUENCE: 726
gctaacgtta gcgtga                                                    16

<210> SEQ ID NO 727
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 727 cgtcgtcgt                                                             9

<210> SEQ ID NO 728
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<220> FEATURE:
<223> OTHER INFORMATION: Synthetic Sequence

<400> SEQUENCE: 728
gagaacgctg gacnttccat                                                20

<210> SEQ ID NO 729
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<220> FEATURE:
<223> OTHER INFORMATION: Synthetic Sequence

<400> SEQUENCE: 729
atcgacctac gtgcgttntc                                                20

<210> SEQ ID NO 730
<211> LENGTH: 20
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<220> FEATURE:
<223> OTHER INFORMATION: Synthetic Sequence

<400> SEQUENCE: 730
atngacctac gtgcgttctc                                                20

<210> SEQ ID NO 731
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 731
gctagangtt agcgt                                                            15

<210> SEQ ID NO 732
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<220> FEATURE:
<223> OTHER INFORMATION: Synthetic Sequence

<400> SEQUENCE: 732
atcgactctc gagngttctc                                                       20

<210> SEQ ID NO 733
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 733
ggggtaatgc atcagggggg                                                       20

<210> SEQ ID NO 734
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 734
ggctgtattc ctgactgccc                                                       20

<210> SEQ ID NO 735
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 735
ccatgctaac ctctagc                                                          17

<210> SEQ ID NO 736
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 736
gctagatgtt agcgtga                                                          17

<210> SEQ ID NO 737
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 737

```
cgtaccttac ggtga                                                    15

<210> SEQ ID NO 738
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 738
tccatgctgg tcctgatgct                                               20

<210> SEQ ID NO 739
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 739
atcgactctc tcgagcgttc tc                                            22

<210> SEQ ID NO 740
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 740
gctagagctt agcgtga                                                  17

<210> SEQ ID NO 741
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 741
atcgactctc gagtgttctc                                               20

<210> SEQ ID NO 742
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 742
aacgctcgac cttcgat                                                  17

<210> SEQ ID NO 743
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 743
ctcaacgctg gaccttccat                                               20

<210> SEQ ID NO 744
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 744
atcgacctac gtgcgttctc                                               20

<210> SEQ ID NO 745
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 745
gagaatgctg gaccttccat                                               20

<210> SEQ ID NO 746
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 746
tcacgctaac ctctgac                                                  17

<210> SEQ ID NO 747
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 747
gagaacgctc cagcactgat                                               20

<210> SEQ ID NO 748
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 748
gagcaagctg gaccttccat                                               20

<210> SEQ ID NO 749
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 749
cgctagaggt tagcgtga                                                 18

<210> SEQ ID NO 750
<211> LENGTH: 15
<212> TYPE: DNA
```

```
<213> ORGANISM: Artificial Sequence
<220> FEATURE:
<223> OTHER INFORMATION: Synthetic Sequence

<400> SEQUENCE: 750
gctagatgtt aacgt                                                          15

<210> SEQ ID NO 751
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 751
atggaaggtc cacgttctc                                                      19

<210> SEQ ID NO 752
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 752
gctagatgtt agcgt                                                          15

<210> SEQ ID NO 753
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 753
gctagacgtt agtgt                                                          15

<210> SEQ ID NO 754
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 754
tccatgacgg tcctgatgct                                                     20

<210> SEQ ID NO 755
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 755
tccatggcgg tcctgatgct                                                     20

<210> SEQ ID NO 756
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 756
gctagacgat agcgt                                                          15
```

<210> SEQ ID NO 757
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 757
gctagtcgat agcgt                                                        15

<210> SEQ ID NO 758
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 758
tccatgacgt tcctgatgct                                                   20

<210> SEQ ID NO 759
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 759
tccatgtcgt tcctgatgct                                                   20

<210> SEQ ID NO 760
<211> LENGTH: 15
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
<220> FEATURE:
<223> OTHER INFORMATION: Synthetic Sequence

<400> SEQUENCE: 760
gctagacgtt agngt                                                        15

<210> SEQ ID NO 761
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 761
gctaggcgtt agcgt                                                        15

<210> SEQ ID NO 762
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 762
tccatgtngg tcctgatgct    20

<210> SEQ ID NO 763
<211> LENGTH: 20
<212> TYPE: DNA
<213> ORGANISM: Artificial Sequence
<220> FEATURE:
<221> NAME/KEY: modified_base
<222> LOCATION: (12)...(12)
<223> OTHER INFORMATION: m5c
<220> FEATURE:
<223> OTHER INFORMATION: Synthetic Sequence

<400> SEQUENCE: 763
tccatgtcgg tnctgatgct    20

<210> SEQ ID NO 764
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 764
atngactctn gagngttctc    20

<210> SEQ ID NO 765
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 765
atggaaggtc cagtgttctc    20

<210> SEQ ID NO 766
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 766
gcatgacgtt gagct    15

<210> SEQ ID NO 767
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 767 gggtcaacg ttgaggggg    20

<210> SEQ ID NO 768
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 768
ggggtcaagt ctgagggggg                                          20

<210> SEQ ID NO 769
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 769
cgcgcgcgcg cgcgcgcgcg                                          20

<210> SEQ ID NO 770
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 770
cccccccccc cccccccccc ccccccc                                  28

<210> SEQ ID NO 771
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 771
cccccccccc cccccccccc cccccccccc ccccc                         35

<210> SEQ ID NO 772
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 772
tccatgtcgc tcctgatcct                                          20

<210> SEQ ID NO 773
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 773
gctaaacgtt agcgt                                               15

<210> SEQ ID NO 774
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 774
tccatgtcga tcctgatgct                                          20

<210> SEQ ID NO 775
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 775
tccatgccgg tcctgatgct                                          20

<210> SEQ ID NO 776
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 776
aaaatcaacg ttgaaaaaaa                                          20

<210> SEQ ID NO 777
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 777
tccataacgt tcctgatgct                                          20

<210> SEQ ID NO 778
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 778
tggaggtccc accgagatcg gag                                      23

<210> SEQ ID NO 779
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 779
cgtcgtcgtc gtcgtcgtcg t                                        21

<210> SEQ ID NO 780
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 780
ctgctgctgc tgctgctgct g                                        21

<210> SEQ ID NO 781
<211> LENGTH: 21
```

```
<212> TYPE: DNA
<213> ORGANISM: Artificial Sequence
<220> FEATURE:
<223> OTHER INFORMATION: Synthetic Sequence

<400> SEQUENCE: 781
gagaacgctc cgaccttcga t                                              21

<210> SEQ ID NO 782
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 782
gctagatgtt agcgt                                                     15

<210> SEQ ID NO 783
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 783
gcatgacgtt gagct                                                     15

<210> SEQ ID NO 784
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 784
tcaatgctga                                                           10

<210> SEQ ID NO 785
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 785
tcaacgttga                                                           10

<210> SEQ ID NO 786
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 786
```
tcaacgttga                                              10

<210> SEQ ID NO 787
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 787
gcaatattgc                                              10

<210> SEQ ID NO 788
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 788
gcaatattgc                                              10

<210> SEQ ID NO 789
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 789
agttgcaact                                              10

<210> SEQ ID NO 790
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 790 tcttcgaa                                                 8

<210> SEQ ID NO 791
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 791 tcaacgtc                                                 8

<210> SEQ ID NO 792
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 792

-continued ccatgtcggt cctgatgct                    19

<210> SEQ ID NO 793
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 793
gtttttatat aatttggg                     18

<210> SEQ ID NO 794
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 794
tttttgtttg tcgttttgtc gtt               23

<210> SEQ ID NO 795
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 795
ttgggggggg tt                           12

<210> SEQ ID NO 796
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 796
ggggttgggg gtt                          13

<210> SEQ ID NO 797
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 797
ggtggtgtag gttttgg                      17

<210> SEQ ID NO 798
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 798
gagaangctc gaccttcgat          20

<210> SEQ ID NO 799
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 799
tcaacgttaa cgttaacgtt          20

<210> SEQ ID NO 800
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 800
gagcaagntg gaccttccat          20

<210> SEQ ID NO 801
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 801
gagaangctc cagcactgat          20

<210> SEQ ID NO 802
<211> LENGTH: 10
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 802 tcaangttga          10

<210> SEQ ID NO 803
<211> LENGTH: 10
<212> TYPE: DNA
<213> ORGANISM: Artificial Sequence
<220> FEATURE:
<221> NAME/KEY: modified_base

```
<222> LOCATION: (2)...(2)
<223> OTHER INFORMATION: m5c
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 803 gnaatattgc                                                              10

<210> SEQ ID NO 804
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 804
tgctgctttt gtcgttttgt gctt                                              24

<210> SEQ ID NO 805
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 805
ctgcgttagc aatttaactg tg                                                22

<210> SEQ ID NO 806
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 806
tccatgacgt tcctgatgct                                                   20

<210> SEQ ID NO 807
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 807
tgcatgccgt gcatccgtac acagctct                                          28

<210> SEQ ID NO 808
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 808
tgcatgccgt acacagctct                                                   20

<210> SEQ ID NO 809
<211> LENGTH: 12
<212> TYPE: DNA
<213> ORGANISM: Artificial Sequence
<220> FEATURE:
<223> OTHER INFORMATION: Synthetic Sequence
```

```
<400> SEQUENCE: 809
tgcatcagct ct                                                           12

<210> SEQ ID NO 810
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 810 tgcgctct                                                                 8

<210> SEQ ID NO 811
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 811
cccccccccc cccccccccc                                                   20

<210> SEQ ID NO 812
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 812
cccccccccc cc                                                           12

<210> SEQ ID NO 813
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 813 cccccccc                                                                 8

<210> SEQ ID NO 814
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 814
tgcatcagct ct                                                           12

<210> SEQ ID NO 815
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 815
tgcatgccgt acacagctct                                                   20

<210> SEQ ID NO 816
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 816
gagcaagctg gaccttccat                                                      20

<210> SEQ ID NO 817
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 817
tcaacgttaa cgttaacgtt aacgttaacg tt                                        32

<210> SEQ ID NO 818
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 818
gagaacgctc gaccttcgat                                                      20

<210> SEQ ID NO 819
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 819
gtccccattt cccagaggag gaaat                                                25

<210> SEQ ID NO 820
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 820
ctagcggctg acgtcatcaa gctag                                                25

<210> SEQ ID NO 821
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 821
ctagcttgat gacgtcagcc gctag                                                25

<210> SEQ ID NO 822
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 822
```

```
cggctgacgt catcaa                                              16

<210> SEQ ID NO 823
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 823 ctgacgtg                                                       8

<210> SEQ ID NO 824
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 824
ctgacgtcat                                                     10

<210> SEQ ID NO 825
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 825
attcgatcgg ggcggggcga g                                        21

<210> SEQ ID NO 826
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 826
ctcgccccgc cccgatcgaa t                                        21

<210> SEQ ID NO 827
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 827
gactgacgtc agcgt                                               15

<210> SEQ ID NO 828
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 828
ctagcggctg acgtcataaa gctagc                                   26

<210> SEQ ID NO 829
<211> LENGTH: 26
<212> TYPE: DNA
```

```
<213> ORGANISM: Artificial Sequence
<220> FEATURE:
<223> OTHER INFORMATION: Synthetic Sequence

<400> SEQUENCE: 829
ctagctttat gacgtcagcc gctagc                                          26

<210> SEQ ID NO 830
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 830
ctagcggctg agctcataaa gctagc                                          26

<210> SEQ ID NO 831
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 831
ctagtggctg acgtcatcaa gctag                                           25

<210> SEQ ID NO 832
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 832
tccaccacgt ggtctatgct                                                 20

<210> SEQ ID NO 833
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 833
gggaatgaaa gattttatta taag                                            24

<210> SEQ ID NO 834
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 834
tctaaaaacc atctattctt aaccct                                          26

<210> SEQ ID NO 835
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 835
agctcaacgt catgc                                                      15
```

<210> SEQ ID NO 836
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 836
ttaacggtgg tagcggtatt ggtc                                    24

<210> SEQ ID NO 837
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 837
ttaagaccaa taccgctacc accg                                    24

<210> SEQ ID NO 838
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 838
gatctagtga tgagtcagcc ggatc                                   25

<210> SEQ ID NO 839
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 839
gatccggctg actcatcact agatc                                   25

<210> SEQ ID NO 840
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 840
tccaagacgt tcctgatgct                                         20

<210> SEQ ID NO 841
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 841
tccatgacgt ccctgatgct                                         20

<210> SEQ ID NO 842
<211> LENGTH: 20
<212> TYPE: DNA
<213> ORGANISM: Artificial Sequence
<220> FEATURE:

```
<223> OTHER INFORMATION: Synthetic Sequence

<400> SEQUENCE: 842
tccaccacgt ggctgatgct                                               20

<210> SEQ ID NO 843
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 843
ccacgtggac ctctagc                                                  17

<210> SEQ ID NO 844
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 844
tcagaccacg tggtcgggtg ttcctga                                       27

<210> SEQ ID NO 845
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 845
tcaggaacac ccgaccacgt ggtctga                                       27

<210> SEQ ID NO 846
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 846
catttccacg atttccca                                                 18

<210> SEQ ID NO 847
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 847
ttcctctctg caagagact                                                19

<210> SEQ ID NO 848
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 848
tgtatctctc tgaaggact                                                19
```

```
<210> SEQ ID NO 849
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 849
ataaagcgaa actagcagca gtttc                                              25

<210> SEQ ID NO 850
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 850
gaaactgctg ctagtttcgc tttat                                              25

<210> SEQ ID NO 851
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 851
tgcccaaaga ggaaaatttg tttcatacag                                         30

<210> SEQ ID NO 852
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 852
ctgtatgaaa caaattttcc tctttgggca                                         30

<210> SEQ ID NO 853
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 853
ttagggttag ggttagggtt                                                    20

<210> SEQ ID NO 854
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 854
tccatgagct tcctgatgct                                                    20

<210> SEQ ID NO 855
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 855
aaaacatgac gttcaaaaaa                                              20

<210> SEQ ID NO 856
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 856
aaaacatgac gttcgggggg                                              20

<210> SEQ ID NO 857
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 857
ggggcatgag cttcgggggg                                              20

<210> SEQ ID NO 858
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 858
ctaggctgac gtcatcaagc tagt                                         24

<210> SEQ ID NO 859
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 859
tctgacgtca tctgacgttg gctgacgtct                                   30

<210> SEQ ID NO 860
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 860
ggaattagta atagatatag aagtt                                        25

<210> SEQ ID NO 861
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 861
tttacctttt ataaacataa ctaaaacaaa                                   30

<210> SEQ ID NO 862
<211> LENGTH: 15
```

```
<212> TYPE: DNA
<213> ORGANISM: Artificial Sequence
<220> FEATURE:
<223> OTHER INFORMATION: Synthetic Sequence

<400> SEQUENCE: 862
gcgttttttt ttgcg                                                          15

<210> SEQ ID NO 863
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 863
atatctaatc aaaacattaa caaa                                                24

<210> SEQ ID NO 864
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 864
tctatcccag gtggttcctg ttag                                                24

<210> SEQ ID NO 865
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 865
tccatgacgt tcctgatgct                                                     20

<210> SEQ ID NO 866
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 866
tccatgagct tcctgatgct                                                     20

<210> SEQ ID NO 867
<211> LENGTH: 13
<212> TYPE: DNA
<213> ORGANISM: Artificial Sequence
<220> FEATURE:
<221> NAME/KEY: misc_feature
<222> LOCATION: (11)...(13)
<223> OTHER INFORMATION: Conjugated to FITC moiety.
<221> NAME/KEY: misc_feature
<222> LOCATION: (0)...(0)
<223> OTHER INFORMATION: Has phosphodiester backbone.
<220> FEATURE:
<223> OTHER INFORMATION: Synthetic Sequence
```

<400> SEQUENCE: 867
tttttttttt ttt                                                          13

<210> SEQ ID NO 868
<211> LENGTH: 13
<212> TYPE: DNA
<213> ORGANISM: Artificial Sequence
<220> FEATURE:
<221> NAME/KEY: misc_feature
<222> LOCATION: (11)...(13)
<223> OTHER INFORMATION: Conjugated to biotin moiety.
<221> NAME/KEY: misc_feature
<222> LOCATION: (0)...(0)
<223> OTHER INFORMATION: Has phosphorothioate and phosphodiester
      chimeric backbone with phosphodiester on 3' end.
<220> FEATURE:
<223> OTHER INFORMATION: Synthetic Sequence

<400> SEQUENCE: 868
tttttttttt ttt                                                          13

<210> SEQ ID NO 869
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 869
ctagcttgat gagctcagcc gctag                                             25

<210> SEQ ID NO 870
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 870
ttcagttgtc ttgctgctta gctaa                                             25

<210> SEQ ID NO 871
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 871
tccatgagct tcctgagtct                                                   20

<210> SEQ ID NO 872
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 872
ctagcggctg acgtcatcaa tctag                                             25

<210> SEQ ID NO 873
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 873
tgctagctgt gcctgtacct                           20

<210> SEQ ID NO 874
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 874
atgctaaagg acgtcacatt gca                       23

<210> SEQ ID NO 875
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 875
tgcaatgtga cgtcctttag cat                       23

<210> SEQ ID NO 876
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 876
gtaggggact tccgagctc gagatcctat g                31

<210> SEQ ID NO 877
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 877
cataggatct cgagctcgga aagtcccta c                31

<210> SEQ ID NO 878
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 878
ctgtcaggaa ctgcaggtaa gg                        22

<210> SEQ ID NO 879
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 879
cataacatag gaatatttac tcctcgc                   27

<210> SEQ ID NO 880
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 880
ctccagctcc aagaaaggac g                                           21

<210> SEQ ID NO 881
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 881
gaagtttctg gtaagtcttc g                                           21

<210> SEQ ID NO 882
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 882
tgctgctttt gtgcttttgt gctt                                        24

<210> SEQ ID NO 883
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 883
tcgtcgtttt gtggttttgt ggtt                                        24

<210> SEQ ID NO 884
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 884
tcgtcgtttg tcgttttgtc gtt                                         23

<210> SEQ ID NO 885
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 885
tcctgacgtt cggcgcgcgc cc                                          22

<210> SEQ ID NO 886
<211> LENGTH: 24
<212> TYPE: DNA
<213> ORGANISM: Artificial Sequence
<220> FEATURE:
<223> OTHER INFORMATION: Synthetic Sequence -continued

```
<400> SEQUENCE: 886
tgctgctttt gtgcttttgt gctt                                              24

<210> SEQ ID NO 887
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 887
tccatgagct tcctgagctt                                                   20

<210> SEQ ID NO 888
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 888
tcgtcgtttc gtcgttttga cgtt                                              24

<210> SEQ ID NO 889
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 889
tcgtcgtttg cgtgcgtttc gtcgtt                                            26

<210> SEQ ID NO 890
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 890
tcgcgtgcgt tttgtcgttt tgacgtt                                           27

<210> SEQ ID NO 891
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 891
ttcgtcgttt tgtcgttttg tcgtt                                             25

<210> SEQ ID NO 892
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 892
tcctgacggg gaagt                                                        15

<210> SEQ ID NO 893
<211> LENGTH: 15
```

```
<212> TYPE: DNA
<213> ORGANISM: Artificial Sequence
<220> FEATURE:
<223> OTHER INFORMATION: Synthetic Sequence

<400> SEQUENCE: 893
tcctggcgtg gaagt                                                    15

<210> SEQ ID NO 894
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 894
tcctggcggt gaagt                                                    15

<210> SEQ ID NO 895
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 895
tcctggcgtt gaagt                                                    15

<210> SEQ ID NO 896
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 896
tcctgacgtg gaagt                                                    15

<210> SEQ ID NO 897
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 897
gcgacgttcg gcgcgcgccc                                               20

<210> SEQ ID NO 898
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 898
gcgacgggcg gcgcgcgccc                                               20

<210> SEQ ID NO 899
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 899
```

```
gcggcgtgcg gcgcgcgccc                                                   20

<210> SEQ ID NO 900
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 900
gcggcggtcg gcgcgcgccc                                                   20

<210> SEQ ID NO 901
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 901
gcgacggtcg gcgcgcgccc                                                   20

<210> SEQ ID NO 902
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 902
gcggcgttcg gcgcgcgccc                                                   20

<210> SEQ ID NO 903
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 903
gcgacgtgcg gcgcgcgccc                                                   20

<210> SEQ ID NO 904
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 904
tcgtcgctgt ctccg                                                        15

<210> SEQ ID NO 905
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 905
tgtgggggtt ttggttttgg                                                   20

<210> SEQ ID NO 906
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 906 agggggaggggg aggggagggg                                             20

<210> SEQ ID NO 907
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 907
tgtgtgtgtg tgtgtgtgtg t                                             21

<210> SEQ ID NO 908
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 908
ctctctctct ctctctctct ct                                            22

<210> SEQ ID NO 909
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 909
ggggtcgacg tcgaggggggg                                              20

<210> SEQ ID NO 910
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 910
atatatatat atatatatat at                                            22

<210> SEQ ID NO 911
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 911
tttttttttt tttttttttt ttttttt                                       27

<210> SEQ ID NO 912
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 912
tttttttttt tttttttttt t                                             21
```

<210> SEQ ID NO 913
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 913
tttttttttt tttttttt                                                   18

<210> SEQ ID NO 914
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 914
gctagagggg agggt                                                      15

<210> SEQ ID NO 915
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 915
gctagatgtt agggg                                                      15

<210> SEQ ID NO 916
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 916
gcatgagggg gagct                                                      15

<210> SEQ ID NO 917
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 917
atggaaggtc caggggctc                                                  20

<210> SEQ ID NO 918
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 918
atggactctg gaggggctc                                                  20

<210> SEQ ID NO 919
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 919
atggaaggtc caaggggctc                                                    20

<210> SEQ ID NO 920
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 920
gagaaggggg gaccttggat                                                    20

<210> SEQ ID NO 921
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 921
gagaaggggg gaccttccat                                                    20

<210> SEQ ID NO 922
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 922 gagaagggc cagcactgat                                                     20

<210> SEQ ID NO 923
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 923
tccatgtggg gcctgatgct                                                    20

<210> SEQ ID NO 924
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 924
tccatgaggg gcctgatgct                                                    20

<210> SEQ ID NO 925
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 925
tccatgtggg gcctgctgat                                                    20

<210> SEQ ID NO 926

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 926
atggactctc cggggttctc                                              20

<210> SEQ ID NO 927
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 927
atggaaggtc cggggttctc                                              20

<210> SEQ ID NO 928
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 928
atggactctg gagggtctc                                               20

<210> SEQ ID NO 929
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 929
atggaggctc catggggctc                                              20

<210> SEQ ID NO 930
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 930
atggactctg gggggttctc                                              20

<210> SEQ ID NO 931
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 931
tccatgtggg tggggatgct                                              20

<210> SEQ ID NO 932
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 932
```
tccatgcggg tgggatgct                                          20

<210> SEQ ID NO 933
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 933
tccatggggg tcctgatgct                                         20

<210> SEQ ID NO 934
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 934
tccatggggt ccctgatgct                                         20

<210> SEQ ID NO 935
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 935
tccatggggt gcctgatgct                                         20

<210> SEQ ID NO 936
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 936
tccatggggt tcctgatgct                                         20

<210> SEQ ID NO 937
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 937
tccatcgggg gcctgatgct                                         20

<210> SEQ ID NO 938
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 938
gctagaggga gtgt                                               14

<210> SEQ ID NO 939
<211> LENGTH: 18
<212> TYPE: DNA

```
<213> ORGANISM: Artificial Sequence
<220> FEATURE:
<223> OTHER INFORMATION: Synthetic Sequence

<400> SEQUENCE: 939
tttttttttt tttttttt                                                  18

<210> SEQ ID NO 940
<211> LENGTH: 21
<212> TYPE: DNA
<213> ORGANISM: Artificial Sequence
<220> FEATURE:
<221> NAME/KEY: misc_difference
<222> LOCATION: (2)...(2)
<223> OTHER INFORMATION: m is a or c
<221> NAME/KEY: misc_difference
<222> LOCATION: (18)...(18)
<223> OTHER INFORMATION: m is a or c
<220> FEATURE:
<223> OTHER INFORMATION: Synthetic Sequence

<400> SEQUENCE: 940
gmggtcaacg ttgagggmgg g                                              21

<210> SEQ ID NO 941
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 941
ggggagttcg ttgagggggg g                                              21

<210> SEQ ID NO 942
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 942
tcgtcgtttc cccccccccc                                                20

<210> SEQ ID NO 943
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 943 ttgggggtt ttttttttt ttttt                                            25

<210> SEQ ID NO 944
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 944
tttaaatttt aaaatttaaa ata                                            23

<210> SEQ ID NO 945
<211> LENGTH: 24
<212> TYPE: DNA
```

<213> ORGANISM: Artificial Sequence
<220> FEATURE:
<223> OTHER INFORMATION: Synthetic Sequence

<400> SEQUENCE: 945
ttggtttttt tggtttttt ttgg                                        24

<210> SEQ ID NO 946
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 946
tttccctttt cccctttcc cctc                                        24

<210> SEQ ID NO 947
<211> LENGTH: 21
<212> TYPE: DNA
<213> ORGANISM: Artificial Sequence
<220> FEATURE:
<221> NAME/KEY: misc_difference
<222> LOCATION: (21)...(21)
<223> OTHER INFORMATION: s is g or c
<220> FEATURE:
<223> OTHER INFORMATION: Synthetic Sequence

<400> SEQUENCE: 947
ggggtcatcg atgagggggg s                                          21

<210> SEQ ID NO 948
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 948
tccatgacgt tcctgacgtt                                            20

<210> SEQ ID NO 949
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 949
tccatgacgt tcctgacgtt                                            20

<210> SEQ ID NO 950
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 950
tccatgacgt tcctgacgtt                                            20

<210> SEQ ID NO 951
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 951
tccatgacgt tcctgacgtt                                              20

<210> SEQ ID NO 952
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 952
tccatgacgt tcctgacgtt                                              20

<210> SEQ ID NO 953
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 953
tccatgacgt tcctgacgtt                                              20

<210> SEQ ID NO 954
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 954
tccatgacgt tcctgacgtt                                              20

<210> SEQ ID NO 955
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 955
tccatgacgt tcctgacgtt                                              20

<210> SEQ ID NO 956
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 956
tccatgacgt tcctgacgtt                                              20

<210> SEQ ID NO 957
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 957
tccatgacgt tcctgacgtt                                              20

<210> SEQ ID NO 958
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 958
tccatgacgt tcctgacgtt                                              20

<210> SEQ ID NO 959
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 959
gggggacgat cgtcggggg                                               19

<210> SEQ ID NO 960
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 960
gggggtcgta cgacgggggg                                              20

<210> SEQ ID NO 961
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 961
tttttttttt tttttttttt tttt                                         24

<210> SEQ ID NO 962
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 962
aaaaaaaaaa aaaaaaaaaa aaaa                                         24

<210> SEQ ID NO 963
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 963
cccccccccc cccccccccc cccc                                         24

<210> SEQ ID NO 964
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 964
```

-continued tcgtcgtttt gtcgttttgt cgtt                                          24

<210> SEQ ID NO 965
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 965
tcgtcgtttt gtcgttttgt cgtt                                          24

<210> SEQ ID NO 966
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 966
tcgtcgtttt gtcgttttgt cgtt                                          24

<210> SEQ ID NO 967
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 967
tcgtcgtttt gtcgttttgt cgtt                                          24

<210> SEQ ID NO 968
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 968
ggggtcaacg ttgagggggg                                               20

<210> SEQ ID NO 969
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 969
ggggtcaacg ttgagggggg                                               20

<210> SEQ ID NO 970
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 970
ggggtcaagc ttgagggggg                                               20

<210> SEQ ID NO 971
<211> LENGTH: 20
<212> TYPE: DNA

```
<213> ORGANISM: Artificial Sequence
<220> FEATURE:
<223> OTHER INFORMATION: Synthetic Sequence

<400> SEQUENCE: 971
tgctgcttcc cccccccccc                                               20

<210> SEQ ID NO 972
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 972
ggggacgtcg acgtggggggg                                              20

<210> SEQ ID NO 973
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 973
ggggtcgtcg acgaggggggg                                              20

<210> SEQ ID NO 974
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 974
ggggtcgacg tacgtcgagg gggg                                          24

<210> SEQ ID NO 975
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 975
ggggaccggt accggtgggg gg                                            22

<210> SEQ ID NO 976
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 976
gggtcgacgt cgagggggg                                                19

<210> SEQ ID NO 977
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 977
ggggtcgacg tcgagggggg                                               19
```

```
<210> SEQ ID NO 978
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 978
ggggaacgtt aacgttgggg gg                                          22

<210> SEQ ID NO 979
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 979
ggggtcaccg gtgaggggggg                                            20

<210> SEQ ID NO 980
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 980
ggggtcgttc gaacgagggg gg                                          22

<210> SEQ ID NO 981
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 981
ggggacgttc gaacgtgggg gg                                          22

<210> SEQ ID NO 982
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 982
tcaactttga                                                        10

<210> SEQ ID NO 983
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 983
tcaagcttga                                                        10

<210> SEQ ID NO 984
<211> LENGTH: 12
<212> TYPE: DNA
<213> ORGANISM: Artificial Sequence
<220> FEATURE:
```

<223> OTHER INFORMATION: Synthetic Sequence

<400> SEQUENCE: 984
tcacgatcgt ga                                                          12

<210> SEQ ID NO 985
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 985
tcagcatgct ga                                                          12

<210> SEQ ID NO 986
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 986
gggggagcat gctggggggg                                                  20

<210> SEQ ID NO 987
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 987
gggggggggg gggggggggg                                                  20

<210> SEQ ID NO 988
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 988
gggggacgat atcgtcgggg gg                                               22

<210> SEQ ID NO 989
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 989
gggggacgac gtcgtcgggg gg                                               22

<210> SEQ ID NO 990
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 990
gggggacgag ctcgtcgggg gg                                               22

```
<210> SEQ ID NO 991
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 991
gggggacgta cgtcgggggg                                                   20

<210> SEQ ID NO 992
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 992 tcaacgtt                                                                 8

<210> SEQ ID NO 993
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 993
tccataccgg tcctgatgct                                                   20

<210> SEQ ID NO 994
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 994
tccataccgg tcctaccggt                                                   20

<210> SEQ ID NO 995
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 995
gggggacgat cgttgggggg                                                   20

<210> SEQ ID NO 996
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 996
ggggaacgat cgtcggggggg                                                  20

<210> SEQ ID NO 997
<211> LENGTH: 21
<212> TYPE: DNA
<213> ORGANISM: Artificial Sequence
<220> FEATURE:
<223> OTHER INFORMATION: Synthetic Sequence
```

-continued

```
<400> SEQUENCE: 997 gggggggacga tcgtcggggg g                                              21

<210> SEQ ID NO 998
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 998
gggggacgat cgtcggggggg g                                              21

<210> SEQ ID NO 999
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 999
aaagacgtta aa                                                         12

<210> SEQ ID NO 1000
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1000
aaagagctta aa                                                         12

<210> SEQ ID NO 1001
<211> LENGTH: 12
<212> TYPE: DNA
<213> ORGANISM: Artificial Sequence
<220> FEATURE:
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 1001
aaagangtta aa                                                         12

<210> SEQ ID NO 1002
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1002
aaattcggaa aa                                                         12

<210> SEQ ID NO 1003
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1003
gggggtcatc gatgaggggg g                                               21
```

<210> SEQ ID NO 1004
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1004 ggggtcaac gttgaggggg g                                        21

<210> SEQ ID NO 1005
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1005
atgtagctta ataacaaagc                                         20

<210> SEQ ID NO 1006
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1006
ggatcccttg agttacttct                                         20

<210> SEQ ID NO 1007
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1007
ccattccact tctgattacc                                         20

<210> SEQ ID NO 1008
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1008
tatgtattat catgtagata                                         20

<210> SEQ ID NO 1009
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1009
agcctacgta ttcaccctcc                                         20

<210> SEQ ID NO 1010
<211> LENGTH: 20
<212> TYPE: DNA
<213> ORGANISM: Artificial Sequence
<220> FEATURE:

```
<223> OTHER INFORMATION: Synthetic Sequence

<400> SEQUENCE: 1010
ttcctgcaac tactattgta                                              20

<210> SEQ ID NO 1011
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1011
atagaaggcc ctacaccagt                                              20

<210> SEQ ID NO 1012
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1012
ttacaccggt ctatggaggt                                              20

<210> SEQ ID NO 1013
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1013
ctaaccagat caagtctagg                                              20

<210> SEQ ID NO 1014
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1014
cctagacttg atctggttag                                              20

<210> SEQ ID NO 1015
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1015
tataagcctc gtccgacatg                                              20

<210> SEQ ID NO 1016
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1016
catgtcggac gaggcttata                                              20
```

```
<210> SEQ ID NO 1017
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1017
tggtggtggg gagtaagctc                                               20

<210> SEQ ID NO 1018
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1018
gagctactcc cccaccacca                                               20

<210> SEQ ID NO 1019
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1019
gccttcgatc ttcgttggga                                               20

<210> SEQ ID NO 1020
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1020
tggacttctc tttgccgtct                                               20

<210> SEQ ID NO 1021
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1021
atgctgtagc ccagcgataa                                               20

<210> SEQ ID NO 1022
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1022
accgaatcag cggaaagtga                                               20

<210> SEQ ID NO 1023
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 1023
tccatgacgt tcctgacgtt                                              20

<210> SEQ ID NO 1024
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1024
ggagaaaccc atgagctcat ctgg                                         24

<210> SEQ ID NO 1025
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1025
accacagacc agcaggcaga                                              20

<210> SEQ ID NO 1026
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1026
gagcgtgaac tgcgcgaaga                                              20

<210> SEQ ID NO 1027
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1027
tcggtaccct tgcagcggtt                                              20

<210> SEQ ID NO 1028
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1028
ctggagccct agccaaggat                                              20

<210> SEQ ID NO 1029
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1029
gcgactccat caccagcgat                                              20

<210> SEQ ID NO 1030
<211> LENGTH: 21
```

<212> TYPE: DNA
<213> ORGANISM: Artificial Sequence
<220> FEATURE:
<223> OTHER INFORMATION: Synthetic Sequence

<400> SEQUENCE: 1030
cctgaagtaa gaaccagatg t                                               21

<210> SEQ ID NO 1031
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1031
ctgtgttatc tgacatacac c                                               21

<210> SEQ ID NO 1032
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1032
aattagccct taggtgattgg g                                              21

<210> SEQ ID NO 1033
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1033
acatctggtt cttacttcag g                                               21

<210> SEQ ID NO 1034
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 1034
ataagtcata ttttgggaac tac                                             23

<210> SEQ ID NO 1035
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1035
cccaatcacc taaggctaat t                                               21

<210> SEQ ID NO 1036
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1036
ggggtcgtcg acgaggggggg          20

<210> SEQ ID NO 1037
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1037
ggggtcgttc gaacgagggg gg          22

<210> SEQ ID NO 1038
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1038
ggggacgttc gaacgtgggg gg          22

<210> SEQ ID NO 1039
<211> LENGTH: 15
<212> TYPE: DNA
<213> ORGANISM: Artificial Sequence
<220> FEATURE:
<221> NAME/KEY: modified_base
<222> LOCATION: (9)...(9)
<223> OTHER INFORMATION: n is 5-methylcytosine.
<220> FEATURE:
<223> OTHER INFORMATION: Synthetic Sequence

<400> SEQUENCE: 1039
tcctggcgng gaagt          15

<210> SEQ ID NO 1040
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1040
ggggaacgac gtcgttgggg gg          22

<210> SEQ ID NO 1041
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1041
ggggaacgta cgtcgggggg          20

<210> SEQ ID NO 1042
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1042
ggggaacgta cgtacgttgg gggg          24

```
<210> SEQ ID NO 1043
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1043
ggggtcaccg gtgaggggggg                                              20

<210> SEQ ID NO 1044
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1044
ggggtcgacg tacgtcgagg gggg                                          24

<210> SEQ ID NO 1045
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1045
ggggaccggt accggtgggg gg                                            22

<210> SEQ ID NO 1046
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1046
gggtcgacgt cgaggggggg                                               19

<210> SEQ ID NO 1047
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1047
ggggtcgacg tcgagggg                                                 18

<210> SEQ ID NO 1048
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1048
ggggaacgtt aacgttgggg gg                                            22

<210> SEQ ID NO 1049
<211> LENGTH: 19
<212> TYPE: DNA
<213> ORGANISM: Artificial Sequence
<220> FEATURE:
<223> OTHER INFORMATION: Synthetic Sequence
```

```
<400> SEQUENCE: 1049
ggggacgtcg acgtggggg                                               19

<210> SEQ ID NO 1050
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 1050
gcactcttcg aagctacagc cggcagcctc tgat                              34

<210> SEQ ID NO 1051
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 1051
cggctcttcc atgaggtctt tgctaatctt gg                                32

<210> SEQ ID NO 1052
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 1052
cggctcttcc atgaaagtct ttggacgatg tgagc                             35

<210> SEQ ID NO 1053
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1053
tcctgcaggt taagt                                                   15

<210> SEQ ID NO 1054
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1054
gggggtcgtt cgttgggggg                                              20

<210> SEQ ID NO 1055
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1055
gggggatgat tgttgggggg                                              20

<210> SEQ ID NO 1056
<211> LENGTH: 20
```

```
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<221> NAME/KEY: modified_base
<222> LOCATION: (11)...(11)
<223> OTHER INFORMATION: m5c
<220> FEATURE:
<223> OTHER INFORMATION: Synthetic Sequence

<400> SEQUENCE: 1056
gggggangat ngttgggggg                                          20

<210> SEQ ID NO 1057
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1057
gggggagcta gcttgggggg                                          20

<210> SEQ ID NO 1058
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1058
ggttcttttg gtccttgtct                                          20

<210> SEQ ID NO 1059
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1059
ggttcttttg gtcctcgtct                                          20

<210> SEQ ID NO 1060
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1060
ggttcttttg gtccttatct                                          20

<210> SEQ ID NO 1061
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1061
ggttcttggt ttccttgtct                                          20

<210> SEQ ID NO 1062
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 1062
tggtcttttg gtccttgtct                                            20

<210> SEQ ID NO 1063
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1063
ggttcaaatg gtccttgtct                                            20

<210> SEQ ID NO 1064
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1064
gggtcttttg ggccttgtct                                            20

<210> SEQ ID NO 1065
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1065
tccaggactt ctctcaggtt tttt                                       24

<210> SEQ ID NO 1066
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1066
tccaaaactt ctctcaaatt                                            20

<210> SEQ ID NO 1067
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1067
tactactttt atacttttat actt                                       24

<210> SEQ ID NO 1068
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1068
```

-continued

```
tgtgtgtgtg tgtgtgtgtg tgtg                                          24

<210> SEQ ID NO 1069
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 1069
ttgttgttgt tgtttgttgt tgttg                                         25

<210> SEQ ID NO 1070
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 1070
ggctccgggg agggaatttt tgtctat                                       27

<210> SEQ ID NO 1071
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1071
gggacgatcg tcggggggg                                                19

<210> SEQ ID NO 1072
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1072
gggtcgtcga cgagggggggg                                              20

<210> SEQ ID NO 1073
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1073
ggtcgtcgac gagggggg                                                 19

<210> SEQ ID NO 1074
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1074
gggtcgtcgt cgtggggggg                                               20

<210> SEQ ID NO 1075
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 1075
ggggacgatc gtcggggggg                                               20

<210> SEQ ID NO 1076
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1076
ggggacgtcg tcgtggggggg                                              20

<210> SEQ ID NO 1077
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 1077
ggggtcgacg tcgacgtcga ggggggg                                       27

<210> SEQ ID NO 1078
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1078
ggggaaccgc ggttggggggg g                                            21

<210> SEQ ID NO 1079
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1079
ggggacgacg tcgtggggggg g                                            21

<210> SEQ ID NO 1080
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 1080
tcgtcgtcgt cgtcgtgggg ggg                                           23

<210> SEQ ID NO 1081
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1081
tcctgccggg gaagt                                                    15
```

<210> SEQ ID NO 1082
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1082
tcctgcaggg gaagt                                                      15

<210> SEQ ID NO 1083
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1083
tcctgaaggg gaagt                                                      15

<210> SEQ ID NO 1084
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1084
tcctggcggg caagt                                                      15

<210> SEQ ID NO 1085
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1085
tcctggcggg taagt                                                      15

<210> SEQ ID NO 1086
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1086
tcctggcggg aaagt                                                      15

<210> SEQ ID NO 1087
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1087
tccgggcggg gaagt                                                      15

<210> SEQ ID NO 1088
<211> LENGTH: 15
<212> TYPE: DNA
<213> ORGANISM: Artificial Sequence
<220> FEATURE:
<223> OTHER INFORMATION: Synthetic Sequence

```
<400> SEQUENCE: 1088
tcggggcggg gaagt                                                    15

<210> SEQ ID NO 1089
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1089
tcccggcggg gaagt                                                    15

<210> SEQ ID NO 1090
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1090
gggggacgtt ggggg                                                    15

<210> SEQ ID NO 1091
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1091
ggggtttttt ttttggggggg                                              20

<210> SEQ ID NO 1092
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1092
ggggcccccc ccccgggggg                                               20

<210> SEQ ID NO 1093
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1093
ggggttgttg ttgttggggg g                                             21
```

IMMUNOSTIMULATORY NUCLEIC ACIDS FOR THE TREATMENT OF ASTHMA AND ALLERGY

PRIORITY OF THE INVENTION

This application claims priority under Title 35 §119(e), of U.S. Provisional Application No. 60/179,991, filed Feb. 3, 2000, entitled IMMUNOSTIMULATORY NUCLEIC ACIDS FOR THE TREATMENT OF ASTHMA AND ALLERGY, the entire contents of which are incorporated herein by reference.

BACKGROUND OF THE INVENTION

Asthma is a chronic inflammatory disease effecting 14-15 million persons in the U.S. alone. Symptoms of asthma include recurrent episodes of wheezing, breathlessness, and chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, subbasement membrane fibrosis may occur, leading to persistent abnormalities in lung function.

Research over the past several years has revealed that asthma likely results from complex interactions among inflammatory cells, mediators, and other cells and tissues resident in the airway. Mast cells, eosinophils, epithelial cells, macrophage, and activated T-cells all play an important role in the inflammatory process associated with asthma (Djukanovic et al., *Am. Rev. Respir. Dis;* 142:434-457; 1990). It is believed that these cells can influence airway function through secretion of preformed and newly synthesized mediators which can act directly or indirectly on the local tissue. It has also been recognized that subpopulations of T-lymphocytes (TH-2) play an important role in regulating allergic inflammation in the airway by releasing selective cytokines and establishing disease chronicity (Robinson, et al. *N. Engl. J. Med.;* 326:298-304; 1992).

Asthma is a complex disorder which arises at different stages in development and can be classified based on the degree of symptoms of acute, subacute or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway.

Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and medacromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. There are many side effects associated with each of these drugs and none of the drugs alone or in combination is capable of preventing or completely treating asthma.

Allergy is a disease associated with the production of antibodies from a particular class of immunoglobulin, IgE, against allergens. The development of an IgE-mediated response to common aeroallergens is also a factor which indicates predisposition towards the development of asthma. If an allergen encounters a specific IgE which is bound to an Fc IgE receptor on the surface of a basophil (circulating in the blood) or mast cell (dispersed throughout solid tissue), the cell becomes activated, resulting in the production and release of mediators such as histamine, scrotonin, and lipid mediators. Allergic diseases include but are not limited to rhinitis (hay fever) asthma, urticaria and atopic dermatitis.

Conventional methods for treating or preventing allergy have involved the use of anti-histamines or desensitization therapies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

SUMMARY OF THE INVENTION

Improved methods and products for the prevention and/or treatment of asthma and allergy are provided according to the invention. The invention is based, in some aspects, on the finding that when immunostimulatory nucleic acid molecules are used in conjunction with medicaments for the treatment of asthma and allergy, some unexpected and improved results are observed. For instance, the efficacy of the combination of immunostimulatory nucleic acids and asthma and allergy medicaments is profoundly improved over the use of each of the medicaments alone. The results are surprising in part because the drugs act through different mechanisms and would not necessarily be expected to improve the efficacy of one another in a synergistic manner.

In some aspects, the invention is a method for preventing or treating asthma or allergy by administering a synergistic combination of an immunostimulatory nucleic acid and an asthma/allergy medicament, wherein the combination is administered in an effective amount for synergistically reducing the immune or inflammatory response caused by a mediator of asthma or allergy. It was surprisingly discovered according to the invention that the combination of the immunostimulatory nucleic acid and the asthma/allergy medicament worked synergistically to reduce the immune or inflammatory response initiated when a mediator of asthma or allergy is encountered.

In other aspects, the invention is a method for altering the dosage of the asthma/allergy medicament that is required to treat a subject suffering from asthma or allergy. The invention in one aspect is a method for increasing the dose of an asthma/ allergy medicament without inducing the level of side effects ordinarily observed with that dose of an asthma/allergy medicament. The method is accomplished by administering to a subject suffering from asthma or allergy or at risk of developing asthma or allergy, an asthma/allergy medicament in a dose which would ordinarily induce side effects, administering an immunostimulatory nucleic acid to the subject, wherein administration of the immunostimulatory nucleic acid prevents the side effects associated with the high dose of the asthma/allergy medicament. The method provides a basis for administering higher therapeutic doses of an asthma/allergy medicament to a subject in order to prevent or reduce the symptoms associated with an asthmatic or an allergic response more sufficiently than a lower dose. It is not desirable to administer such high doses alone, in the absence of the immunostimulatory nucleic acid, because of the side effects resulting from the high dose.

In another aspect, the invention includes a method for decreasing the dose of an asthma/allergy medicament by administering to a subject having asthma or allergy or at risk of developing asthma or allergy an asthma/allergy medicament in a sub-therapeutic dosage and an immunostimulatory nucleic acid, wherein the combination of the sub-therapeutic dose of the asthma/allergy medicament and the immunostimulatory nucleic acid produce a therapeutic result in the prevention or treatment of asthma or allergy in the subject. The method allows a lower dose of the asthma/allergy medicament to be used. This provides several advantages, including lower costs associated with using less drugs and less chances of inducing side effects resulting from the medications by using lower doses.

According to other aspects, the invention involves methods for treating or preventing asthma and/or allergy by administering an immunostimulatory nucleic acid and an asthma/allergy medicament in different dosing schedules. In one aspect, the invention is a method for preventing or treating asthma or allergy by administering to a subject an effective amount of an immunostimulatory nucleic acid in an effective amount for producing the immune response and subsequently administering to the subject an asthma/allergy medicament. In other aspects, the invention is a method for preventing or treating asthma or allergy by administering to a subject an allergy/asthma medicament in an effective amount for providing some symptomatic relief and subsequently administering an immunostimulatory nucleic acid to the subject. In some embodiments, the immunostimulatory nucleic acid is administered in an effective amount for redirecting the immune response from a Th2 to a Th1 immune response. In some embodiments, the immunostimulatory nucleic acid is administered consistently over a period of time, such as, for instance, in a sustained release vehicle.

In another aspect of the invention is a method for treating asthma or allergy by administering to a subject having asthma or allergy or at risk of developing asthma or allergy an immunostimulatory nucleic acid and an asthma/allergy medicament, wherein the immunostimulatory nucleic acid is administered systemically and the asthma/allergy medicament is administered locally. In yet another aspect, the immunostimulatory nucleic acid is administered locally and the asthma/allergy medicament is administered systemically.

According to yet another aspect of the invention, a method for treating or preventing asthma/allergy is provided. The method is accomplished by administering to a subject having asthma or allergy or at risk of developing asthma or allergy, an immunostimulatory nucleic acid and an asthma/allergy medicament on a routine schedule. In some embodiments, the routine schedule is a daily, weekly, monthly, or quarterly administration of the medicaments. In other embodiments, the immunostimulatory nucleic acid and/or the asthma/allergy medicament is administered in two or more doses.

The immunostimulatory nucleic acid can be administered on a recurring basis, such as daily, weekly, or monthly in one or more doses. Alternatively, it can be administered on a non-regular basis e.g. whenever symptoms being. In yet other embodiments, the asthma/allergy medicament is a quick relief asthma/allergy medicament and in other embodiments it is a long-lasting asthma/allergy medicament.

According to yet another aspect of the invention, methods for treating or preventing asthma or allergy using specific immunostimulatory nucleic acid molecules are provided. The method in one aspect involves a method for preventing or treating asthma or allergy by administering to a subject suffering from asthma or allergy or at risk of developing asthma or allergy, an immunostimulatory nucleic acid having a sequence selected from the group consisting of SEQ ID NO:1 through to SEQ ID NO:1093 and administering to the subject an asthma/allergy medicament.

In yet another aspect of the invention, a method for preventing or treating asthma or allergy utilizing different routes of administration is provided. In one aspect, the method involves the step of administering to a subject having asthma or allergy or at risk of developing asthma or allergy, an immunostimulatory nucleic acid, wherein the immunostimulatory is administered systemically and wherein the asthma/allergy medicament is administered locally. In a related embodiment, the immunostimulatory nucleic acid molecule may be administered locally and the asthma/allergy medicament is administered systemically. In still other embodiments, the immunostimulatory nucleic acid and the asthma/allergy medicament are administered by the same route (i.e., both delivered locally or both delivered systemically), and optionally at the same time.

The invention according to another aspect is a method of preventing or treating asthma or allergy by administering a poly-G nucleic acid, in an effective amount for treating or preventing asthma or allergy. In some embodiments the poly-G nucleic acid is administered alone and in other embodiments the poly-G nucleic acid is administered in conjunction with an asthma/allergy medicament. The poly-G nucleic acid in preferred embodiments comprises one of the following formulas: 5' $X_1X_2GGGX_3X_4$3', wherein $X_1$, $X_2$, $X_3$, and X4 are nucleotides, 5' GGGNGGG 3' or 5' GGGNGGGNGGG 3', wherein N represents between 0 and 20 nucleotides. In some embodiments at least one of $X_3$ and $X_4$ are a G and in other embodiments both of $X_3$ and $X_4$ are a G. Accordingly, in some embodiments, the poly-G nucleic acid may comprise a sequence of 5'$X_1X_2GGGGX_4$3'. In still other embodiments, the poly-G nucleic acid is one which is rich in G (e.g., six out of seven bases are G, or six out of eight bases are G).

The poly-G may be free of unmethylated CG dinucleotides, or may include at least one unmethylated CG dinucleotide.

The poly G nucleic acid in some embodiments is selected from the group consisting of SEQ ID NO: 5, 6, 73, 215, 267-269, 276, 282, 288, 297-299, 355, 359, 386, 387, 444, 476, 531, 557-559, 733, 768, 795, 796, 914-925, 928-931, 933-936, and 938. In other embodiments the poly G nucleic acid includes a sequence selected from the group consisting of SEQ ID NO: 67, 80-82, 141, 147, 148, 173, 178, 183, 185, 214, 224, 264, 265, 315, 329, 434, 435, 475, 519, 521-524, 526, 527, 535, 554, 565, 609, 628, 660, 661, 662, 725, 767, 825, 856, 857, 876, 892, 909, 926, 927, 932, and 937.

The invention provides, in yet another aspect, a method for treating or preventing asthma or allergy in a hypo-responsive subject. The method involves administering to a hypo-responsive subject having asthma or allergy or at risk of developing asthma or allergy an immunostimulatory nucleic acid. In one embodiment, the method further comprises administering to the hypo-responsive subject an asthma/allergy medicament. If the asthma/allergy medicament is not administered to the hypo-responsive subject, then the immunostimulatory nucleic acid is administered in an amount to treat or prevent the asthma or allergy. If the asthma/allergy medicament is administered to the hypo-responsive subject, then the immunostimulatory nucleic acid and the asthma/allergy medicament are administered in an effective amount to treat or prevent the asthma or allergy. In this latter instance, the amount of the immunostimulatory nucleic acid and the amount of the asthma/allergy medicament may be insufficient (i.e., ineffective) in treating or preventing the asthma or allergy if administered alone. In other words, in some embodiments, the immunostimulatory nucleic acid may be administered to the hypo-responsive subject in a sub-therapeutic amount. Similarly, the asthma/allergy medicament may also be administered in a sub-therapeutic amount. However, the combination of the immunostimulatory nucleic acid and the asthma/allergy medicament allows for lower doses of one or both in order to treat or prevent the asthma or allergy. The immunostimulatory nucleic acid may be administered concurrently with the asthma/allergy medicament, but need not be.

The hypo-responsive subject may be one who is hypo-responsive to an asthma/allergy medicament. In one embodiment, the hypo-responsive subject is selected from the group consisting of a subject who is refractory to an asthma/allergy medicament, a subject who is a non-responder to an asthma/allergy medicament, an elderly subject and a neonatal subject.

According to yet another aspect of the invention, a method is provided for preventing asthma or allergy in a subject at risk of developing asthma or allergy which involves administering to a subject at risk of developing asthma or allergy an effective amount of an immunostimulatory nucleic acid substantially prior to an asthmatic or an allergic event.

In one embodiment, the immunostimulatory nucleic acid is administered at least three months, at least two months, at least one month, or at least 20 days prior to the asthmatic or allergic event. In another embodiment, the immunostimulatory nucleic acid is administered at least two weeks prior to the asthmatic or allergic event. In yet another embodiment, the immunostimulatory nucleic acid is administered at least 10 days, at least 5 days or at least 2 days prior to the asthmatic or allergic event.

In one embodiment, the asthmatic or allergic event is selected from the group consisting of an asthma attack, seasonal allergic rhinitis, and perennial allergic rhinitis.

In one embodiment, the immunostimulatory nucleic acid is administered in a routine schedule. In a related embodiment, the routine schedule is selected from the group consisting of a daily routine, a weekly routine, a bi-weekly routine, a monthly routine, and a bimonthly routine.

In a further aspect, the invention provides another method for decreasing a dose of an asthma/allergy medicament. The method involves administering to a subject at risk of developing asthma or allergy, substantially prior to an asthmatic or allergic event, an immunostimulatory nucleic acid in an amount to decrease an effective amount of an asthma/allergy medicament subsequently administered to the subject in order to treat the asthma or allergy.

In one embodiment, the immunostimulatory nucleic acid is administered at least three months, at least two months, at least one month or at least 20 days prior to the asthmatic or allergic event. In another embodiment, the immunostimulatory nucleic acid is administered at least two weeks, at least 10 days, at least one week, at least 5 days or at least 2 days prior to the asthmatic or allergic event.

In one embodiment, the asthmatic or allergic event is selected from the group consisting of an asthma attack, seasonal allergic rhinitis, and perennial allergic rhinitis.

In one embodiment, the immunostimulatory nucleic acid is administered in a routine schedule. The routine schedule may be selected from the group consisting of a daily routine, a weekly routine, a bi-weekly routine, a monthly routine, and a bimonthly routine.

The method may further comprise administering to the subject the asthma/allergy medicament subsequent to the administration of the immunostimulatory nucleic acid. In one embodiment, the asthma/allergy medicament is administered immediately prior to, concurrently with, or following the asthmatic or allergic event. The method may further comprise administering the immunostimulatory nucleic acid concurrently with or following the asthmatic or allergic event. In one embodiment, the immunostimulatory nucleic acid is administered concurrently with the asthma/allergy medicament. In one embodiment, the asthma/allergy medicament is administered in a sub-therapeutic dose.

In these and other aspects of the invention, the immunostimulatory nucleic acids have a number of attributes. The immunostimulatory nucleic acids may have a modified backbone. In some embodiments, the modified backbone is a phosphate modified backbone, and in related embodiments, the phosphate modified backbone is a phosphorothioate backbone. In certain embodiments, the immunostimulatory nucleic acid is a CpG nucleic acid, in other embodiments, the immunostimulatory nucleic acid is a T-rich nucleic acid, while in still other embodiments, the immunostimulatory nucleic acid is a poly-G nucleic acid. Preferably, the T-rich and poly-G nucleic acids are also CpG nucleic acids. In still other embodiments, the immunostimulatory nucleic acid comprises a poly-G motif (e.g., 5' GGGG 3') and a palindrome. Preferably, the immunostimulatory nucleic acid comprises two poly-G motifs, one 5' and one 3' to a centrally located palindrome sequence. Even more preferably, the backbone of these latter immunostimulatory nucleic acids is chimeric (i.e., it is partially, but not completely, composed of phosphorothioate linkages). In some embodiments, a plurality of immunostimulatory nucleic acids is administered, wherein the plurality comprises CpG nucleic acids and T-rich nucleic acids, or CpG nucleic acids and poly-G nucleic acids, or T-rich nucleic acids and poly-G nucleic acids.

In these and other aspects of the invention, the asthma/allergy medicaments have a number of attributes. In some embodiments, the asthma/allergy medicament is an asthma medicament, while in still other embodiments, the asthma/allergy medicament is an allergy medicament.

In some embodiments, the asthma/allergy medicament is selected from the group consisting of a steroid and an immunomodulator. In certain embodiments, the steroid may be selected from the group consisting of beclomethasone, fluticasone, tramcinolone, budesonide, and budesonide. In certain embodiments, the immunomodulator may be selected from the group consisting of an anti-inflammatory agent, a leukotriene antagonist, an IL-4 mutein, a soluble IL-4 receptor, an immunosuppressant, anti-IL-4 antibody, an IL-4 antagonist, an anti-IL-5 antibody, a soluble IL-13 receptor-Fc fusion protein, an anti-IL-9 antibody, a CCR3 antagonist, a CCR5 antagonist, a VLA-4 inhibitor, and a downregulator of IgE. The downregulator of IgE may be an anti-Ig antibody or a fragment thereof, but need not be so limited. The immunosuppressant may be a tolerizing peptide vaccine, but need not be so limited.

In some embodiments, the asthma/allergy medicament is a medicament selected from the group consisting of a PDE-4 inhibitor, a bronchodilator/beta-2 agonist, a K+ channel opener, a VLA-4 antagonist, a neurokin antagonist, a TXA2 synthesis inhibitor, Xanthanine, an arachidonic acid antagonist, a 5 lipoxygenase inhibitor, a thromboxin A2 receptor antagonist, a thromboxane A2 antagonist, an inhibitor of 5-lipox activation protein, and a protease inhibitor. In certain embodiments, the bronchodilator/beta-2 agonist may be selected from the group consisting of salmeterol, salbutamol, terbutaline, D2522/formoterol, fenoterol and orciprenaline.

In some embodiments, the asthma/allergy medicament is a medicament selected from the group consisting of an anti-histamine and a prostaglandin inducer. In certain embodiments, the anti-histamine is selected from the group consisting of loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560 and HSR 609. The prostaglandin inducer may be S-5751, but is not so limited.

In still other embodiments, the asthma/allergy medicament is a prostaglandin inhibitor in the form of a cyclooxygenase-2 (COX-2) inhibitor. The COX-2 inhibitor may be selected from the group consisting of celecoxib, rofecoxib, NS-398, 1-745,337, meloxicam, nimesulide, SC236, and C-phycocyanin.

A composition comprising a poly-G nucleic acid in an aerosol formulation is provided according to other aspects of the invention.

A kit is provided according to another aspect of the invention. The kit in one aspect includes a sustained-release vehicle containing an immunostimulatory nucleic acid and at least one container housing an asthma/allergy medicament, and instructions for timing of administration of the immunostimulatory nucleic acid and the asthma/allergy medicament. In another aspect, the kit includes containers for multiple administrations of immunostimulatory nucleic acid and/or multiple administrations of immunostimulatory nucleic acid and at least one container housing an asthma/allergy medicament.

A composition is provided according to another aspect of the invention. The composition includes an immunostimulatory nucleic acid and an asthma/allergy medicament, formulated in a pharmaceutically-acceptable carrier and in an effective amount for preventing or treating an immune response associated with exposure to a mediator of asthma or allergy.

Formulations of poly-G nucleic acids are also encompassed by the invention. For instance the invention includes a pharmaceutical composition of a poly-G nucleic acid in an aerosol formulation.

The immunostimulatory nucleic acid may be any of the immunostimulatory nucleic acids described above, and may have any of the attributes of the immunostimulatory nucleic acids described above which are useful in other aspects of the invention.

The asthma/allergy medicament may be any of the asthma medicaments or allergy medicaments described above which are useful in other aspects of the invention.

Each of the limitations of the invention can encompass various embodiments of the invention. It is, therefore, anticipated that each of the limitations of the invention involving any one element or combinations of elements can be included in each aspect of the invention.

DETAILED DESCRIPTION OF THE INVENTION

The invention relates to methods and products for the treatment of asthma/allergy using a combination of immunostimulatory nucleic acids and asthma/allergy medicaments. The compositions can be administered in higher doses without as many side effects as are ordinarily achieved at those dosage levels or in lower doses with higher efficacy than is ordinarily achieved with those doses. The compositions can also be administered on fixed schedules or in different temporal relationships to one another. The various combinations have many advantages over the prior art methods of treating asthma and allergy.

One method for treating or preventing asthma or allergy includes the step of administering a synergistic combination of an immunostimulatory nucleic acid and an asthma/allergy medicament in an effective amount to treat or prevent the asthma or allergy.

An "immunostimulatory nucleic acid" as used herein is any nucleic acid containing an immunostimulatory motif or backbone that induces a Th1 immune response and/or suppresses a Th2 immune response. Immunostimulatory motifs include, but are not limited to, CpG motifs, poly-G motifs, and T-rich motifs. Immunostimulatory backbones include, but are not limited to, phosphate modified backbones, such as phosphorothioate backbones. Immunostimulatory nucleic acids have been described extensively in the prior art and a brief summary of these nucleic acids is presented below.

The immunostimulatory nucleic acids when combined with the asthma/allergy medicaments have many advantages over each composition alone for the treatment of asthma and allergy. The immunostimulatory nucleic acid functions in some aspects by simultaneously suppressing Th2-type immune responses (IL-4, IgE production, histamine release) that can result in airway inflammation and bronchial spasm, and/or inducing Th1-type immune responses (IFN-γ and IL-12 production) that promote harmless antibody and cellular responses. This creates an environment inside the body that safely and effectively prevents hypersensitive reactions from occurring, thereby eliminating symptoms.

The immunostimulatory nucleic acids eliminate/reduce bronchial hyperreactivity, bronchoconstriction, bronchial obstruction, airway inflammation and atopy (which improves asthma control, normalizes lung function, prevents irreversible airway injury); and may also inhibit acute response to exercise, cold dry air, and $SO_2$ The nucleic acids provide long-lasting effects, thus reducing dosing regimes, improving compliance and maintenance therapy, reducing emergency situations; and improving quality of life. These compounds are also useful because they provide early anti-infective activity, which leads to decreasing infectious episodes, which further reduces hyperreactive immune responses. This is especially true in subjects like children or immuno-compromised subjects. Furthermore, use of the immunostimulatory nucleic acids reduces/eliminates use of inhalers, which can exacerbate hypersensitive reactions by providing simpler and safer delivery and by allowing less drugs to be used.

Immunostimulatory nucleic acids stimulate the immune system to prevent or treat allergy and/or asthma. The strong yet balanced, cellular and humoral immune responses that result from the nucleic acid's stimulation reflect the body's own natural defense system against invading allergens and initiators.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acids include vectors, e.g., plasmids as well as oligonucleotides. Nucleic acid molecules can be obtained from existing nucleic acid sources (e.g. genomic or cDNA), but are preferably synthetic (e.g. produced by oligonucleotide synthesis).

Exemplary immunostimulatory nucleic acids as those described herein as well as various control nucleic acids include but are not limited to those presented in Table 1.

TABLE 1

| SEQ ID NO: | ODN SEQUENCE | BACKBONE |
|---|---|---|
| 1 | tctcccagcgtgcgccat | s |
| 2 | ataatccagcttgaaccaag | s |
| 3 | ataatcgacgttcaagcaag | s |
| 4 | taccgcgtgcgaccctct | s |
| 5 | ggggagggt | s |
| 6 | ggggaggggg | s |
| 7 | ggtgaggtg | s |
| 8 | tccatgtzgttcctgatgct | o |
| 9 | gctaccttagzgtga | o |
| 10 | tccatgazgttcctgatgct | o |
| 11 | tccatgacgttcztgatgct | o |
| 12 | gctagazgttagtgt | o |
| 13 | agctccatggtgctcactg | s |
| 14 | ccacgtcgaccctcaggcga | s |
| 15 | gcacatcgtcccgcagccga | s |
| 16 | gtcactcgtggtacctcga | s |
| 17 | gttggatacaggccagactttgttg | o |
| 18 | gattcaacttgcgctcatcttaggc | o |
| 19 | accatggacgaactgtttcccctc | s |
| 20 | accatggacgagctgtttcccctc | s |
| 21 | accatggacgacctgtttcccctc | s |
| 22 | accatggacgtactgtttcccctc | s |
| 23 | accatggacggtctgtttcccctc | s |
| 24 | accatggacgttctgtttcccctc | s |
| 25 | ccactcacatctgctgctccacaag | o |
| 26 | acttctcatagtccctttggtccag | o |
| 27 | tccatgagcttcctgagtct | o |
| 28 | gaggaaggigiggaigacgt | o |
| 29 | gtgaaticgttcicgggict | o |
| 30 | aaaaaa | s |
| 31 | cccccc | s |
| 32 | ctgtca | s |
| 33 | tcgtag | s |
| 34 | tcgtgg | s |
| 35 | cgtcgt | s |
| 36 | tccatgtcggtcctgagtct | sos |
| 37 | tccatgccggtcctgagtct | sos |
| 38 | tccatgacggtcctgagtct | sos |
| 39 | tccatgacggtcctgagtct | sos |
| 40 | tccatgtcgatcctgagtct | sos |
| 41 | tccatgtcgctcctgagtct | sos |
| 42 | tccatgtcgttcctgagtct | sos |
| 43 | tccatgacgttcctgagtct | sos |
| 44 | tccataacgttcctgagtct | sos |
| 45 | tccatgacgtccctgagtct | sos |
| 46 | tccatcacgtgcctgagtct | sos |
| 47 | tccatgctggtcctgagtct | sos |
| 48 | tccatgtzggtcctgagtct | sos |
| 49 | ccgcttcctccagatgagctcatgggtttctccaccaag | o |
| 50 | cttggtggagaaacccatgagctcatctggaggaagcgg | o |
| 51 | ccccaaagggatgagaagtt | o |
| 52 | agatagcaaatcggctgacg | o |
| 53 | ggttcacgtgctcatggctg | o |
| 54 | tctcccagcgtgcgccat | s |
| 55 | tctcccagcgtgcgccat | s |
| 56 | taccgcgtgcgaccctct | s |
| 57 | ataatccagcttgaaccaag | s |
| 58 | ataatcgacgttcaagcaag | s |
| 59 | tccatgattttcctgatttt | o |
| 60 | ttgttttttttgttttttttgttttt | s |
| 61 | tttttttttgttttttttgttttt | o |
| 62 | tgctgcttttgtgcttttgtgctt | s |
| 63 | tgctgcttgtgcttttgtgctt | o |
| 64 | gcattcatcaggcgggcaagaat | o |
| 65 | taccgagcttcgacgagatttca | o |

TABLE 1-continued

| SEQ ID NO: | ODN SEQUENCE | BACKBONE |
|---|---|---|
| 66 | gcatgacgttgagct | s |
| 67 | cacgttgagggcat | s |
| 68 | ctgctgagactggag | s |
| 69 | tccatgacgttcctgacgtt | s |
| 70 | gcatgagcttgagctga | o |
| 71 | tcagcgtgcgcc | s |
| 72 | atgacgttcctgacgtt | s |
| 73 | ttttggggttttggggtttt | s |
| 74 | tctaggcttttaggcttcc | s |
| 75 | tgcattttttaggccaccat | s |
| 76 | tctcccagcgtgcgtgcgccat | s |
| 77 | tctcccagcgggcgcat | s |
| 78 | tctcccagcgagcgccat | s |
| 79 | tctcccagcgcgcgccat | s |
| 80 | ggggtgacgttcaggggg | sos |
| 81 | ggggtccagcgtgcgccatggggg | sos |
| 82 | ggggtgtcgttcaggggg | sos |
| 83 | tccatgtcgttcctgtcgtt | s |
| 84 | tccatagcgttcctagcgtt | s |
| 85 | tcgtcgctgtctccgcttctt | s |
| 86 | gcatgacgttgagct | sos |
| 87 | tctcccagcgtgcgccatat | sos |
| 88 | tccatgazgttcctgazgtt | s |
| 89 | gcatgazgttgagct | o |
| 90 | tccagcgtgcgccata | sos |
| 91 | tctcccagcgtgcgccat | o |
| 92 | tccatgagcttcctgagtct | o |
| 93 | gcatgtcgttgagct | sos |
| 94 | tcctgacgttcctgacgtt | s |
| 95 | gcatgatgttgagct | o |
| 96 | gcatttcgaggagct | o |
| 97 | gcatgtagctgagct | o |
| 98 | tccaggacgttcctagttct | o |
| 99 | tccaggagcttcctagttct | o |
| 100 | tccaggatgttcctagttct | o |
| 101 | tccagtctaggcctagttct | o |
| 102 | tccagttcgagcctagttct | o |
| 103 | gcatggcgttgagct | sos |
| 104 | gcatagcgttgagct | sos |
| 105 | gcattgcgttgagct | sos |
| 106 | gcttgcgttgcgttt | sos |
| 107 | tctcccagcgttgcgccatat | sos |
| 108 | tctcccagcgtgcgttatat | sos |
| 109 | tctccctgcgtgcgccatat | sos |
| 110 | tctgcgtgcgtgcgccatat | sos |
| 111 | tctcctagcgtgcgccatat | sos |
| 112 | tctcccagcgtgcgcctttt | sos |
| 113 | gctandcghhagc | o |
| 114 | tcctgacgttccc | o |
| 115 | ggaagacgttaga | o |
| 116 | tcctgacgttaga | o |
| 117 | tcagaccagctggtcgggtgttcctga | o |
| 118 | tcaggaacacccgaccagctggtctga | o |
| 119 | gctagtcgatagc | o |
| 120 | gctagtcgctagc | o |
| 121 | gcttgacgtctagc | o |
| 122 | gcttgacgtttagc | o |
| 123 | gcttgacgtcaagc | o |
| 124 | gctagacgtttagc | o |
| 125 | tccatgacattcctgatgct | o |
| 126 | gctagacgtctagc | o |
| 127 | ggctatgtcgttcctagcc | o |
| 128 | ggctatgtcgatcctagcc | o |
| 129 | ctcatgggtttctccaccaag | o |
| 130 | cttggtggagaaacccatgag | o |
| 131 | tccatgacgttcctagttct | o |
| 132 | ccgcttcctccagatgagctcatg | o |
| 133 | catgagctcatctggaggaagcgg | o |
| 134 | ccagatgagctcatgggtttctcc | o |
| 135 | ggagaaacccatgagctcatctgg | o |
| 136 | agcatcaggaacgacatgga | o |
| 137 | tccatgacgttcctgacgtt | rna |
| 138 | gcgcgcgcgcgcgcgcg | o |
| 139 | ccggccggccggccgg | o |
| 140 | ttccaatcagccccacccgctctggccccaccctcaccctcca | o |
| 141 | tggagggtgagggtggggccagagcgggtggggctgattggaa | o |
| 142 | tcaaatgtgggattttcccatgagtct | o |

TABLE 1-continued

| SEQ ID NO: | ODN SEQUENCE | BACKBONE |
|---|---|---|
| 143 | agactcatgggaaaatcccacatttga | o |
| 144 | tgccaagtgctgagtcactaataaaga | o |
| 145 | tctttattagtgactcagcacttggca | o |
| 146 | tgcaggaagtccgggttttccccaaccccc | o |
| 147 | gggggggttggggaaaacccggacttcctgca | o |
| 148 | ggggacttttccgctggggacttttccaggggactttcc | sos |
| 149 | tccatgacgttcctctccatgacgttcctctccatgacgttcctc | o |
| 150 | gaggaacgtcatggagaggaacgtcatggagaggaacgtcatgga | o |
| 151 | ataatagagcttcaagcaag | s |
| 152 | tccatgacgttcctgacgtt | s |
| 153 | tccatgacgttcctgacgtt | sos |
| 154 | tccaggactttcctcaggtt | s |
| 155 | tcttgcgatgctaaaggacgtcacattgcacaatcttaataaggt | o |
| 156 | accttattaagattgtgcaatgtgacgtcctttagcatcgcaaga | o |
| 157 | tcctgacgttcctggcggtcctgtcgct | o |
| 158 | tcctgtcgctcctgtcgct | o |
| 159 | tcctgacgttgaagt | o |
| 160 | tcctgtcgttgaagt | o |
| 161 | tcctggcgttgaagt | o |
| 162 | tcctgccgttgaagt | o |
| 163 | tccttacgttgaagt | o |
| 164 | tcctaacgttgaagt | o |
| 165 | tcctcacgttgaagt | o |
| 166 | tcctgacgatgaagt | o |
| 167 | tcctgacgctgaagt | o |
| 168 | tcctgacggtgaagt | o |
| 169 | tcctgacgtagaagt | o |
| 170 | tcctgacgtcgaagt | o |
| 171 | tcctgacgtggaagt | o |
| 172 | tcctgagcttgaagt | o |
| 173 | gggggacgttggggg | o |
| 174 | tcctgacgttccttc | o |
| 175 | tctcccagcgagcgagcgccat | s |
| 176 | tcctgacgttccctggcggtccctgtcgct | o |
| 177 | tcctgtcgctcctgtcgctcctgtcgct | o |
| 178 | tcctggcggggaagt | o |
| 179 | tcctgazgttgaagt | o |
| 180 | tcztgacgttgaagt | o |
| 181 | tcctagcgttgaagt | o |
| 182 | tccagacgttgaagt | o |
| 183 | tcctgacggggaagt | o |
| 184 | tcctggcggtgaagt | o |
| 185 | ggctccggggagggaattttttgtctat | o |
| 186 | atagacaaaaattccctccccggagcc | o |
| 187 | tccatgagcttccttgagtct | rna |
| 188 | tcgtcgctgtctccgcttctt | so |
| 189 | tcgtcgctgtctccgcttctt | s20 |
| 190 | tcgagacattgcacaatcatctg | o |
| 191 | cagattgtgcaatgtctcga | o |
| 192 | tccatgtcgttcctgatgcg | o |
| 193 | gcgatgtcgttcctgatgct | o |
| 194 | gcgatgtcgttcctgatgcg | o |
| 195 | tccatgtcgttccgcgcgcg | o |
| 196 | tccatgtcgttcctgccgct | o |
| 197 | tccatgtcgttcctgtagct | o |
| 198 | gcggcgggcggcgcgcgccc | o |
| 199 | atcaggaacgtcatgggaagc | o |
| 200 | tccatgagcttcctgagtct | p-ethoxy |
| 201 | tcaacgtt | p-ethoxy |
| 202 | tcaagctt | p-ethoxy |
| 203 | tcctgtcgttcctgtcgtt | s |
| 204 | tccatgtcgttttgtcgtt | s |
| 205 | tcctgtcgttccttgtcgtt | s |
| 206 | tccttgtcgttcctgtcgtt | s |
| 207 | btccattccatgacgttcctgatgcttcca | os |
| 208 | tcctgtcgttttttgtcgtt | s |
| 209 | tcgtcgctgtctccgcttctt | s |
| 210 | tcgtcgctgtctgcccttctt | s |
| 211 | tcgtcgctgttgtcgttttctt | s |
| 212 | tcctgtcgttcctgtcgttggaacgacagg | o |
| 213 | tcctgtcgttcctgtcgtttcaacgtcaggaacgacagga | o |
| 214 | ggggtctgtcgttttggggg | sos |
| 215 | ggggtctgtgcttttggggg | sos |
| 216 | tccggccgttgaagt | o |
| 217 | tccggacggtgaagt | o |
| 218 | tcccgccgttgaagt | o |
| 219 | tccagacggtgaagt | o |

TABLE 1-continued

| SEQ ID NO: | ODN SEQUENCE | BACKBONE |
|---|---|---|
| 220 | tcccgacggtgaagt | o |
| 221 | tccagagcttgaagt | o |
| 222 | tccatgtzgttcctgtzgtt | s |
| 223 | tccatgacgttcctgacgtt | sos |
| 224 | ggggttgacgttttggggg | sos |
| 225 | tccaggacttctctcaggtt | s |
| 226 | tttttttttttttttttttt | s |
| 227 | tccatgccgttcctgccgtt | s |
| 228 | tccatggcgggcctggcggg | s |
| 229 | tccatgacgttcctgccgtt | s |
| 230 | tccatgacgttcctggcggg | s |
| 231 | tccatgacgttcctgcgttt | s |
| 232 | tccatgacggtcctgacggt | s |
| 233 | tccatgcgtgcgtgcgtttt | s |
| 234 | tccatgcgttgcgttgcgtt | s |
| 235 | btccattccattctaggcctgagtcttccat | os |
| 236 | tccatagcgttcctagcgtt | o |
| 237 | tccatgtcgttcctgtcgtt | o |
| 238 | tccatagcgatcctagcgat | o |
| 239 | tccattgcgttccttgcgtt | o |
| 240 | tccatagcggtcctagcggt | o |
| 241 | tccatgattttcctgcagttcctgatttt | |
| 242 | tccatgacgttcctgcagttcctgacgtt | s |
| 243 | ggcggcggcggcggcggcgg | o |
| 244 | tccacgacgttttcgacgtt | s |
| 245 | tcgtcgttgtcgttgtcgtt | s |
| 246 | tcgtcgttttgtcgttttgtcgtt | s |
| 247 | tcgtcgttgtcgttttgtcgtt | s |
| 248 | gcgtgcgttgtcgttgtcgtt | s |
| 249 | czggczggczgggczccgg | o |
| 250 | gcggcgggcggcgcgcgccc | s |
| 251 | agicccgigaacgiattcac | o |
| 252 | tgtcgtttgtcgtttgtcgtt | s |
| 253 | tgtcgttgtcgttgtcgttgtcgtt | s |
| 254 | tgtcgttgtcgttgtcgttgtcgtt | s |
| 255 | tcgtcgtcgtcgtt | s |
| 256 | tgtcgttgtcgtt | s |
| 257 | cccccccccccccccccccc | s |
| 258 | tctagcgttttagcgttcc | sos |
| 259 | tgcatccccaggccaccat | s |
| 260 | tcgtcgtcgtcgtcgtcgtt | sos |
| 261 | tcgtcgttgtcgttgtcgtt | sos |
| 262 | tcgtcgttttgtcgttttgtcgtt | sos |
| 263 | tcgtcgttgtcgttttgtcgtt | sos |
| 264 | ggggagggaggaacttcttaaaattcccccagaatgttt | o |
| 265 | aaacattctgggggaattttaagaagttcctccctcccc | o |
| 266 | atgtttacttcttaaaattcccccagaatgttt | o |
| 267 | aaacattctgggggaattttaagaagtaaacat | o |
| 268 | atgtttactagacaaaattcccccagaatgttt | o |
| 269 | aaacattctgggggaattttgtctagtaaacat | o |
| 270 | aaaattgacgttttaaaaaa | sos |
| 271 | cccccttgacgttttccccc | sos |
| 272 | ttttcgttgtttttgtcgtt | |
| 273 | tcgtcgttttgtcgttttgtcgtt | sos |
| 274 | ctgcagcctgggac | o |
| 275 | acccgtcgtaattatagtaaaaccc | o |
| 276 | ggtacctgtggggacattgtg | o |
| 277 | agcaccgaacgtgagagg | o |
| 278 | tccatgccgttcctgccgtt | o |
| 279 | tccatgacggtcctgacggt | o |
| 280 | tccatgccggtcctgccggt | o |
| 281 | tccatgcgcgtcctgcgcgt | o |
| 282 | ctggtctttctggttttttctgg | s |
| 283 | tcaggggtgggggaacctt | sos |
| 284 | tccatgazgttcctagttct | o |
| 285 | tccatgatgttcctagttct | o |
| 286 | cccgaagtcatttcctcttaacctgg | o |
| 287 | ccaggttaagaggaaatgacttcggg | o |
| 288 | tcctggzggggaagt | o |
| 289 | gzggzgggzggzgzgzgccc | x |
| 290 | tccatgtgcttcctgatgct | o |
| 291 | tccatgtccttcctgatgct | |
| 292 | tccatgtcgttcctagttct | |
| 293 | tccaagtagttcctagttct | o |
| 294 | tccatgtagttcctagttct | o |
| 295 | tcccgcgcgttccgcgcgtt | s |
| 296 | tcctggcggtcctggcggtt | s |

TABLE 1-continued

| SEQ ID NO: | ODN SEQUENCE | BACKBONE |
|---|---|---|
| 297 | tcctggaggggaagt | o |
| 298 | tcctgggggggaagt | o |
| 299 | tcctggtggggaagt | o |
| 300 | tcgtcgttttgtcgttttgtcgtt | o |
| 301 | ctggtcttttctggttttttctgg | o |
| 302 | tccatgacgttcctgacgtt | o |
| 303 | tccaggacttctctcaggtt | sos |
| 304 | tzgtzgttttgtzgttttgtzgtt | o |
| 305 | btcgtcgttttgtcgttttgtcgttttttt | os |
| 306 | gctatgacgttccaaggg | s |
| 307 | tcaacgtt | s |
| 308 | tccaggactttcctcaggtt | o |
| 309 | ctctctgtaggcccgcttgg | s |
| 310 | ctttccgttggaccccctggg | s |
| 311 | gtccgggccaggccaaagtc | s |
| 312 | gtgcgcgcgagcccgaaatc | s |
| 313 | tccatgaigttcctgaigtt | s |
| 314 | aatagtcgccataacaaaac | o |
| 315 | aatagtcgccatggcgggc | o |
| 316 | bttttccatgtcgttcctgatgcttttt | os |
| 317 | tcctgtcgttgaagtttttt | o |
| 318 | gctagctttagagctttagagctt | o |
| 319 | tgctgcttcccccccccccc | o |
| 320 | tcgacgttcccccccccccc | o |
| 321 | tcgtcgttcccccccccccc | o |
| 322 | tcgtcgttcccccccccccc | o |
| 323 | tcgccgttcccccccccccc | o |
| 324 | tcgtcgatcccccccccccc | o |
| 325 | tcctgacgttgaagt | s |
| 326 | tcctgccgttgaagt | s |
| 327 | tcctgacggtgaagt | s |
| 328 | tcctgagcttgaagt | s |
| 329 | tcctggcggggaagt | s |
| 330 | aaaatctgtgcttttaaaaaa | sos |
| 331 | gatccagtcacagtgacctggcagaatctggat | o |
| 332 | gatccagattctgccaggtcactgtgactggat | o |
| 333 | gatccagtcacagtgactcagcagaatctggat | o |
| 334 | gatccagattctgctgagtcactgtgactggat | o |
| 335 | tcgtcgttccccccczcccc | o |
| 336 | tzgtzgttcccccccccccc | o |
| 337 | tzgtcgttcccccccccccc | o |
| 338 | tcgtzgttcccccccccccc | o |
| 339 | tcgtcgctcccccccccccc | o |
| 340 | tcgtcggtcccccccccccc | o |
| 341 | tcggcgttcccccccccccc | o |
| 342 | ggcctttcccccccccccc | o |
| 343 | tcgtcgttttgacgttttgtcgtt | s |
| 344 | tcgtcgttttgacgttttgacgtt | s |
| 345 | ccgtcgttcccccccccccc | o |
| 346 | gcgtcgttcccccccccccc | o |
| 347 | tcgtcattcccccccccccc | o |
| 348 | acgtcgttcccccccccccc | o |
| 349 | ctgtcgttcccccccccccc | o |
| 350 | bttttcgtcgttcccccccccccc | os |
| 351 | tcgtcgttccccccccccccb | o |
| 352 | tcgtcgttttgtcgttttgtcgttb | o |
| 353 | tccagttccttcctcagtct | o |
| 354 | tzgtcgttttgtcgttttgtcgtt | o |
| 355 | tcctggaggggaagt | s |
| 356 | tcctgaaaaggaagt | s |
| 357 | tcgtcgttccccccccc | s |
| 358 | tzgtzgttttgtzgttttgtzgtt | s |
| 359 | ggggtcaagcttgagggggg | sos |
| 360 | tgctgcttcccccccccccc | s |
| 361 | tcgtcgtcgtcgtt | s2 |
| 362 | tcgtcgtcgtcgtt | s20 |
| 363 | tcgtcgtcgtcgtt | os2 |
| 364 | tcaacgttga | s |
| 365 | tcaacgtt | s |
| 366 | atagttttccattttttttac | |
| 367 | aatagtcgccatcgcgcgac | o |
| 368 | aatagtcgccatcccgggac | o |
| 369 | aatagtcgccatccccccc | o |
| 370 | tgctgcttttgtgcttttgtgctt | o |
| 371 | ctgtgcttttctgtgttttctgtg | s |
| 372 | ctaatcttttctaattttttctaa | s |
| 373 | tcgtcgttggtgtcgttggtgtcgtt | s |

TABLE 1-continued

| SEQ ID NO: | ODN SEQUENCE | BACKBONE |
|---|---|---|
| 374 | tcgtcgttggttgtcgttttggtt | s |
| 375 | accatggacgagctgtttcccctc | |
| 376 | tcgtcgttttgcgtgcgttt | s |
| 377 | ctgtaagtgagcttggagag | |
| 378 | gagaacgctggaccttcc | |
| 379 | cgggcgactcagtctatcgg | |
| 380 | gttctcagataaagcggaaccagcaacagacacagaa | |
| 381 | ttctgtgtctgttgctggttccgctttatctgagaac | |
| 382 | cagacacagaagcccgatagacg | |
| 383 | agacagacacgaaacgaccg | |
| 384 | gtctgtcccatgatctcgaa | |
| 385 | gctggccagcttacctcccg | |
| 386 | ggggcctctatacaacctggg | |
| 387 | ggggtccctgagactgcc | |
| 388 | gagaacgctggaccttccat | |
| 389 | tccatgtcggtcctgatgct | |
| 390 | ctcttgcgacctggaaggta | |
| 391 | aggtacagccaggactacga | |
| 392 | accatggacgacctgtttcccctc | |
| 393 | accatggattaccttttcccctt | |
| 394 | atggaaggtccagcgttctc | o |
| 395 | agcatcaggaccgacatgga | o |
| 396 | ctctccaagctcacttacag | |
| 397 | tccctgagactgccccacctt | |
| 398 | gccaccaaaacttgtccatg | |
| 399 | gtccatggcgtgcgggatga | |
| 400 | cctctatacaacctgggac | |
| 401 | cgggcgactcagtctatcgg | |
| 402 | gcgctaccggtagcctgagt | |
| 403 | cgactgccgaacaggatatcggtgatcagcactgg | |
| 404 | ccagtgctgatcaccgatatcctgttcggcagtcg | |
| 405 | ccaggttgtatagaggc | |
| 406 | tctcccagcgtacgccat | s |
| 407 | tctcccagcgtgcgtttt | s |
| 408 | tctcccgacgtgcgccat | s |
| 409 | tctcccgtcgtgcgccat | s |
| 410 | ataatcgtcgttcaagcaag | s |
| 411 | tcgtcgttttgtcgttttgtcgt | s2 |
| 412 | tcgtcgttttgtcgttttgtcgtt | s2 |
| 413 | tcgtcgttttgtcgttttgtcgtt | s2 |
| 414 | tcntcgtnttntcgtnttntcgtn | s |
| 415 | tctcccagcgtcgccat | s |
| 416 | tctcccatcgtcgccat | s |
| 417 | ataatcgtgcgttcaagaaag | s |
| 418 | ataatcgacgttccccccccc | s |
| 419 | tctatcgacgttcaagcaag | s |
| 420 | tcc tga cgg gg agt | s |
| 421 | tccatgacgttcctgatcc | |
| 422 | tccatgacgttcctgatcc | |
| 423 | tccatgacgttcctgatcc | |
| 424 | tcc tgg cgt gga agt | s |
| 425 | tccatgacgttcctgatcc | |
| 426 | tcgtcgctgttgtcgtttctt | s |
| 427 | agcagctttagagctttagagctt | s |
| 428 | cccccccccccccccccccccccc | s |
| 429 | tcgtcgttttgtcgttttgtcgttttgtcgtt | s |
| 430 | tcgtcgttttttgtcgttttttgtcgtt | s |
| 431 | tcgtcgttttttttttttttt | s |
| 432 | tttttcaacgttgattttttt | sos |
| 433 | tttttttttttttttttttttttttt | s |
| 434 | ggggtcgtcgttttgggggg | |
| 435 | tcgtcgttttgtcgtttggggggg | |
| 436 | tcgtcgctgtctccgcttcttcttgcc | |
| 437 | tcgtcgctgtctccg | s |
| 438 | ctgtaagtgagcttggagag | |
| 439 | gagaacgctggaccttccat | |
| 440 | ccaggttgtatagaggc | |
| 441 | gctagacgttagcgtga | |
| 442 | ggagctcttcgaacgccata | |
| 443 | tctccatgatggttttatcg | |
| 444 | aaggtggggcagtctcaggga | |
| 445 | atcggaggactggcgcgccg | |
| 446 | ttaggacaaggtctagggtg | |
| 447 | accacaacgagaggaacgca | |
| 448 | ggcagtgcaggctcaccggg | |
| 449 | gaaccttccatgctgtt | |
| 450 | gctagacgttagcgtga | |

TABLE 1-continued

| SEQ ID NO: | ODN SEQUENCE | BACKBONE |
|---|---|---|
| 451 | gcttggagggcctgtaagtg | |
| 452 | gtagccttccta | |
| 453 | cggtagccttccta | |
| 454 | cacggtagccttccta | |
| 455 | agcacggtagccttccta | |
| 456 | gaacgctggaccttccat | |
| 457 | gaccttccat | |
| 458 | tggaccttccat | |
| 459 | gctggaccttccat | |
| 460 | acgctggaccttccat | |
| 461 | taagctctgtcaacgccagg | |
| 462 | gagaacgctggaccttccatgt | |
| 463 | tccatgtcggtcctgatgct | |
| 464 | ttcatgccttgcaaaatggcg | |
| 465 | tgctagctgtgcctgtacct | |
| 466 | agcatcaggaccgacatgga | |
| 467 | gaccttccatgtcggtcctgat | |
| 468 | acaaccacgagaacgggaac | |
| 469 | gaaccttccatgctgttccg | |
| 470 | caatcaatctgaggagaccc | |
| 471 | tcagctctggtacttttca | |
| 472 | tggttacggtctgtcccatg | |
| 473 | gtctatcggaggactggcgc | |
| 474 | cattttacgggcgggcgggc | |
| 475 | gaggggaccattttacgggc | |
| 476 | tgtccagccgaggggaccat | |
| 477 | cgggcttacggcggatgctg | |
| 478 | tggaccttctatgtcggtcc | |
| 479 | tgtcccatgttttagaagc | |
| 480 | gtggttacggtcgtgcccat | |
| 481 | cctccaaatgaaagaccccc | |
| 482 | ttgtactctccatgatggtt | |
| 483 | ttccatgctgttccggctgg | |
| 484 | gaccttctatgtcggtcctg | |
| 485 | gagaccgctcgaccttcgat | |
| 486 | ttgccccatattttagaaac | |
| 487 | ttgaaactgaggtgggac | |
| 488 | ctatcggaggactggcgcgcc | |
| 489 | cttggagggcctcccggcgg | |
| 490 | gctgaaccttccatgctgtt | |
| 491 | tagaaacagcattcttctttttagggcagcaca | |
| 492 | agatggttctcagataaagcggaa | |
| 493 | ttccgctttatctgagaaccatct | |
| 494 | gtcccaggttgtatagaggctgc | |
| 495 | gcgccagtcctccgatagac | |
| 496 | atcggaggactggcgcgccg | |
| 497 | ggtctgtcccatattttag | SOS |
| 498 | tttttcaacgttgaggggg | SOS |
| 499 | tttttcaagcgttgatttttt | SOS |
| 500 | ggggtcaacgttgattttttt | SOS |
| 501 | ggggttttcaacgttttgaggggggg | SOS |
| 502 | ggttacggtctgtcccatat | |
| 503 | ctgtcccatattttagaca | |
| 504 | accatcctgaggccattcgg | |
| 505 | cgtctatcgggcttctgtgtctg | |
| 506 | ggccatcccacattgaaagtt | |
| 507 | ccaaatatcggtggtcaagcac | |
| 508 | gtgcttgaccaccgatatttgg | |
| 509 | gtgctgatcaccgatatcctgttcgg | |
| 510 | ggccaactttcaatgtgggatggcctc | |
| 511 | ttccgccgaatggcctcaggatggtac | |
| 512 | tatagtccctgagactgccccaccttctcaacaacc | |
| 513 | gcagcctctatacaacctgggacggga | |
| 514 | ctatcggaggactggcgcgccg | |
| 515 | tatcggaggactggcgcgccg | |
| 516 | gatcggaggactggcgcgccg | |
| 517 | ccgaacaggatatcggtgatcagcac | |
| 518 | ttttgggtcaacgttgagggggg | |
| 519 | ggggtcaacgttgaggggg | SOS |
| 520 | cgcgcgcgcgcgcgcgcgcg | S |
| 521 | ggggcatgacgttcgggggg | SS |
| 522 | ggggcatgacgttcaaaaas | S |
| 523 | ggggcatgagcttcgggggg | S |
| 524 | ggggcatgacgttcgggggg | SOS |
| 525 | aaaacatgacgttcaaaaaa | SOS |
| 526 | aaaacatgacgttcggggggg | SOS |
| 527 | ggggcatgacgttcaaaaaa | SOS |

TABLE 1-continued

| SEQ ID NO: | ODN SEQUENCE | BACKBONE |
|---|---|---|
| 528 | accatggacgatctgtttccccctc | s |
| 529 | gccatggacgaactgttccccctc | s |
| 530 | cccccccccccccccccccc | sos |
| 531 | gggggggggggggggggggg | sos |
| 532 | gctgtaaaatgaatcggccg | sos |
| 533 | ttcgggcggactcctccatt | sos |
| 534 | tatgccgcgcccggacttat | sos |
| 535 | ggggtaatcgatcagggggg | sos |
| 536 | tttgagaacgctggaccttc | sos |
| 537 | gatcgctgatctaatgctcg | sos |
| 538 | gtcggtcctgatgctgttcc | sos |
| 539 | tcgtcgtcagttcgctgtcg | sos |
| 540 | ctggaccttccatgtcgg | sos |
| 541 | gctcgttcagcgcgtct | sos |
| 542 | ctggaccttccatgtc | sos |
| 543 | cactgtccttcgtcga | sos |
| 544 | cgctggaccttccatgtcgg | sos |
| 545 | gctgagctcatgccgtctgc | sos |
| 546 | aacgctggaccttccatgtc | sos |
| 547 | tgcatgccgtacacagctct | sos |
| 548 | ccttccatgtcggtcctgat | sos |
| 549 | tactcttcggatcccttgcg | sos |
| 550 | ttccatgtcggtcctgat | sos |
| 551 | ctgattgctctctcgtga | sos |
| 552 | ggcgttattcctgactcgcc | o |
| 553 | cctacgttgtatgcgcccagct | o |
| 554 | ggggtaatcgatgagggggg | o |
| 555 | ttcgggcggactcctccatt | o |
| 556 | tttttttttttttttttttt | o |
| 557 | gggggtttttttttggggg | o |
| 558 | tttttggggggggggttttt | o |
| 559 | gggggggggggggggggggt | o |
| 560 | aaaaaaaaaaaaaaaaaaaa | o |
| 561 | cccccaaaaaaaaaaccccc | o |
| 562 | aaaaaccccccccccaaaaa | o |
| 563 | tttgaattcaggactggtgaggttgag | o |
| 564 | tttgaatcctcagcggtctccagtggc | o |
| 565 | aattctctatcggggcttctgtgtctgttgctggttccgctttat | o |
| 566 | ctagataaagcggaaccagcaacagacacagaagccccgatagag | o |
| 567 | ttttctagagaggtgcacaatgctctgg | o |
| 568 | tttgaattccgtgtacagaagcgagaagc | o |
| 569 | tttgcggccgctagacttaacctgagagata | o |
| 570 | tttgggcccacgagagacagagacacttc | o |
| 571 | tttgggcccgcttctcgcttctgtacacg | o |
| 572 | gagaacgctggaccttccat | s |
| 573 | tccatgtcggtcctgatgct | s |
| 574 | ctgtcg | s |
| 575 | tcgtga | s |
| 576 | cgtcga | s |
| 577 | agtgct | s |
| 578 | ctgtcg | o |
| 579 | agtgct | o |
| 580 | cgtcga | o |
| 581 | tcgtga | o |
| 582 | gagaacgctccagcttcgat | o |
| 583 | gctagacgtaagcgtga | o |
| 584 | gagaacgctcgaccttccat | o |
| 585 | gagaacgctggacctatccat | o |
| 586 | gctagaggttagcgtga | o |
| 587 | gagaacgctggacttccat | o |
| 588 | tcacgctaacgtctagc | o |
| 589 | bgctagacgttagcgtga | o |
| 590 | atggaaggtcgagcgttctc | o |
| 591 | gagaacgctggaccttcgat | o |
| 592 | gagaacgatggaccttccat | o |
| 593 | gagaacgctggatccat | o |
| 594 | gagaacgctccagcactgat | o |
| 595 | tccatgtcggtcctgctgat | o |
| 596 | atgtcctcggtcctgatgct | o |
| 597 | gagaacgctccaccttccat | o |
| 598 | gagaacgctggaccttcgta | o |
| 599 | batggaaggtccagcgttctc | o |
| 600 | tcctga | o |
| 601 | tcaacgtt | o |
| 602 | aacgtt | o |
| 603 | aacgttga | o |
| 604 | tcacgctaacctctagc | o |

TABLE 1-continued

| SEQ ID NO: | ODN SEQUENCE | BACKBONE |
|---|---|---|
| 605 | gagaacgctggaccttgcat | o |
| 606 | gctggaccttccat | o |
| 607 | gagaacgctggacctcatccat | o |
| 608 | gagaacgctggacgctcatccat | o |
| 609 | aacgttgagggcat | o |
| 610 | atgcccctcaacgtt | o |
| 611 | tcaacgttga | o |
| 612 | gctggaccttccat | o |
| 613 | caacgtt | o |
| 614 | acaacgttga | o |
| 615 | tcacgt | o |
| 616 | tcaagctt | o |
| 617 | tcgtca | o |
| 618 | aggatatc | o |
| 619 | tagacgtc | o |
| 620 | gacgtcat | o |
| 621 | ccatcgat | o |
| 622 | atcgatgt | o |
| 623 | atgcatgt | o |
| 624 | ccatgcat | o |
| 625 | agcgctga | o |
| 626 | tcagcgct | o |
| 627 | ccttcgat | o |
| 628 | gtgccggggtctccgggc | o |
| 629 | gctgtgggcggctcctg | s |
| 630 | btcaacgtt | o |
| 631 | ftcaacgtt | o |
| 632 | faacgttga | o |
| 633 | tcaacgt | s |
| 634 | aacgttg | s |
| 635 | cgacga | o |
| 636 | tcaacgtt | o |
| 637 | tcgga | o |
| 638 | agaacgtt | o |
| 639 | tcatcgat | o |
| 640 | taaacgtt | s |
| 641 | ccaacgtt | s |
| 642 | gctcga | s |
| 643 | cgacgt | s |
| 644 | cgtcgt | s |
| 645 | acgtgt | s |
| 646 | cgttcg | s |
| 647 | gagcaagctggaccttccat | s |
| 648 | cgcgta | s |
| 649 | cgtacg | s |
| 650 | tcaccggt | s |
| 651 | caagagatgctaacaatgca | s |
| 652 | acccatcaatagctctgtgc | s |
| 653 | ccatcgat | o |
| 654 | tcgacgtc | o |
| 655 | ctagcgct | o |
| 656 | taagcgct | o |
| 657 | tcgcgaattcgcg | o |
| 658 | atggaaggtccagcgttct | o |
| 659 | actggacgttagcgtga | o |
| 660 | cgcctggggctggtctgg | o |
| 661 | gtgtcggggtctccgggc | o |
| 662 | gtgccggggtctccgggc | o |
| 663 | cgccgtcgcggcggttgg | o |
| 664 | gaagttcacgttgagggcat | o |
| 665 | atctggtgagggcaagctatg | s |
| 666 | gttgaaacccgagaacatcat | s |
| 667 | gcaacgtt | o |
| 668 | gtaacgtt | o |
| 669 | cgaacgtt | o |
| 670 | gaaacgtt | o |
| 671 | caaacgtt | o |
| 672 | ctaacgtt | o |
| 673 | ggaacgtt | o |
| 674 | tgaacgtt | o |
| 675 | acaacgtt | o |
| 676 | ttaacgtt | o |
| 677 | aaaacgtt | o |
| 678 | ataacgtt | o |
| 679 | aacgttct | o |
| 680 | tccgatcg | o |
| 681 | tccgtacg | o |

TABLE 1-continued

| SEQ ID NO: | ODN SEQUENCE | BACKBONE |
|---|---|---|
| 682 | gctagacgctagcgtga | o |
| 683 | gagaacgctggacctcatcatccat | o |
| 684 | gagaacgctagaccttctat | o |
| 685 | actagacgttagtgtga | o |
| 686 | cacaccttggtcaatgtcacgt | o |
| 687 | tctccatcctatggttttatcg | o |
| 688 | cgctggaccttccat | o |
| 689 | caccaccttggtcaatgtcacgt | o |
| 690 | gctagacgttagctgga | o |
| 691 | agtgcgattgcagatcg | o |
| 692 | ttttcgttttgtggttttgtggtt | |
| 693 | ttttcgtttgtcgttttgtcgtt | |
| 694 | tttttgttttgtggttttgtggtt | |
| 695 | accgcatggattctaggcca | s |
| 696 | gctagacgttagcgt | o |
| 697 | aacgctggaccttccat | o |
| 698 | tcaazgtt | o |
| 699 | ccttcgat | o |
| 700 | actagacgttagtgtga | s |
| 701 | gctagaggttagcgtga | s |
| 702 | atggactctccagcgttctc | o |
| 703 | atcgactctcgagcgttctc | o |
| 704 | gctagacgttagc | o |
| 705 | gctagacgt | o |
| 706 | agtgcgattcgagatcg | o |
| 707 | tcagzgct | o |
| 708 | ctgattgctctcgtga | o |
| 709 | tzaacgtt | o |
| 710 | gagaazgctggaccttccat | o |
| 711 | gctagacgttaggctga | o |
| 712 | gctacttagcgtga | o |
| 713 | gctaccttagcgtga | o |
| 714 | atcgacttcgagcgttctc | o |
| 715 | atgcactctgcagcgttctc | o |
| 716 | agtgactctccagcgttctc | o |
| 717 | gccagatgttagctgga | o |
| 718 | atcgactcgagcgttctc | o |
| 719 | atcgatcgagcgttctc | o |
| 720 | bgagaacgctcgaccttcgat | o |
| 721 | gctagacgttagctgga | sos |
| 722 | atcgactctcgagcgttctc | sos |
| 723 | tagacgttagcgtga | o |
| 724 | cgactctcgagcgttctc | o |
| 725 | ggggtcgaccttggagggggg | sos |
| 726 | gctaacgttagcgtga | o |
| 727 | cgtcgtcgt | o |
| 728 | gagaacgctggacztcccat | o |
| 729 | atcgacctacgtgcgttztc | o |
| 730 | atzgacctacgtgcgttctc | o |
| 731 | gctagazgttagcgt | o |
| 732 | atcgactctcgagzgttctc | o |
| 733 | ggggtaatgcatcagggggg | sos |
| 734 | ggctgtattcctgactgccc | s |
| 735 | ccatgctaacctctagc | o |
| 736 | gctagatgttagcgtga | o |
| 737 | cgtaccttacggtga | o |
| 738 | tccatgctggtcctgatgct | o |
| 739 | atcgactctctcgagcgttctc | o |
| 740 | gctagagcttagcgtga | o |
| 741 | atcgactctcgagtgttctc | o |
| 742 | aacgctcgaccttcgat | o |
| 743 | ctcaacgctggaccttccat | o |
| 744 | atcgacctacgtgcgttctc | o |
| 745 | gagaatgctggaccttccat | o |
| 746 | tcacgctaacctctgac | o |
| 747 | bgagaacgctccagcactgat | o |
| 748 | bgagcaagctggaccttccat | o |
| 749 | cgctagaggttagcgtga | o |
| 750 | gctagatgttaacgt | o |
| 751 | atggaaggtccacgttctc | o |
| 752 | gctagatgttagcgt | o |
| 753 | gctagacgttagtgt | o |
| 754 | tccatgacggtcctgatgct | o |
| 755 | tccatggcggtcctgatgct | o |
| 756 | gctagacgatagcgt | o |
| 757 | gctagtcgatagcgt | o |
| 758 | tccatgacgttcctgatgct | o |

TABLE 1-continued

| SEQ ID NO: | ODN SEQUENCE | BACKBONE |
|---|---|---|
| 759 | tccatgtcgttcctgatgct | o |
| 760 | gctagacgttagzgt | o |
| 761 | gctaggcgttagcgt | o |
| 762 | tccatgtzggtcctgatgct | o |
| 763 | tccatgtcggtzctgatgct | o |
| 764 | atzgactctzgagzgttctc | o |
| 765 | atggaaggtccagtgttctc | o |
| 766 | gcatgacgttgagct | o |
| 767 | ggggtcaacgttgagggggg | s |
| 768 | ggggtcaagtctgagggggg | sos |
| 769 | cgcgcgcgcgcgcgcgcg | o |
| 770 | cccccccccccccccccccccc | s |
| 771 | ccccccccccccccccccccccccccccccc | s |
| 772 | tccatgtcgctcctgatcct | o |
| 773 | gctaaacgttagcgt | o |
| 774 | tccatgtcgatcctgatgct | o |
| 775 | tccatgccggtcctgatgct | o |
| 776 | aaaatcaacgttgaaaaaaa | sos |
| 777 | tccataacgttcctgatgct | o |
| 778 | tggaggtcccaccgagatcggag | o |
| 779 | cgtcgtcgtcgtcgtcgt | s |
| 780 | ctgctgctgctgctgctg | s |
| 781 | gagaacgctccgaccttcgat | s |
| 782 | gctagatgttagcgt | s |
| 783 | gcatgacgttgagct | s |
| 784 | tcaatgctgaf | o |
| 785 | tcaacgttgaf | o |
| 786 | tcaacgttgab | o |
| 787 | gcaatattgcb | o |
| 788 | gcaatattgcf | o |
| 789 | agttgcaact | o |
| 790 | tcttcgaa | o |
| 791 | tcaacgtc | o |
| 792 | ccatgtcggtcctgatgct | o |
| 793 | gttttttatataatttggg | o |
| 794 | ttttttgtttgtcgttttgtcgtt | o |
| 795 | ttggggggggtt | s |
| 796 | ggggttggggtt | s |
| 797 | ggtggtgtaggttttgg | o |
| 798 | bgagaazgctcgaccttcgat | o |
| 799 | tcaacgttaacgttaacgtt | o |
| 800 | bgagcaagztggaccttccat | o |
| 801 | bgagaazgctccagcactgat | o |
| 802 | tcaazgttgax | o |
| 803 | gzaatattgcx | o |
| 804 | tgctgcttttgtcgttttgtgctt | o |
| 805 | ctgcgttagcaatttaactgtg | o |
| 806 | tccatgacgttcctgatgct | s |
| 807 | tgcatgccgtgcatccgtacacagctct | s |
| 808 | tgcatgccgtacacagctct | s |
| 809 | tgcatcagctct | s |
| 810 | tgcgctct | s |
| 811 | ccccccccccccccccccc | s |
| 812 | cccccccccccc | s |
| 813 | cccccccc | s |
| 814 | tgcatcagctct | sos |
| 815 | tgcatgccgtacacagctct | o |
| 816 | gagcaagctggaccttccat | s |
| 817 | tcaacgttaacgttaacgttaacgttaacgtt | s |
| 818 | gagaacgctcgaccttcgat | s |
| 819 | gtccccatttcccagaggaggaaat | o |
| 820 | ctagcggctgacgtcatcaagctag | o |
| 821 | ctagcttgatgacgtcagccgctag | o |
| 822 | cggctgacgtcatcaa | s |
| 823 | ctgacgtg | o |
| 824 | ctgacgtcat | o |
| 825 | attcgatcggggcggggcgag | o |
| 826 | ctcgccccgccccgatcgaat | o |
| 827 | gactgacgtcagcgt | o |
| 828 | ctagcggctgacgtcataaagctagc | s |
| 829 | ctagctttatgacgtcagccgctagc | s |
| 830 | ctagcggctgagctcataaagctagc | s |
| 831 | ctagtggctgacgtcatcaagctag | s |
| 832 | tccaccacgtggtctatgct | s |
| 833 | gggaatgaaagatttttattataag | o |
| 834 | tctaaaaaccatctattcttaaccct | o |
| 835 | agctcaacgtcatgc | o |

TABLE 1-continued

| SEQ ID NO: | ODN SEQUENCE | BACKBONE |
|---|---|---|
| 836 | ttaacggtggtagcggtattggtc | o |
| 837 | ttaagaccaataccgctaccaccg | o |
| 838 | gatctagtgatgagtcagccggatc | o |
| 839 | gatccggctgactcatcactagatc | o |
| 840 | tccaagacgttcctgatgct | o |
| 841 | tccatgacgtccctgatgct | o |
| 842 | tccaccacgtggctgatgct | o |
| 843 | ccacgtggacctctagc | o |
| 844 | tcagaccacgtggtcgggtgttcctga | o |
| 845 | tcaggaacacccgaccacgtggtctga | o |
| 846 | catttccacgatttccca | o |
| 847 | ttcctctctgcaagagact | o |
| 848 | tgtatctctctgaaggact | o |
| 849 | ataaagcgaaactagcagcagtttc | o |
| 850 | gaaactgctgctagtttcgctttat | o |
| 851 | tgcccaaagaggaaaatttgtttcatacag | o |
| 852 | ctgtatgaaacaaattttcctctttgggca | o |
| 853 | ttagggttagggttagggtt | ss |
| 854 | tccatgagcttcctgatgct | ss |
| 855 | aaaacatgacgttcaaaaaa | ss |
| 856 | aaaacatgacgttcgggggg | ss |
| 857 | ggggcatgagcttcgggggg | sos |
| 858 | ctaggctgacgtcatcaagctagt | o |
| 859 | tctgacgtcatctgacgttggctgacgtct | o |
| 860 | ggaattagtaatagatatagaagtt | o |
| 861 | tttacctttataaacataactaaaacaaa | o |
| 862 | gcgttttttttgcg | s |
| 863 | atatctaatcaaaacattaacaaa | o |
| 864 | tctatcccaggtggttcctgttag | o |
| 865 | btccatgacgttcctgatgct | o |
| 866 | btccatgagcttcctgatgct | o |
| 867 | tttttttttttttf | o |
| 868 | tttttttttttttf | so |
| 869 | ctagcttgatgagctcagccgctag | o |
| 870 | ttcagttgtcttgctgcttagctaa | o |
| 871 | tccatgagcttcctgagtct | s |
| 872 | ctagcggctgacgtcatcaatctag | o |
| 873 | tgctagctgtgcctgtacct | s |
| 874 | atgctaaaggacgtcacattgca | o |
| 875 | tgcaatgtgacgtcctttagcat | o |
| 876 | gtagggactttccgagctcgagatcctatg | o |
| 877 | cataggatctcgagctcggaaagtcccctac | o |
| 878 | ctgtcaggaactgcaggtaagg | o |
| 879 | cataacataggaatatttactcctcgc | o |
| 880 | ctccagctccaagaaaggacg | o |
| 881 | gaagtttctggtaagtcttcg | o |
| 882 | tgctgcttttgtgcttttgtgctt | s |
| 883 | tcgtcgttttgtggttttgtggtt | s |
| 884 | tcgtcgttttgtcgttttgtcgtt | s |
| 885 | tcctgacgttcggcgcgcgccc | s |
| 886 | tgctgcttttgtgcttttgtgctt | s |
| 887 | tccatgagcttcctgagctt | s |
| 888 | tcgtcgtttcgtcgttttgacgtt | s |
| 889 | tcgtcgtttgcgtgcgtttcgtcgtt | s |
| 890 | tcgcgtgcgttttgtcgttttgacgtt | s |
| 891 | ttcgtcgttttgtcgttttgtcgtt | s |
| 892 | tcctgacggggaagt | s |
| 893 | tcctggcgtggaagt | s |
| 894 | tcctggcggtgaagt | s |
| 895 | tcctggcgttgaagt | s |
| 896 | tcctgacgtggaagt | s |
| 897 | gcgacgttcggcgcgcgccc | s |
| 898 | gcgacgggcggcgcgcgccc | s |
| 899 | gcggcgtgcggcgcgcgccc | s |
| 900 | gcggcgggtcggcgcgcgccc | s |
| 901 | gcgacggtcggcgcgcgccc | s |
| 902 | gcggcgttcggcgcgcgccc | s |
| 903 | gcgacgtgcggcgcgcgccc | s |
| 904 | tcgtcgctgtctccg | s |
| 905 | tgtggggtttggttttgg | s |
| 906 | agggagggagggagggg | s |
| 907 | tgtgtgtgtgtgtgtgtgt | s |
| 908 | ctctctctctctctctctct | chimeric |
| 909 | ggggtcgacgtcgaggggggg | s |
| 910 | atatatatatatatatatat | s |
| 911 | tttttttttttttttttttttttttt | s |
| 912 | tttttttttttttttttttttt | s |

TABLE 1-continued

| SEQ ID NO: | ODN SEQUENCE | BACKBONE |
|---|---|---|
| 913 | tttttttttttttttttttt | s |
| 914 | gctagagggagggt | |
| 915 | gctagatgttagggg | |
| 916 | gcatgaggggagct | |
| 917 | atggaaggtccagggggctc | |
| 918 | atggactctggagggggctc | |
| 919 | atggaaggtccaaggggctc | |
| 920 | gagaagggggaccttggat | |
| 921 | gagaagggggaccttccat | |
| 922 | gagaaggggccagcactgat | |
| 923 | tccatgtggggcctgatgct | |
| 924 | tccatgaggggcctgatgct | |
| 925 | tccatgtggggcctgctgat | |
| 926 | atggactctccggggttctc | |
| 927 | atggaaggtccggggttctc | |
| 928 | atggactctggaggggtctc | |
| 929 | atggaggctccatggggctc | |
| 930 | atggactctgggggttctc | |
| 931 | tccatgtgggtggggatgct | |
| 932 | tccatgcgggtggggatgct | |
| 933 | tccatggggtcctgatgct | |
| 934 | tccatggggtccctgatgct | |
| 935 | tccatgggggtgcctgatgct | |
| 936 | tccatggggttcctgatgct | |
| 937 | tccatcggggcctgatgct | |
| 938 | gctagagggagtgt | |
| 939 | tttttttttttttttttt | s |
| 940 | gmggtcaacgttgagggmggg | s |
| 941 | ggggagttcgttgagggggg | s |
| 942 | tcgtcgttttcccccccccc | s |
| 943 | ttgggggttttttttttttttttt | s |
| 944 | tttaaatttaaaatttaaaata | s |
| 945 | ttggttttttggttttttttgg | s |
| 946 | tttccctttccccttttccctc | s |
| 947 | ggggtcatcgatgaggggggg s | sos |
| 948 | tccatgacgttcctgacgtt | |
| 949 | tccatgacgttcctgacgtt | |
| 950 | tccatgacgttcctgacgtt | |
| 951 | tccatgacgttcctgacgtt | |
| 952 | tccatgacgttcctgacgtt | |
| 953 | tccatgacgttcctgacgtt | |
| 954 | tccatgacgttcctgacgtt | |
| 955 | tccatgacgttcctgacgtt | |
| 956 | tccatgacgttcctgacgtt | |
| 957 | tccatgacgttcctgacgtt | |
| 958 | tccatgacgttcctgacgtt | |
| 959 | gggggacgatcgtcggggg | sos |
| 960 | gggggtcgtacgacggggg | sos |
| 961 | tttttttttttttttttttttttt | po |
| 962 | aaaaaaaaaaaaaaaaaaaaaaaa | po |
| 963 | cccccccccccccccccccccccc | po |
| 964 | tcgtcgttttgtcgttttgtcgtt | |
| 965 | tcgtcgttttgtcgttttgtcgtt | |
| 966 | tcgtcgttttgtcgttttgtcgtt | |
| 967 | tcgtcgttttgtcgttttgtcgtt | |
| 968 | ggggtcaacgttgagggggg | |
| 969 | ggggtcaacgttgagggggg | |
| 970 | ggggtcaagcttgagggggg | |
| 971 | tgctgcttcccccccccccc | |
| 972 | ggggacgtcgacgtgggggg | sos |
| 973 | ggggtcgtcgacgagggggg | sos |
| 974 | ggggtcgacgtacgtcgaggggggg | sos |
| 975 | ggggaccggtaccggtgggggg | sos |
| 976 | gggtcgacgtcgagggggg | sos |
| 977 | ggggtcgacgtcgagggggg | sos |
| 978 | ggggaacgttaacgttgggggg | sos |
| 979 | ggggtcaccggtgagggggg | sos |
| 980 | ggggtcgttcgaacgagggggg | sos |
| 981 | ggggacgttcgaacgtgggggg | sos |
| 982 | tcaactttga | s |
| 983 | tcaagcttga | s |
| 984 | tcacgatcgtga | s |
| 985 | tcagcatgctga | s |
| 986 | gggggagcatgctgggggg | sos |
| 987 | ggggggggggggggggggg | sos |
| 988 | gggggacgatatcgtcggggg | sos |
| 989 | gggggacgacgtcgtcggggg | sos |

TABLE 1-continued

| SEQ ID NO: | ODN SEQUENCE | BACKBONE |
|---|---|---|
| 990 | gggggacgagctcgtcggggggg | sos |
| 991 | gggggacgtacgtcggggggg | sos |
| 992 | tcaacgtt | |
| 993 | tccataccggtcctgatgct | |
| 994 | tccataccggtcctaccggt | s |
| 995 | gggggacgatcgttggggggg | sos |
| 996 | ggggaacgatcgtcggggggg | sos |
| 997 | ggg ggg acg atc gtc ggg ggg | sos |
| 998 | ggg gga cga tcg tcg ggg ggg | sos |
| 999 | aaa gac gtt aaa | po |
| 1000 | aaagagcttaaa | po |
| 1001 | aaagazgttaaa | po |
| 1002 | aaattcggaaaa | po |
| 1003 | gggggtcatcgatgaggggggg | sos |
| 1004 | gggggtcaacgttgagggggg | sos |
| 1005 | atgtagcttaataacaaagc | po |
| 1006 | ggatcccttgagttacttct | po |
| 1007 | ccattccacttctgattacc | po |
| 1008 | tatgtattatcatgtagata | po |
| 1009 | agcctacgtattcaccctcc | po |
| 1010 | ttcctgcaactactattgta | po |
| 1011 | atagaaggccctacaccagt | po |
| 1012 | ttacaccggtctatggaggt | po |
| 1013 | ctaaccagatcaagtctagg | po |
| 1014 | cctagacttgatctggttag | po |
| 1015 | tataagcctcgtccgacatg | po |
| 1016 | catgtcggacgaggcttata | po |
| 1017 | tggtggtggggagtaagctc | po |
| 1018 | gagctactcccccaccacca | po |
| 1019 | gccttcgatcttcgttggga | po |
| 1020 | tggacttctcttttgccgtct | po |
| 1021 | atgctgtagcccagcgataa | po |
| 1022 | accgaatcagcggaaagtga | po |
| 1023 | tccatgacgttcctgacgtt | |
| 1024 | ggagaaacccatgagctcatctgg | |
| 1025 | accacagaccagcaggcaga | |
| 1026 | gagcgtgaactgcgcgaaga | |
| 1027 | tcggtaccttgcagcggtt | |
| 1028 | ctggagccctagccaaggat | |
| 1029 | gcgactccatcaccagcgat | |
| 1030 | cctgaagtaagaaccagatgt | |
| 1031 | ctgtgttatctgacatacacc | |
| 1032 | aattagccttaggtgattggg | |
| 1033 | acatctggttcttacttcagg | |
| 1034 | ataagtcatattttgggaactac | |
| 1035 | cccaatcacctaaggctaatt | |
| 1036 | ggggtcgtcgacgaggggggg | sos |
| 1037 | ggggtcgttcgaacgagggggg | sos |
| 1038 | ggggacgttcgaacgtggggggg | sos |
| 1039 | tcctggcgggaagt | s |
| 1040 | ggggaacgacgtcgttggggggg | sos |
| 1041 | ggggaacgtacgtcgggggg | sos |
| 1042 | ggggaacgtacgtacgttgggggg | sos |
| 1043 | ggggtcaccggtgaggggggg | sos |
| 1044 | ggggtcgacgtacgtcgagggggg | sos |
| 1045 | ggggaccggtaccggtggggggg | sos |
| 1046 | gggtcgacgtcgaggggggg | sos |
| 1047 | ggggtcgacgtcgagggg | sos |
| 1048 | ggggaacgttaacgttggggggg | sos |
| 1049 | ggggacgtcgacgtgggggg | sos |
| 1050 | gcactcttcgaagctacagccggcagcctctgat | |
| 1051 | cggctcttccatgaggtctttgctaatcttgg | |
| 1052 | cggctcttccatgaaagtctttggacgatgtgagc | |
| 1053 | tcctgcaggttaagt | s |
| 1054 | gggggtcgttcgttgggggg | sos |
| 1055 | gggggatgattgttggggggg | sos |
| 1056 | gggggazgatzgttggggggg | sos |
| 1057 | gggggagctagcttgggggg | sos |
| 1058 | ggttcttttggtccttgtct | s |
| 1059 | ggttcttttggtcctcgtct | s |
| 1060 | ggttcttttggtccttatct | s |
| 1061 | ggttcttggtttccttgtct | s |
| 1062 | tggtcttttggtccttgtct | s |
| 1063 | ggttcaaatggtccttgtct | s |
| 1064 | gggtcttttgggccttgtct | s |
| 1065 | tccaggacttctctcaggttttt | s |
| 1066 | tccaaaacttctctcaaatt | s |

TABLE 1-continued

| SEQ ID NO: | ODN SEQUENCE | BACKBONE |
|---|---|---|
| 1067 | tactacttttatacttttatactt | s |
| 1068 | tgtgtgtgtgtgtgtgtgtgtg | s |
| 1069 | ttgttgttgttgtttgttgttgttg | s |
| 1070 | ggctccggggagggaatttttgtctat | s |
| 1071 | gggacgatcgtcgggggggg | sos |
| 1072 | gggtcgtcgacgaggggggg | sos |
| 1073 | ggtcgtcgacgagggggggg | sos |
| 1074 | gggtcgtcgtcgtgggggggg | sos |
| 1075 | ggggacgatcgtcggggggg | sos |
| 1076 | ggggacgtcgtcgtggggggg | sos |
| 1077 | ggggtcgacgtcgacgtcgaggggggg | sos |
| 1078 | ggggaaccgcggttggggggg | sos |
| 1079 | ggggacgacgtcgtgggggggg | sos |
| 1080 | tcgtcgtcgtcgtcgtgggggggg | sos |
| 1081 | tcctgccggggaagt | s |
| 1082 | tcctgcaggggaagt | s |
| 1083 | tcctgaaggggaagt | s |
| 1084 | tcctggcgggcaagt | s |
| 1085 | tcctggcgggtaagt | s |
| 1086 | tcctggcgggaaagt | s |
| 1087 | tccgggcggggaagt | s |
| 1088 | tcggggcggggaagt | s |
| 1089 | tcccggcggggaagt | s |
| 1090 | gggggacgttggggg | s |
| 1091 | ggggtttttttttggggggg | sos |
| 1092 | ggggccccccccccggggggg | sos |
| 1093 | ggggttgttgttgttggggggg | sos |

In some embodiments, the immunostimulatory nucleic acid is a CpG nucleic acid. CpG sequences, while relatively rare in human DNA are commonly found in the DNA of infectious organisms such as bacteria. The human immune system has apparently evolved to recognize CpG sequences as an early warning sign of infection and to initiate an immediate and powerful immune response against invading pathogens without causing adverse reactions frequently seen with other immune stimulatory agents. Thus CpG containing nucleic acids, relying on this innate immune defense mechanism can utilize a unique and natural pathway for immune therapy. The effects of CpG nucleic acids on immune modulation have been described extensively in published patent applications, such as PCT US95/01570), PCT/US97/19791, PCT/US98/03678; PCT/US98/10408; PCT/US98/04703; PCT/US99/07335; and PCT/US99/09863. The entire contents of each of these patent applications is hereby incorporated by reference.

A CpG nucleic acid is a nucleic acid which includes at least one unmethylated CpG dinucleotide. A nucleic acid containing at least one unmethylated CpG dinucleotide is a nucleic acid molecule which contains an unmethylated cytosine in a cytosine-guanine dinucleotide sequence (i.e. "CpG DNA" or DNA containing a 5' cytosine followed by 3' guanosine and linked by a phosphate bond) and activates the immune system. The CpG nucleic acids can be double-stranded or single-stranded. Generally, double-stranded molecules are more stable in vivo, while single-stranded molecules have increased immune activity. Thus in some aspects of the invention it is preferred that the nucleic acid be single stranded and in other aspects it is preferred that the nucleic acid be double stranded. The terms CpG nucleic acid or CpG oligonucleotide as used herein refer to an immunostimulatory CpG nucleic acid or a nucleic acid unless otherwise indicated. The entire immunostimulatory nucleic acid can be unmethylated or portions may be unmethylated but at least the C of the 5' CG 3' must be unmethylated.

In one preferred embodiment the invention provides an immunostimulatory nucleic acid which is a CpG nucleic acid represented by at least the formula:

5'$X_1X_2CGX_3X_4$3' wherein $X_1$, $X_2$, $X_3$, and X4 are nucleotides. In one embodiment $X_2$ is adenine, guanine, cytosine, or thymine. In another embodiment $X_3$ is cytosine, guanine, adenine, or thymine. In other embodiments $X_2$ is adenine, guanine, or thymine and $X_3$ is cytosine, adenine, or thymine.

In another embodiment the immunostimulatory nucleic acid is an isolated CpG nucleic acid represented by at least the formula:

5'$N_1X_1X_2CGX_3X_4N_2$3' wherein $X_1$, $X_2$, $X_3$, and $X_4$ are nucleotides and N is any nucleotide and $N_1$ and $N_2$ are nucleic acid sequences composed of from about 0-25 N's each. In one embodiment $X_1X_2$ are nucleotides selected from the group consisting of: GpT, GpG, GpA, ApA, ApT, ApG, CpT, CpA, CpG, TpA, TpT, and TpG; and $X_3X_4$ are nucleotides selected from the group consisting of: TpT, ApT, TpG, ApG, CpG, TpC, ApC, CpC, TpA, ApA, and CpA. Preferably $X_1X_2$ are GpA or GpT and $X_3X_4$ are TpT. In other embodiments $X_1$ or $X_2$ or both are purines and $X_3$ or $X_4$ or both are pyrimidines or $X_1X_2$ are GpA and $X_3$ or $X_4$ or both are pyrimidines. In another preferred embodiment $X_1X_2$ are nucleotides selected from the group consisting of: TpA, ApA, ApC, ApG, and GpG. In yet another embodiment $X_3X_4$ are nucleotides selected from the group consisting of: TpT, TpA, TpG, ApA, ApG, ApC, and CpA. $X_1X_2$ in another embodiment are nucleotides selected from the group consisting of: TpT, TpG, ApT, GpC, CpC, CpT, TpC, GpT and CpG.

In another preferred embodiment the immunostimulatory nucleic acid has the sequence 5'TCN$_1$TX$_1$X$_2$CGX$_3$X$_4$3'. The immunostimulatory nucleic acids of the invention in some embodiments include $X_1X_2$ selected from the group consisting of GpT, GpG, GpA and ApA and $X_3X_4$ is selected from the group consisting of TpT, CpT and TpC.

In other embodiments, the CpG oligonucleotide has a sequence selected from the group consisting of SEQ ID NO: 1, 3, 4, 14-16, 18-24, 28, 29, 33-46, 49, 50, 52-56, 58, 64-67, 69, 71, 72, 76-87, 90, 91, 93, 94, 96, 98, 102-124, 126-128, 131-133, 136-141, 146-150, 152-153, 155-171, 173-178, 180-186, 188-198, 201, 203-214, 216-220, 223, 224, 227-240, 242-256, 258, 260-265, 270-273, 275, 277-281, 286-287, 292, 295-296, 300, 302, 305-307, 309-312, 314-317, 320-327, 329, 335, 337-341, 343-352, 354, 357, 361-365, 367-369, 373-376, 378-385, 388-392, 394, 395, 399, 401-404, 406-426, 429-433, 434-437, 439, 441-443, 445, 447, 448, 450, 453-456, 460-464, 466-469, 472-475, 477, 478, 480, 483-485, 488, 489, 492, 493, 495-502, 504-505, 507-509, 511, 513-529, 532-541, 543-555, 564-566, 568-576, 578, 580, 599, 601-605, 607-611, 613-615, 617, 619-622, 625-646, 648-650, 653-664, 666-697, 699-706, 708, 709, 711-716, 718-732, 736, 737, 739-744, 746, 747, 749-761, 763, 766-767, 769, 772-779, 781-783, 785-786, 7900792, 798-799, 804-808, 810, 815, 817, 818, 820-832, 835-846, 849-850, 855-859, 862, 865, 872, 874-877, 879-881, 883-885, 888-904, and 909-913.

For facilitating uptake into cells, the immunostimulatory nucleic acids are preferably in the range of 6 to 100 bases in length. However, nucleic acids of any size greater than 6 nucleotides (even many kb long) are capable of inducing an immune response according to the invention if sufficient immunostimulatory motifs are present. Preferably the immunostimulatory nucleic acid is in the range of between 8 and 100 and in some embodiments between 8 and 50 or 8 and 30 nucleotides in size.

"Palindromic sequence" shall mean an inverted repeat (i.e. a sequence such as ABCDEE'D'C'B'A' in which A and A' are bases capable of forming the usual Watson-Crick base pairs. In vivo, such sequences may form double-stranded structures. In one embodiment the CpG nucleic acid contains a palindromic sequence. A palindromic sequence used in this context refers to a palindrome in which the CpG is part of the palindrome, and preferably is the center of the palindrome. In another embodiment the CpG nucleic acid is free of a palindrome. An immunostimulatory nucleic acid that is free of a palindrome is one in which the CpG dinucleotide is not part of a palindrome. Such an oligonucleotide may include a palindrome in which the CpG is not the center of the palindrome.

The CpG nucleic acid sequences of the invention are those broadly described above as well as disclosed in PCT Published Patent Applications PCT/US95/01570 and PCT/US97/19791 claiming priority to U.S. Ser. Nos. 08/386,063 and 08/960,774, filed on Feb. 7, 1995 and Oct. 30, 1997 respectively.

The immunostimulatory nucleic acids of the invention also include nucleic acids having T-rich motifs. It was recently discovered by Dr. Arthur Krieg that T-rich nucleic acids were immunostimulatory. It was presented by Dr. Krieg at the International Workshop on "Immunobiology of Bacterial CpG-DNA" held in Upper Bavaria on Sep. 26-29, 1999 that poly-T nucleic acids of 24 bases in length are immunostimulatory, whereas the same length poly-C oligonucleotide is non-stimulatory. These concepts are also described and claimed in U.S. Provisional Patent Application No. 60/156, 113 filed on Sep. 25, 1999, which is hereby incorporated by reference.

Poly-G containing nucleic acids are also immunostimulatory. PCT published patent application number WO 00/14217, which claims priority to German Patent Application No. 98 11 6652.3, filed on Sep. 3, 1998 describes poly-G-containing oligonucleotides and their uses. A variety of other references, including Pisetsky and Reich, 1993 *Mol. Biol. Reports*, 18:217-221; Krieger and Herz, 1994, *Ann. Rev. Biochem.*, 63:601-637; Macaya et al., 1993, *PNAS*, 90:3745-3749; Wyatt et al., 1994, *PNAS*, 91:1356-1360; Rando and Hogan, 1998, In Applied Antisense Oligonucleotide Technology, ed. Krieg and Stein, p. 335-352; and Kimura et al., 1994, *J. Biochem.* 116, 991-994 also describe the immunostimulatory properties of poly-G nucleic acids. Poly-G-containing nucleotides are useful for treating and preventing bacterial and viral infections.

In some aspects of the invention the poly-G containing nucleic acids are administered alone for the treatment of asthma and allergy. It was previously suggested in the prior art that poly-G rich oligonucleotides inhibit the production of IFN-δ by compounds such as CpG oligonucleotides, concanavalin A, bacterial DNA, or the combination of PMA and the calcium ionophore A 23187 (Halperin and Pisetsky, 1995, *Immunopharmacol.*, 29:47-52, as well as block the downstream effects of IFN-δ. For instance, Ramanathan et al., 1994, *Transplantation*, 57:612-615, has shown that a poly-G oligonucleotide inhibits the binding of IFN-δ to its receptor, which prevents the normal enhancement of MHC Class 1 and ICAM-1 in response to IFN-δ. Poly-G oligonucleotides were also found to be able to inhibit the secretion of IFN-δ from lymphocytes (Halperin and Pisetsky, 1995, *Immunopharmacol.*, 29:47-52). It was surprisingly, discovered according to the invention that when poly-G nucleic acids are administered in vivo, they are useful for treating or preventing allergy or asthma. Thus, in this aspect of the invention, poly-G nucleic acids are administered alone or optionally with other asthma/allergy medicaments for the treatment of allergy and/or asthma.

Poly-G nucleic acids preferably are nucleic acids having the following formulas:

$$5'X_1X_2GGGX_3X_4 3'$$

wherein $X_1$, $X_2$, $X_3$, and $X_4$ are nucleotides. In preferred embodiments at least one of $X_3$ and $X_4$ are a G. In other embodiments both of $X_3$ and $X_4$ are a G. In yet other embodiments the preferred formula is 5' GGGNGGG 3', or 5' GGGNGGGNGG 3' wherein N represents between 0 and 20 nucleotides. In other embodiments the poly-G nucleic acid is free of unmethylated CG dinucleotides, while in other embodiments the poly-G nucleic acid includes at least one unmethylated CG dinucleotide.

The poly G nucleic acid in some embodiments is selected from the group consisting of SEQ ID NO: 5, 6, 73, 215, 267-269, 276, 282, 288, 297-299, 355, 359, 386, 387, 444, 476, 531, 557-559, 733, 768, 795, 796, 914-925, 928-931, 933-936, and 938. In other embodiments, the poly G nucleic acid includes a sequence selected from the group consisting of SEQ ID NO: 67, 80-82, 141, 147, 148, 173, 178, 183, 185, 214, 224, 264, 265, 315, 329, 434, 435, 475, 519, 521-524, 526, 527, 535, 554, 565, 609, 628, 660, 661, 662, 725, 767, 825, 856, 857, 876, 892, 909, 926, 927, 932, and 937. In some embodiments, the entire backbone of the poly-G nucleic acid is phosphorothioate.

In related embodiments, the invention also contemplates the use of immunostimulatory nucleic acids that comprise one and preferably two poly-G motifs, even more preferably flanking a palindrome. Such immunostimulatory nucleic acids preferably have a chimeric backbone (i.e., their backbone is comprised of both phosphodiester and phosphorothioate linkages). Even more preferably, the phosphorothioate linkages in these latter immunostimulatory nucleic acids are located at the 5' and 3' ends of the nucleic acid. Examples of suitable palindromes include, but are not limited to AACGTT; AAGCTT; AGCGCT; TCGA; TTCGAA; ACGT; GACGTC; and CACGTG.

Nucleic acids having modified backbones, such as phosphorothioate backbones, fall within the class of immunostimulatory nucleic acids. U.S. Pat. Nos. 5,723,335 and 5,663,153 issued to Hutcherson, et al. and related PCT publication WO95/26204 describe immune stimulation using phosphorothioate oligonucleotide analogues. These patents describe the ability of the phosphorothioate backbone to stimulate an immune response in a non-sequence specific manner.

The backbone characteristics of the nucleic acids listed in Table 1 are also shown. Some of the designations in the Table are as follows: o or po=phosphodiester, s=phosphorothioate, sos=chimeric.

In the case when the immunostimulatory nucleic acid is administered in conjunction with a nucleic acid vector, it is preferred that the backbone of the immunostimulatory nucleic acid be a chimeric combination of phosphodiester and phosphorothioate (or other phosphate modification). The cell may have a problem taking up a plasmid vector in the presence of completely phosphorothioate oligonucleotide. Thus when both a vector and an oligonucleotide are delivered to a subject, it is preferred that the oligonucleotide have a chimeric backbone or have a phosphorothioate backbone but that the plasmid is associated with a vehicle that delivers it directly into the cell, thus avoiding the need for cellular uptake. Such vehicles are known in the art and include, for example, liposomes and gene guns.

For use in the instant invention, the immunostimulatory nucleic acids can be synthesized de novo using any of a number of procedures well known in the art. Such compounds are referred to as "synthetic nucleic acids." For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid. Res.* 14:5399-5407, 1986,; Garegg et al., *Tet. Let.* 27:4055-4058, 1986, Gaffney et al., *Tet. Let.* 29:2619-2622, 1988). These chemistries can be performed by a variety of automated oligonucleotide synthesizers available in the market. These nucleic acids are referred to as synthetic nucleic acids. Alternatively, immunostimulatory nucleic acids can be produced on a large scale in plasmids, (see Sambrook, T., et al., "Molecular Cloning: A Laboratory Manual", Cold Spring Harbor laboratory Press, New York, 1989) and separated into smaller pieces or administered whole. Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acids. The term "immunostimulatory nucleic acid" encompasses both synthetic and isolated immunostimulatory nucleic acids.

For use in vivo, nucleic acids are preferably relatively resistant to degradation (e.g., are stabilized). A "stabilized nucleic acid molecule" shall mean a nucleic acid molecule that is relatively resistant to in vivo degradation (e.g. via an exo- or endo-nuclease). Stabilization can be a function of length or secondary structure. Immunostimulatory nucleic acids that are tens to hundreds of kbs long are relatively resistant to in vivo degradation. For shorter immunostimulatory nucleic acids, secondary structure can stabilize and increase their effect. For example, if the 3' end of a nucleic acid has self-complementarity to an upstream region, so that it can fold back and form a sort of stem loop structure, then the o nucleic acid becomes stabilized and therefore exhibits more activity.

Alternatively, nucleic acid stabilization can be accomplished via backbone modifications. Preferred stabilized nucleic acids of the instant invention have a modified backbone. It has been demonstrated that modification of the nucleic acid backbone provides enhanced activity of the immunostimulatory nucleic acids when administered in vivo. One type of modified backbone is a phosphate backbone modification. Immunostimulatory nucleic acids, including at least two phosphorothioate linkages at the 5' end of the oligonucleotide and multiple phosphorothioate linkages at the 3' end, preferably 5, can in some circumstances provide maximal activity and protect the nucleic acid from degradation by intracellular exo- and endo-nucleases. Other phosphate modified nucleic acids include phosphodiester modified nucleic acids, combinations of phosphodiester and phosphorothioate nucleic acids, methylphosphonate, methylphosphorothioate, phosphorodithioate, and combinations thereof. Each of these combinations in CpG nucleic acids and their particular effects on immune cells is discussed in more detail in PCT Published Patent Applications PCT/US95/01570 and PCT/US97/19791, the entire contents of which are hereby incorporated by reference. Although Applicants are not bound by the theory, it is believed that these phosphate modified nucleic acids may show more stimulatory activity due to enhanced nuclease resistance, increased cellular uptake, increased protein binding, and/or altered intracellular localization.

Modified backbones such as phosphorothioates may be synthesized using automated techniques employing either phosphoramidate or H-phosphonate chemistries. Aryl-and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., *Chem. Rev.* 90:544, 1990; Goodchild, J., *Bioconjugate Chem.* 1:165, 1990).

Both phosphorothioate and phosphodiester nucleic acids containing immunostimulatory motifs are active in immune cells. However, based on the concentration needed to induce immunostimulatory nucleic acid specific effects, the nuclease resistant phosphorothioate backbone immunostimulatory nucleic acids are more potent (2 μg/ml for the phosphorothioate vs. a total of 90 μg/ml for phosphodiester).

Another type of modified backbone, useful according to the invention, is a peptide nucleic acid. The backbone is composed of aminoethylglycine and supports bases which provide the DNA-character. The backbone does not include any phosphate and thus may optionally have no net charge. The lack of charge allows for stronger DNA-DNA binding because the charge repulsion between the two strands does not exist. Additionally, because the backbone has an extra methylene group, the oligonucleotides are enzyme/protease resistant. Peptide nucleic acids can be purchased from various commercial sources, e.g., Perkin Elmer, C. A. or synthesized de novo.

Another class of backbone modifications include 2'-O-methylribonucleosides (2'-Ome). These types of substitutions are described extensively in the prior art and in particular with respect to their immunostimulating properties in Zhao et al., *Bioorganic and Medicinal Chemistry Letters*, 1999, 9:24:3453. Zhao et al. describes methods of preparing 2'-Ome modifications to nucleic acids.

The nucleic acid molecules of the invention may include naturally-occurring or synthetic purine or pyrimidine heterocyclic bases as well as modified backbones. Purine or pyrimidine heterocyclic bases include, but are not limited to, adenine, guanine, cytosine, thymidine, uracil, and inosine. Other representative heterocyclic bases are disclosed in U.S. Pat. No. 3,687,808, issued to Merigan, et al. The term purine or pyrimidine or bases are used herein to refer to both naturally-occurring or synthetic purines, pyrimidines or bases.

Other stabilized nucleic acids include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The immunostimulatory nucleic acids having backbone modifications useful according to the invention in some embodiments are S- or R-chiral immunostimulatory nucleic acids. An "S chiral immunostimulatory nucleic acid" as used herein is an immunostimulatory nucleic acid wherein at least two nucleotides have a backbone modification forming a chiral center and wherein a plurality of the chiral centers have S chirality. An "R chiral immunostimulatory nucleic acid" as used herein is an immunostimulatory nucleic acid wherein at least two nucleotides have a backbone modification forming a chiral center and wherein a plurality of the chiral centers have R chirality. The backbone modification may be any type of modification that forms a chiral center. The modifications include but are not limited to phosphorothioate, methylphosphonate, methylphosphorothioate, phosphorodithioate, 2'-Ome and combinations thereof.

The chiral immunostimulatory nucleic acids must have at least two nucleotides within the nucleic acid that have a backbone modification. All or less than all of the nucleotides in the nucleic acid, however, may have a modified backbone. Of the nucleotides having a modified backbone (referred to as chiral centers), a plurality have a single chirality, S or R. A Jo "plurality" as used herein within the context of modified backbones refers to an amount greater than 50%. Thus, less than all of the chiral centers may have S or R chirality as long as a plurality of the chiral centers have S or R chirality. In some embodiments at least 55%, 60%, 65%, 70%, 75%, 80,%, 85%, 90%, 95%, or 100% of the chiral centers have S or R chirality. In other embodiments at least 55%, 60%, 65%, 70%, 75%, 80%, 85%, 90%, 95%, or 100% of the nucleotides have backbone modifications.

The S- and R-chiral immunostimulatory nucleic acids may be prepared by any method known in the art for producing chirally pure oligonucleotides. The Stec et al reference teaches methods for producing stereopure phosphorothioate oligodeoxynucleotides using an oxathiaphospholane. (Stec, W. J., et al., 1995, *J. Am. Chem. Soc.*, 117:12019). Other methods for making chirally pure oligonucleotides have been described by companies such as ISIS Pharmaceuticals. US Patents have also described these methods. For instance U.S. Pat. Nos. 5,883,237; 5,837,856; 5,599,797; 5,512,668; 5,856, 465; 5,359,052; 5,506,212; 5,521,302; and 5,212,295, each of which is hereby incorporated by reference in its entirety, disclose methods for generating stereopure oligonucleotides.

The immunostimulatory nucleic acids are useful for treating or preventing allergy or asthma in a subject. A "subject" shall mean a human or vertebrate mammal including but not limited to a dog, cat, horse, cow, pig, sheep, goat, or primate, e.g., monkey.

The immunostimulatory nucleic acids are useful in some aspects of the invention as a prophylactic for the treatment of a subject at risk of developing an allergy or asthma where the exposure of the subject to an allergen or predisposition to asthma is known or suspected. A "subject at risk" of developing allergy or asthma as used herein is a subject who has any risk of exposure to an allergen or a risk of developing asthma, i.e. someone who has suffered from an asthmatic attack previously or has a predisposition to asthmatic attacks. For instance, a subject at risk may be a subject who is planning to travel to an area where a particular type of allergen or asthmatic initiator is found or it may even be any subject living in an area where an allergen has been identified. If the subject develops allergic responses to a particular antigen and the subject may be exposed to the antigen, i.e., during pollen season, then that subject is at risk of exposure to the antigen. A subject at risk of developing an allergy or asthma includes those subjects that have been identified as having an allergy or asthma but that don't have the active disease during the treatment of the invention as well as subjects that are considered to be at risk of developing these diseases because of genetic or environmental factors.

In addition to the use of the immunostimulatory nucleic acid and the asthma/allergy medicament for prophylactic treatment, the invention also encompasses the use of the combination of drugs for the treatment of a subject having an allergy or asthma. A "subject having an allergy" is a subject that has an allergic reaction in response to an allergen. An "allergy" refers to acquired hypersensitivity to a substance (allergen).

The allergic reaction in man and animals has been extensively studied and the basic immune mechanisms involved are well known. Allergic conditions or diseases in humans include but are not limited to eczema, allergic rhinitis or coryza, hay fever, conjunctivitis, bronchial or allergic asthma, urticaria (hives) and food allergies; atopic dermatitis; anaphylaxis; drug allergy; angioedema; and allergic conjunctivitis. Allergic diseases in dogs include but are not limited to seasonal dermatitis; perennial dermatitis; rhinitis: conjunctivitis; allergic asthma; and drug reactions. Allergic diseases in cats include but are not limited to dermatitis and respiratory disorders; and food allergens. Allergic diseases in horses include but are not limited to respiratory disorders such as "heaves" and dermatitis. Allergic diseases in non-human primates include but are not limited to allergic asthma and allergic dermatitis.

The generic name for molecules that cause an allergic reaction is allergen. There are numerous species of allergens. The allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

The symptoms of the allergic reaction vary, depending on the location within the body where the IgE reacts with the antigen. If the reaction occurs along the respiratory epithelium the symptoms are sneezing, coughing and asthmatic reactions. If the interaction occurs in the digestive tract, as in the case of food allergies, abdominal pain and diarrhea are common. Systematic reactions, for example following a bee sting, can be severe and often life threatening.

Delayed type hypersensitivity, also known as type IV allergy reaction is an allergic reaction characterized by a delay period of at least 12 hours from invasion of the antigen into the allergic subject until appearance of the inflammatory or immune reaction. The T lymphocytes (sensitized T lymphocytes) of individuals in an allergic condition react with the antigen, triggering the T lymphocytes to release lymphokines (macrophage migration inhibitory factor (MIF), macrophage activating factor (MAF), mitogenic factor (MF), skin-reactive factor (SRF), chemotactic factor, neovascularization-accelerating factor, etc.), which function as inflammation mediators, and the biological activity of these lymphokines, together with the direct and indirect effects of locally appearing lymphocytes and other inflammatory immune cells, give rise to the type IV allergy reaction. Delayed allergy reactions include tuberculin type reaction, homograft rejection reaction, cell-dependent type protective reaction, contact dermatitis hypersensitivity reaction, and the like, which are known to be most strongly suppressed by steroidal agents. Consequently, steroidal agents are effective against diseases which are caused by delayed allergy reactions. Long-term use of steroidal agents at concentrations currently being used can, however, lead to the serious side-effect known as steroid dependence. The methods of the invention solve some of these problems, by providing for lower and fewer doses to be administered.

Immediate hypersensitivity (or anaphylactic response) is a form of allergic reaction which develops very quickly, i.e. within seconds or minutes of exposure of the patient to the causative allergen, and it is mediated by IgE antibodies made by B lymphocytes. In nonallergic patients, there is no IgE antibody of clinical relevance; but, in a person suffering with allergic diseases, IgE antibody mediates immediate hypersensitivity by sensitizing mast cells which are abundant in the skin, lymphoid organs, in the membranes of the eye, nose and mouth, and in the respiratory tract and intestines.

Mast cells have surface receptors for IgE, and the IgE antibodies in allergy-suffering patients become bound to them. As discussed briefly above, when the bound IgE is subsequently contacted by the appropriate allergen, the mast cell is caused to degranulate and to release various substances called bioactive mediators, such as histamine, into the surrounding tissue. It is the biologic activity of these substances which is responsible for the clinical symptoms typical of immediate hypersensitivity; namely, contraction of smooth muscle in the airways or the intestine, the dilation of small blood vessels and the increase in their permeability to water and plasma proteins, the secretion of thick sticky mucus, and in the skin, redness, swelling and the stimulation of nerve endings that results in itching or pain.

Many allergies are caused by IgE antibody generation against harmless allergens. The cytokines that are induced by administration of immunostimulatory nucleic acids are predominantly of a class called "Th1" (examples are IL-12 and IFN-γ). Cytokine production by helper $CD4^+$ (and also in $CD8^+$) T cells frequently fall into one of two phenotypes, Th1 and Th2, in both murine and human systems (Romagnani, 1991, Immunol Today 12: 256-257, Mosmann, 1989, Annu Rev Immunol, 7: 145-173). Th1 cells produce interleukin 2 (IL-2), tumor necrosis factor (TNFα) and interferon gamma (IFNγ) and they are responsible primarily for cell-mediated immunity such as delayed type hypersensitivity. Th2 cells produce interleukins, IL-4, IL-5, IL-6, IL-9, IL-10 and IL-13 and are primarily involved in providing optimal help for humoral immune responses such as IgE and IgG4 antibody isotype switching (Mosmann, 1989, Annu Rev Immunol, 7:145-173).

The types of antibodies associated with a Th1 response are generally more protective because they have high neutralization and opsonization capabilities. Th2 responses involve predominately antibodies and these have less protective effect against infection and some Th2 isotypes (e.g., IgE) are associated with allergy. Strongly polarized Th1 and Th2 responses not only play different roles in protection, they can promote different immunopathological reactions. Th1-type responses are involved organ specific autoimmunity such as experimental autoimmune uveoretinitis (Dubey et al, 1991, Eur Cytokine Network 2: 147-152), experimental autoimmune encephalitis (EAE) (Beraud et al, 1991, Cell Immunol 133: 379-389) and insulin dependent diabetes mellitus (Hahn et al, 1987, *Eur. J. Immunol.* 18: 2037-2042), in contact dermatitis (Kapsenberg et al, Immunol Today 12: 392-395), and in some chronic inflammatory disorders. In contrast Th2-type responses are responsible for triggering allergic atopic disorders (against common environmental allergens) such as allergic asthma (Walker et al, 1992, Am Rev Resp Dis 148: 109-115) and atopic dermatitis (van der Heijden et al, 1991, J Invest Derm 97: 389-394), are thought to exacerbate infection with tissue-dwelling protozoa such as helminths (Finkelman et al, 1991, Immunoparasitol Today 12: A62-66) and Leishmania major (Caceres-Dittmar et al, 1993, Clin Exp Immunol 91: 500-505), are preferentially induced in certain primary immunodeficiencies such as hyper-IgE syndrome (Del Prete et al, 1989, J Clin Invest 84: 1830-1835) and Omenn's syndrome (Schandene et al, 1993, Eur J Immunol 23: 56-60), and are associated with reduced ability to suppress HIV replication (Barker et al, 1995, Proc Soc Nat Acad Sci USA 92: 11135-11139).

Thus, in general, it appears that allergic diseases are mediated by Th2 type immune responses. Based on the ability of the immunostimulatory nucleic acid to shift the immune response in a subject from a Th2 (which is associated with production of IgE antibodies and allergy and asthma) to a Th1 response (which is protective against allergic and asthmatic reactions), an effective dose for inducing an immune response of a immunostimulatory nucleic acid can be administered to a subject to treat or prevent an allergy or asthma.

Th2 cytokines, especially IL-4 and IL-5 are elevated in the airways of asthmatic subjects. These cytokines promote important aspects of the asthmatic inflammatory response, including IgE isotype switching, eosinophil chemotaxis and activation, and mast cell growth. Th1 cytokines, especially IFN-g and IL-12, can suppress the formation of Th2 clones and production of Th2 cytokines. Thus, the immunostimulatory nucleic acid has significant therapeutic utility in the treatment of allergic conditions and asthma.

An "allergen" as used herein is a molecule capable of provoking an immune response characterized by production of IgE. Thus, in the context of this invention, the term allergen means a specific type of antigen which can trigger an allergic response which is mediated by IgE antibody. The method and preparations of this invention extend to a broad class of such allergens and fragments of allergens or haptens acting as allergens. Allergens include but are not limited to Environmental Aeroallergens; plant pollens such as Ragweed/hayfever (affects 10% of pop., 25 million ppl); Weed pollen allergens; Grass pollen allergens (grasses affect 10% of pop., 25 million ppl); Johnson grass; Tree pollen allergens; Ryegrass; House dust mite allergens (affects 6% of pop., 15 million ppl); Storage mite allergens; Japanese cedar pollen/hay fever (affects 10% of pop. In Japan, 13 million ppl); Mold spore allergens; Animal allergens (cat (affects 2% of pop., 5 million ppl), dog, guinea pig, hamster, gerbil, rat, mouse); Food Allergens (e.g., Crustaceans; nuts, such as peanuts; citrus fruits); Insect Allergens (Other than mites listed above); Venoms: (Hymenoptera, yellow jacket, honey bee, wasp, hornet, fire ant); Other environmental insect allergens from cockroaches, fleas, mosquitoes, etc.; Bacteria such as streptococcal antigens; Parasites such as *Ascaris* antigen; Viral Antigens; Fungal spores; Drug Allergens; Antibiotics; penicillins and related compounds; other antibiotics; Whole Proteins such as hormones (insulin), enzymes (Streptokinase); all drugs and their metabolites capable of acting as incomplete antigens or haptens; Industrial Chemicals and metabolites capable of acting as haptens and stimulating the immune system (Examples are the acid anhydrides (such as trimellitic anhydride) and the isocyanates (such as toluene diisocyanate)); Occupational Allergens such as flour (i.e. Baker's asthma), castor bean, coffee bean, and industrial chemicals described above; flea allergens; and human proteins in non-human animals.

Allergens include but are not limited to cells, cell extracts, proteins, polypeptides, peptides, polysaccharides, polysaccharide conjugates, peptide and non-peptide mimics of polysaccharides and other molecules, small molecules, lipids, glycolipids, and carbohydrates. Many allergens, however, are protein or polypeptide in nature, as proteins and polypeptides are generally more antigenic than carbohydrates or fats.

Examples of specific natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poapratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

A "subject having asthma" is a subject that has a disorder of the respiratory system characterized by inflammation, narrowing of the airways and increased reactivity of the airways to inhaled agents. Asthma is frequently, although not exclusively associated with atopic or allergic symptoms. An "initiator" as used herein refers to a composition or environmental condition which triggers asthma. Initiators include, but are not limited to, allergens, cold temperatures, exercise, viral infections, $SO_2$.

In another aspect the invention provides methods for treating or preventing asthma or allergy in a hypo-responsive subject. As used herein, a hypo-responsive subject is one who has previously failed to respond to a treatment directed at treating or preventing asthma or allergy or one who is at risk of not responding to such a treatment. The treatment directed at treating or preventing asthma or allergy may be an asthma/allergy medicament, in which case the hypo-responsive subject is one who is hypo-responsive to an asthma/allergy medicament.

Other subjects who are hypo-responsive include those who are refractory to an asthma/allergy medicament. As used herein, the term "refractory" means resistant or failure to yield to treatment. Such subjects may be those who never responded to an asthma/allergy medicament (i.e., subjects who are non-responders), or alternatively, they may be those who at one time responded to an asthma/allergy medicament, but have since that time have become refractory to the medicament. In some embodiments, the subject is one who is refractory to a subset of medicaments. A subset of medicaments is at least one medicament. In some embodiments, a subset refers to 2, 3, 4, 5, 6, 7, 8, 9, or 10 medicaments.

In other embodiments, hypo-responsive subjects are elderly subjects, regardless of whether they have or have not previously responded to a treatment directed at treating or preventing asthma or allergy. Elderly subjects, even those who have previously responded to such treatment, are considered to be at risk of not responding to a future administration of this treatment. Similarly, neonatal subjects are also considered to be at risk of not responding to treatment directed at treating or preventing asthma or allergy.

In some embodiments, an immunostimulatory nucleic acid is administered to the hypo-responsive subject without the further administration of an asthma/allergy medicament. In yet other embodiments, an asthma/allergy medicament is administered to the hypo-responsive subject, in which case it may be administered substantially simultaneously (i.e., concurrently) with, or following the administration of the immunostimulatory nucleic acid.

An "asthma/allergy medicament" as used herein is a composition of matter which reduces the symptoms, inhibits the asthmatic or allergic reaction, or prevents the development of an allergic or asthmatic reaction. Various types of medicaments for the treatment of asthma and allergy are described in the Guidelines For The Diagnosis and Management of Asthma, Expert Panel Report 2, NIH Publication No. 97/4051, Jul. 19, 1997, the entire contents of which are incorporated herein by reference. The summary of the medicaments as described in the NIH publication is presented below.

In most embodiments the asthma/allergy medicament is useful to some degree for treating both asthma and allergy. Some asthma/allergy medicaments are preferably used in combination with the immunostimulatory nucleic acids to treat asthma. These are referred to as asthma medicaments. Asthma medicaments include, but are not limited, PDE-4 inhibitors, bronchodilator/beta-2 agonists, K+ channel openers, VLA-4 antagonists, neurokin antagonists, TXA2 synthesis inhibitors, xanthanines, arachidonic acid antagonists, 5 lipoxygenase inhibitors, thromboxin A2 receptor antagonists, thromboxane A2 antagonists, inhibitor of 5-lipox activation proteins, and protease inhibitors.

Bronchodilator/beta-2 agonists are a class of compounds which cause bronchodilation or smooth muscle relaxation. Bronchodilator/beta-2 agonists include, but are not limited to, salmeterol, salbutamol, albuterol, terbutaline, D2522/formoterol, fenoterol, bitolterol, pirbuerol methylxanthines and orciprenaline. Long-acting $\beta_2$ agonists and bronchodilators are compounds which are used for long-term prevention of symptoms in addition to the anti-inflammatory therapies. They function by causing bronchodilation, or smooth muscle relaxation, following adenylate cyclase activation and increase in cyclic AMP producing functional antagonism of bronchoconstriction. These compounds also inhibit mast cell mediator release, decrease vascular permeability and increase mucociliary clearance. Long-acting $\beta_2$ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. It is also believed that these compounds may effect eosinophilic infiltration into bronchial mucosa and decrease T-lymphocyte numbers in the epithelium. Dose-related acute toxicities are a particular problem with these types of compounds. As a result, routine serum concentration must be monitored in order to account for the toxicity and narrow therapeutic range arising from individual differences in metabolic clearance. Side effects include tachycardia, nausea and vomiting, tachyarrhythmias, central nervous system stimulation, headache, seizures, hematemesis, hyperglycemia and hypokalemia. Short-acting $\beta_2$ agonists/bronchodilators relax airway smooth muscle, causing the increase in air flow. These types of compounds are a preferred drug for the treatment of acute asthmatic systems. Previously, short-acting $\beta_2$ agonists had been prescribed on a regularly-scheduled basis in order to improve overall asthma symptoms. Later reports, however, suggested that regular use of this class of drugs produced significant diminution in asthma control and pulmonary function (Sears, et al. *Lancet;* 336:1391-6, 1990). Other studies showed that regular use of some types of $\beta_2$ agonists produced no harmful effects over a four-month period but also produced no demonstrable effects (Drazen, et al., *N. Eng. J. Med.;* 335:841-7, 1996). As a result of these studies, the daily use of short-acting $\beta_2$ agonists is not generally recommended. Short-acting $\beta_2$ agonists include, but are not limited to, albuterol, bitolterol, pirbuterol, and terbutaline. Some of the adverse effects associated with the mastration of short-acting $\beta_2$ agonists include tachycardia, skeletal muscle tremor, hypokalemia, increased lactic acid, headache, and hyperglycemia.

Other asthma/allergy medicaments are preferably used in combination with the immunostimulatory nucleic acids to treat allergy. These are referred to as allergy medicaments. Allergy medicaments include, but are not limited to, anti-histamines, steroids, and prostaglandin inducers. Anti-histamines are compounds which counteract histamine released by mast cells or basophils. These compounds are well known in the art and commonly used for the treatment of allergy. Anti-histamines include, but are not limited to, loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. Prostaglandin inducers are compounds which induce prostaglandin activity. Prostaglandins function by regulating smooth muscle relaxation. Prostaglandin inducers include, but are not limited to, S-575 1.

The asthma/allergy medicaments useful in combination with the immunostimulatory nucleic acids also include steroids and immunomodulators.

The steroids include, but are not limited to, beclomethasone, fluticasone, tramcinolone, budesonide, corticosteroids and budesonide. The combination of immunostimulatory nucleic acids and steroids are particularly well suited to the treatment of young subjects (e.g., children). To date, the use of steroids in children has been limited by the observation that some steroid treatments have been reportedly associated with growth retardation. Thus, according to the present invention, the immunostimulatory nucleic acids can be used in combination with growth retarding steroids, and can thereby provide a "steroid sparing effect." The combination of the two agents can result in lower required doses of steroids.

Corticosteroids are used long-term to prevent development of the symptoms, and suppress, control, and reverse inflammation arising from an initiator. Some corticosteroids can be administered by inhalation and others are administered systemically. The corticosteroids that are inhaled have an anti-inflammatory function by blocking late-reaction allergen and reducing airway hyper-responsiveness. These drugs also inhibit cytokine production, adhesion protein activation, and inflammatory cell migration and activation.

Corticosteroids include, but are not limited to, beclomethasome dipropionate, budesonide, flunisolide, fluticaosone, propionate, and triamcinoone acetonide. Although dexamethasone is a corticosteroid having anti-inflammatory action, it is not regularly used for the treatment of asthma/allergy in an inhaled form because it is highly absorbed, it has long-term suppressive side effects at an effective dose. Dexamethasone, however, can be used according to the invention for the treating of asthma/allergy because when administered in combination with immunostimulatory nucleic acids it can be administered at a low dose to reduce the side effects. Additionally, the immunostimulatory nucleic acid can be administered to reduce the side effects of dexamethasone at higher concentrations. Some of the side effects associated with corticosteroid include cough, dysphonia, oral thrush (candidiasis), and in higher doses, systemic effects, such as adrenal suppression, osteoporosis, growth suppression, skin thinning and easy bruising. (Barnes & Peterson, *Am. Rev. Respir. Dis.;* 148:S1-S26,1993; and Kamada et al., *Am. J. Respir. Crit. Care Med.;* 153:1739-48, 1996)

Systemic corticosteroids include, but are not limited to, methylprednisolone, prednisolone and prednisone. Cortosteroids are used generally for moderate to severe exacerbations to prevent the progression, reverse inflammation and speed recovery. These anti-inflammatory compounds include, but are not limited to, methylprednisolone, prednisolone, and prednisone. Cortosteroids are associated with reversible abnormalities in glucose metabolism, increased appetite, fluid retention, weight gain, mood alteration, hypertension, peptic ulcer, and rarely asceptic necrosis of femur. These compounds are useful for short-term (3-10 days) prevention of the inflammatory reaction in inadequately controlled persistent asthma. They also function in a long-term prevention of symptoms in severe persistent asthma to suppress and control and actually reverse inflammation. The side effects associated with systemic corticosteroids are even greater than those associated with inhaled corticosteroids. Side effects include, for instance, reversible abnormalities in glucose metabolism, increased appetite, fluid retention, weight gain, mood alteration, hypertension, peptic ulcer and asceptic necrosis of femur, which are associated with short-term use. Some side effects associated with longer term use include adrenal axis suppression, growth suppression, dermal thinning, hypertension, diabetes, Cushing's syndrome, cataracts, muscle weakness, and in rare instances, impaired immune function. It is recommended that these types of compounds be used at their lowest effective dose (guidelines for the diagnosis and management of asthma; expert panel report to; NIH Publication No. 97-4051; July 1997). The inhaled corticosteroids are believed to function by blocking late reaction to allergen and reducing airway hyper-responsiveness. Their also believed to reverse $\beta_2$-receptor downregulation and to inhibit microvascular leakage.

The immunomodulators include, but are not limited to, the group consisting of anti-inflammatory agents, leukotriene antagonists, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and, and downregulators of IgE.

Leukotriene modifiers are often used for long-term control and prevention of symptoms in mild persistent asthma. Leukotriene modifiers function as leukotriene receptor antagonists by selectively competing for LTD-4 and LTE-4 receptors. These compounds include, but are not limited to, zafirlukast tablets and zileuton tablets. Zileuton tablets function as 5-lipoxygenase inhibitors. These drugs have been associated with the elevation of liver enzymes and some cases of reversible hepatitis and hyperbilirubinemia. Leukotrienes are biochemical mediators that are released from mast cells, eosinophils, and basophils that cause contraction of airway smooth muscle and increase vascular permeability, mucous secretions and activate inflammatory cells in the airways of patients with asthma.

Other immunomodulators include neuropeptides that have been shown to have immunomodulating properties. Functional studies have shown that substance P, for instance, can influence lymphocyte function by specific receptor mediated mechanisms. Substance P also has been shown to modulate distinct immediate hypersensitivity responses by stimulating the generation of arachidonic acid-derived mediators from mucosal mast cells. J. McGillies, et al., Substance P and Immunoregulation, Fed. Proc. 46:196-9 (1987). Substance P is a neuropeptide first identified in 1931 by Von Euler and Gaddum. An unidentified depressor substance in certain tissue extracts, J. Physiol. (London) 72:74-87 (1931). Its amino acid sequence, Arg-Pro-Lys-Pro-Gln-Gln-Phe-Phe-Gly-Leu-Met-NH.sub.2 (Sequence Id. No. 1) was reported by Chang et al. in 1971. Amino acid sequence of substance P, Nature (London) New Biol. 232:86-87 (1971). The immunoregulatory activity of fragments of substance P has been studied by Siemion, et al. Immunoregulatory Activity of Substance P Fragments, Molec. Immunol. 27:887-890 (1990).

Another class of compounds is the down-regulators of IgE. These compounds include peptides or other molecules with the ability to bind to the IgE receptor and thereby prevent binding of antigen-specific IgE. Another type of downregulator of IgE is a monoclonal antibody directed against the IgE receptor-binding region of the human IgE molecule. Thus, one type of downregulator of IgE is an anti-IgE antibody or antibody fragment. Anti-IgE is being developed by Genentech. One of skill in the art could prepare functionally active antibody fragments of binding peptides which have the same function. Other types of IgE downregulators are polypeptides capable of blocking the binding of the IgE antibody to the Fc receptors on the cell surfaces and displacing IgE from binding sites upon which IgE is already bound.

One problem associated with downregulators of IgE is that many molecules don't have a binding strength to the receptor corresponding to the very strong interaction between the native IgE molecule and its receptor. The molecules having this strength tend to bind irreversibly to the receptor. However, such substances are relatively toxic since they can bind covalently and block other structurally similar molecules in the body. Of interest in this context is that the alpha. chain of the IgE receptor belongs to a larger gene family where i.e. several of the different IgG Fc receptors are contained. These receptors are absolutely essential for the defense of the body against i.e. bacterial infections. Molecules activated for covalent binding are, furthermore, often relatively unstable and therefore they probably have to be administered several times a day and then in relatively high concentrations in order to make it possible to block completely the continuously renewing pool of IgE receptors on mast cells and basophilic leukocytes.

These types of asthma/allergy medicaments are sometimes classified as long-term control medications or quick-relief medications. Long-term control medications include compounds such as corticosteroids (also referred to as glucocorticoids), methylprednisolone, prednisolone, prednisone, cromolyn sodium, nedocromil, long-acting $\beta_2$-agonists, methylxanthines, and leukotriene modifiers. Quick relief medications are useful for providing quick relief of symptoms arising from allergic or asthmatic responses. Quick relief medications include short-acting $\beta_2$ agonists, anticholinergics and systemic corticosteroids.

Chromolyn sodium and medocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from eosinophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratrapoium bromide. These compounds reverse only cholinerigically-mediated bronchospasm and do not modify any reaction to antigen. Side effects include drying of the mouth and respiratory secretions, increased wheezing in some individuals, blurred vision if sprayed in the eyes.

In addition to standard asthma/allergy medicaments other methods for treating asthma/allergy have been used either alone or in combination with established medicaments. One preferred, but frequently impossible, method of relieving allergies is allergen or initiator avoidance. Another method currently used for treating allergic disease involves the injection of increasing doses of allergen to induce tolerance to the allergen and to prevent further allergic reactions.

Allergen injection therapy (allergen immunotherapy) is known to reduce the severity of allergic rhinitis. This treatment has been theorized to involve the production of a different form of antibody, a protective antibody which is termed a "blocking antibody". Cooke, R A et al., Serologic Evidence of Immunity with Coexisting Sensitization in a Type of Human Allergy, Exp. Med. 62:733 (1935). Other attempts to treat allergy involve modifying the allergen chemically so that its ability to cause an immune response in the patient is unchanged, while its ability to cause an allergic reaction is substantially altered.

These methods, however, can take several years to be effective and are associated with the risk of side effects such as anaphylactic shock. The use of an immunostimulatory nucleic acid and asthma/allergy medicament in combination with an allergen avoids many of the side effects etc.

Commonly used allergy and asthma drugs which are currently in development or on the market are shown in Tables 2 and 3 respectively.

TABLE 2

Allergy Drugs in Development or on the Market

| MARKETER | BRAND NAME (GENERIC NAME) | MECHANISM |
| --- | --- | --- |
| Schering-Plough | Claritin ® + Claritin D ® (loratidine) | Anti-histamine |
|  | Vancenase ® (beclomethasone) | Steroid |
| UCB | Reactine (cetirizine)(US) | Anti-histamine |
|  | Zyrtec ® (cetirizine)(ex US) |  |
|  | Longifene (buclizine) | Anti-histamine |
|  | UCB 28754 (ceterizine alalogue) | Anti-histamine |
| Glaxo | Beconase (beclomethasone | Steroid |
|  | Flonase ® (fluticasone) | Steroid |
| Aventis | Allegra ® (fexofenadine) | Anti-histamine |
|  | Seldane ® (terfenadine) | Anti-histamine |
| Pfizer | Reactine (cetirizine) (US) | Anti-histamine |
|  | Zyrtec ®/Reactine (cetirizine)(ex US) |  |
|  | (both licensed from UCB) |  |
| Sepracor | Allegra ® (fexofenadine) | Anti-histamine |
|  | Desloratadine (lic to Schering-Plough) | Anti-histamine |
|  | Cetirizine (-) (lic to UCB) | Anti-histamine |
|  | Norastemizole (option to J&J not exercised, Nov. 17, 1999) | Anti-histamine |
| B. Ingelheim | Alesion (epinastine) | Anti-histamine |
| Aventis | Kestin (ebastine) (US) | Anti-histamine |
|  | Bastel (ebastme ) (Eu/Ger) |  |
|  | Nasacort ® (tramcinolone) | Steroid |
| Johnson & Johnson | Hismanol (astemizole) | Anti-histamine |
|  | Livostin ®/Livocarb (levocabastine) | Anti-histamine |
| AstraZeneca | Rhinocort (budesonide) (Astra) | Steroid |
| Merck | Rhinocort ® (budesonide) | Steroid |
| Eisai | Azeptin (azelastine) | Anti-histamine |
| Kissei | Rizaben (tranilast) | Anti-histamine |
| Shionogi | Triludan (terfenadine) | Anti-histamine |
|  | S-5751 | Prostaglandin inducer |
| Schwarz | Zolim ® (mizolastine) | Anti-histamine |
| Daiichi | Zyrtec ® (cetirizine) | Anti-histamine |
| Tanabe Seiyaku | Talion/TAU-284 (betatastine) | Anti-histamine |
| Sankyo** | CS 560 (Hypersensitizaion therapy for cedar pollen allergy) | Other |
| Asta Medica | Azelastine-MDPI (azelastine) | Anti-histamine |
| BASF | HSR 609 | Anti-histamine |
| SR Pharma | SRL 172 | Immunomodulation |
| Peptide Therapeutics | Allergy vaccine (allergy (hayfever, anaphylaxis, atopic asthma) | Downregulates specific IgE |
|  | Tolerizing peptide vaccine (rye grass peptide (T cell epitope)) | Immuno-suppressant |
| Coley Pharmaceutical Group | CpG DNA | Immunomodulation |
| Genetech | Anti-IgE | Down-regulator of IgE |
| SR Pharma | SRL 172 | Immunomodulation |

TABLE 3

Asthma Drugs in Development or on the Market

| MARKETER | BRAND NAME (GENERIC NAME) | MECHANISM |
| --- | --- | --- |
| Glaxo | Serevent ® (salmeterol) | Bronchodilator/beta-2 agonist |
|  | Flovent ® (fluticasone) | Steroid |
|  | Flixotide (fluticasone) |  |
|  | Becotide (betamethasone) | Steroid |
|  | Ventolin ® (salbutamol) | Bronchodilator/beta-2 agonist |
|  | Seretide ® (salmeterol + fluticasone) | Beta agonist + steroid |
|  | GW215864 | Steroid, hydolysable |

TABLE 3-continued

Asthma Drugs in Development or on the Market

| MARKETER | BRAND NAME (GENERIC NAME) | MECHANISM |
|---|---|---|
| | GW250495 | Steroid, hydolysable |
| | GW328267 | Adenosine A2 agonist |
| AstraZeneca | Bambec (bambuterol) (Astra) | |
| | Pulmicort (budesonide) (Astra) | Sterioid |
| | Bricanyl Turbuhaler (terbutaline) (Astra) | Bronchodilator/beta-2 agonist |
| | Accolate ® (zafirlukast) (Zeneca) | Leukotriene antagonist Slo-Phyllin (theophylline) |
| | Inspiryl (salbutamol) (Astra) | Bronchodilator/beta-2 agonist |
| | Oxis Turbuhaler (D2522/formoterol) | Bronchodilator/beta-2 agonist |
| | Symbicort ™ (pulmicort-oxis combination) | Steroid |
| | Roflepanide (Astra) | Steroid |
| | Bronica (seratrodast) | TXA2 synthesis inhibitor |
| | ZD 4407 (Zeneca) | 5 lipoxygenase inhibitor |
| B. Ingelheim | Atrovent ® (ipratropium) | Bronchodilator/anti-cholinergic |
| | Berodual (ipratropium + fenoterol) | Bronchodilator/anti-cholinergic |
| | Berotec (fenoterol) | Bronchodilator/beta-2 agonist |
| | Alupent (orciprenaline) | Bronchodilator/beta-2 agonist |
| | Ventilat (oxitropium) | Bronchodilator/anti-cholinergic |
| | Spiropent (clenbuterol) | Bronchodilator/beta-2 agonist |
| | Inhacort (flunisolide) | Steroid |
| | B1679/tiotropium bromide | |
| | RPR 106541 | Steroid |
| | BIIX 1 | Potassium channel |
| | BIIL284 | LTB-4 antagonist |
| Schering-Plough | Proventil ® (salbutamol) | Bronchodilator/beta-2 agonist |
| | Vanceril ® (becbomethasone) | Steroid |
| | Mometasone furoate | Steroid |
| | Theo-Dur ® (theophylline (w/Astra) | |
| | Uni-Dur ® (theophylline) | |
| | Asmanex ® (mometasone) | Steroid |
| | CDP 835 (lic from Celltech) | Anti-IL-5 Mab |
| RPR (Aventis) | Intal ® (disodium cromoglycate) | Anti-inflammatory |
| | Intal ® /Aarane (disodium cromoglycate) | |
| | Tilade (nedocromil sodium) | Anti-inflammatory |
| | Azmacort ® (triamcinolone acetonide) | Steroid |
| | RP 73401 | PDE-4 inhibitor |
| Novartis | Zaditen ® (ketotifen) | Anti-inflammatory |
| | Azmacort ® (triamoinolone) | Sterioid |
| | Foradil ® (formoterol) (lic from Yamanouchi) | Bronchodilator/beta-2 agonist |
| | E25 | Anit-IgE |
| | KCO 912 | K + Channel opener |
| Merck | Singulair ® (montelukast) | Leukotriene antagonist |
| | Pulinicort Turbuhaler (budesonide) | Steroid |
| | Slo-Phyllin (theophylline) | |
| | Symbicort ™ (Pulmicort-Oxis combination) | Steroid |
| | Oxis Turbuhaler (D2522/formoterol) | Bronchodilator/beta-2 agonist |
| | Roflepanide | Steroid |
| | VLA-4 antagonist (lic from Biogen) | VLA-4 antagonist |
| ONO | Onon (pranlukast) | Leukotriene antagonist |
| | Vega (ozagrel) | TXA2 synthesis inhibitor |
| Fujisawa | Intal ® (chromoglycate) | Anti-inflammatory |
| | FK 888 | Neurokin antagonist |
| Forest Labs | Aerobid ® (flunisolide) | Steroid |
| IVAX | Ventolin ® (salbutamol) | Bronchodilator/beta-2 agonist |
| | Becotide (beclomethasone Easi-Breathe) | Steroid |
| | Serevent ® (salmeterol) | Bronchodilator/beta-2 agonist |
| | Flixotide (fluticasone) | Steroid |
| | Budesonide Dry Powder Inhaler | Steroid |
| | Salbutamol Dry Powder Inhaler | Bronchodilator/beta-2 agonist |
| Alza | Volmax (salbutamol) | Bronchodilator/beta-2 agonist |
| Altana | Euphyllin (theophylline) | Xanthanine |
| | Ciclesonide | Arachidonic acid antagonist |
| | BY 217 | PDE 4 inhibitor |
| | BY 9010N (ciclesonide) | Steroid (nasal) |
| Tanabe Seiyaku | Flucort ® (fluocinolone acetonide) | Steroid |
| Kissei | Domenan (ozagrel) | TXA2 synthesis inhibitor |
| Abbott | Zyflo ® (zileuton) (4X/day dosing, not competitive w/ Singulair or Accolate, no further interest in this area) | 5 lipoxygenase inhibitor |
| Asta Medica | Aerobec (beclomethasone dipropionate) (w/3M) | |
| | Allergodil (azelastine) | |

TABLE 3-continued

Asthma Drugs in Development or on the Market

| MARKETER | BRAND NAME (GENERIC NAME) | MECHANISM |
|---|---|---|
| | Allergospasmin (sodium cromoglycate reproterol) | |
| | Bronchospasmin (reproterol) | |
| | Salbulair (salbutamol sulphate) (w/3M) | |
| | TnNasal (triamcinolone) | Steroid |
| | Formoterol-MDPI | Beta 2 adrenoceptor agonist |
| | Budesonide-MDPI | |
| UCB | Atenos/Respecal (tulobuerol) | Bronchodilator/beta-2 agonist |
| Recordati | Theodur (theophylline) | Xanthine |
| Medeva | Clickhalers Asmasal, Asmabec (salbutamol beclomethasone diproprionate, dry inhaler) | Steroid |
| Eisai | E6123 | PAF receptor antagonist |
| Sankyo | Zaditen ® (ketotifen) | Anti-inflammatory |
| | CS 615 | Leukotriene antagonist |
| Shionogi | Anboxan/S 1452 (domitroban) | Thromboxin A2 receptor antagonist |
| Yamanouchi | YM 976 | PDE 4 inhibitor |
| | YM 158 | Leukotniene D4/thromboxan 2 dual antagonist |
| 3M Pharma | Exirel (pirbuterol) | |
| Hoechst (Aventis) | Autoinhalers (3M albuterol projects) | Bronchodilator/beta-2 agonist |
| SmithKline Beecham | Ariflo ® | PDE-4 inhibitor |
| | SB 240563 | Anti-IL5 MAb (humanized) |
| | SB 240683 | Anti-IL4 Mab |
| | IDEC 151/clenoliximab | Anti-CD4 MAb, primatised |
| Roche | Anti-IgE(GNE)/CGO51901 | Down-regulator of IgE |
| Sepracor | Fomoterol (R,R) | Beta 2 adrenoceptor agonist |
| | Xopenex ® (levalbuterol) | Bet 2 adrenoceptor agonist |
| Bayer | BAY U 3405 (ramatroban) | Thromboxane A2 antagonist |
| | BAY 16-9996 (once monthly dosing) | IL4 mutein |
| | BAY 19-8004 | PDE-4 inhibitor |
| SR Pharma | SRL 172 | Immunomodulation |
| Immunex | Nuvance ® | Soluble IL-4 receptor (immunomodulator) |
| Biogen | Anti-VLA-4 | Immunosuppressant |
| Vanguard | VML 530 | Inhibitor of 5-lipox activation protein |
| Recordati | Respix (zafirlukast) | Leukotriene antagonist |
| Genentech | Anti-IgE MAb | Down-regulator of IgE |
| Warner Lambert | CI-1018 | PDE 4 inhibitor |
| Celltech/ Chiroscience | CDP 835/SCH 55700 (anti-IL-5) (lic to Schering-Plough) | IL-5 antagonist Mab |
| | D 4418 (w/ Schering-Plough) | PDE 4 inhibitor |
| | CDP 840 (Celltech) | PDE 4 inhibitor |
| AHP | Pda-641 (asthma steroid replacement) | |
| Peptide Therapeutics | RAPID Technology Platform | Protease inhibitors |
| Coley Pharmaceutical Group | CpG DNA | Immunomodulation |

In some cases the subject is exposed to an allergen in addition to being treated with the immunostimulatory nucleic acid and the asthma/allergy medicament. In this case the subject is said to be exposed to the allergen. As used herein, the term "exposed to" refers to either the active step of contacting the subject with an allergen or the passive exposure of the subject to the allergen in vivo. Methods for the active exposure of a subject to an allergen are well-known in the art. In general, an allergen is administered directly to the subject by any means such as intravenous, intramuscular, oral, transdermal, mucosal, intranasal, intratracheal, or subcutaneous administration. The allergen can be administered systemically or locally. Methods for administering the allergen and the immunostimulatory nucleic acid/asthma/allergy medicament are described in more detail below. A subject is passively exposed to an allergen if an allergen becomes available for exposure to the immune cells in the body. A subject may be passively exposed to an allergen, for instance, by entry of an allergen into the body when the allergen is present in the environment surrounding the subject, i.e. pollen.

The methods in which a subject is passively exposed to an allergen can be particularly dependent on timing of administration of the immunostimulatory nucleic acid and the asthma/allergy medicament. For instance, in a subject at risk of developing an allergic or asthmatic response, the subject may be administered the immunostimulatory nucleic acid and the asthma/allergy medicament on a regular basis when that risk is greatest, i.e., during pollen allergy season. Additionally the immunostimulatory nucleic acid and the asthma/allergy medicament may be administered to travelers before they travel to a destination where they are at risk of exposure to a particular allergen.

As used herein, the term "prevent", "prevented", or "preventing" when used with respect to the treatment of an allergic or asthmatic disorder refers to a prophylactic treatment which increases the resistance of a subject to an allergen or initiator or, in other words, decreases the likelihood that the subject will develop an allergic or asthmatic response to the allergen or initiator as well as a treatment after the allergic or asthmatic disorder has begun in order to fight the allergy/asthma, e.g., reduce or eliminate it altogether or prevent it from becoming worse.

The term "substantially purified" as used herein refers to a molecular species which is substantially free of other proteins, lipids, carbohydrates or other materials with which it is naturally associated. One skilled in the art can purify allergenic polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the allergenic polypeptide can also be determined by amino-terminal amino acid sequence analysis.

The allergen and/or polypeptide asthma/allergy medicament may be in the form of a polypeptide when administered to the subject or it may be encoded by a nucleic acid vector. If the nucleic acid vector is administered to the subject the protein is expressed in vivo. Minor modifications of the primary amino acid sequences of polypeptide allergens may also result in a polypeptide which has substantially equivalent allergenic activity as compared to the unmodified counterpart polypeptide. Such modifications may be deliberate, as by site-directed mutagenesis, or may be spontaneous.

The nucleic acid encoding the allergen or asthma/allergy medicament is operatively linked to a gene expression sequence which directs the expression of the protein within a eukaryotic cell. The "gene expression sequence" is any regulatory nucleotide sequence, such as a promoter sequence or promoter-enhancer combination, which facilitates the efficient transcription and translation of the protein which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, b-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

As used herein, the nucleic acid sequence encoding the protein and the gene expression sequence are said to be "operably linked" when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the gene sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to a specific nucleic acid sequence if the gene expression sequence were capable of effecting transcription of that nucleic acid sequence such that the resulting transcript is translated into the desired protein or polypeptide.

The immunostimulatory nucleic acids may also be delivered to the subject in the form of a plasmid vector. In some embodiments, one plasmid vector could include both the immunostimulatory nucleic acid and a nucleic acid encoding a protein asthma/allergy medicament and/or an allergen. In other embodiments, separate plasmids could be used. In yet other embodiments, no plasmids could be used.

The compositions of the invention may be delivered to the immune system or other target cells alone or in association with a vector. In its broadest sense, a "vector" is any vehicle capable of facilitating the transfer of the compositions to the target cells. The vector generally transports the nucleic acid to the immune cells with reduced degradation relative to the extent of degradation that would result in the absence of the vector.

In general, the vectors useful in the invention are divided into two classes: biological vectors and chemical/physical vectors. Biological vectors and chemical/physical vectors are useful for delivery/uptake of nucleic acids, asthma/allergy medicaments, and/or allergens to/by a target cell.

Biological vectors include, but are not limited to, plasmids, phagemids, viruses, other vehicles derived from viral or bacterial sources that have been manipulated by the insertion or incorporation of nucleic acid sequences, and free nucleic acid fragments which can be attached to nucleic acid sequences. Viral vectors are a preferred type of biological vector and include, but are not limited to, nucleic acid sequences from the following viruses: retroviruses, such as: Moloney murine leukemia virus; Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One can readily employ other viral vectors not named but known in the art.

Preferred viral vectors are based on non-cytopathic eukaryotic viruses in which non-essential genes have been replaced with a nucleic acid of interest. Non-cytopathic viruses include retroviruses, the life cycle of which involves reverse transcription of genomic viral RNA into DNA with subsequent proviral integration into host cellular DNA. Retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other biological vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as *Salmonella* can be transfected with the plasmid and used as delivery vehicles. The bacterial delivery vehicles can be administered to a host subject orally or by other administration means. The bacteria deliver the plasmid to immune cells, e.g. B cells, dendritic cells, likely by passing through the gut barrier. High levels of immune protection have been established using this methodology. Such methods of delivery are useful for the aspects of the invention utilizing systemic delivery of allergen, immunostimulatory nucleic acid and/or other therapeutic agent.

In addition to the biological vectors, chemical/physical vectors may be used to deliver a nucleic acid, asthma/allergy medicament, and/or allergen to a target cell and facilitate uptake thereby. As used herein, a "chemical/physical vector" refers to a natural or synthetic molecule, other than those derived from bacteriological or viral sources, capable of delivering the nucleic acid, asthma/allergy medicament, and/or allergen to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., *Trends Biochem. Sci.*, (1981) 6:77).

Liposomes may be targeted to a particular tissue by coupling the liposome to a specific ligand such as a monoclonal antibody, sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. Additionally, the vector may be coupled to a nuclear targeting peptide, which will direct the vector to the nucleus of the host cell.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2, 3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. *in Trends in Biotechnology*, (1985) 3:235-241.

In one embodiment, the vehicle is a biocompatible microparticle or implant that is suitable for implantation or administration to the mammalian recipient. Exemplary bioerodible implants that are useful in accordance with this method are described in PCT International application no. PCT/US/03307 (Publication No. WO95/24929, entitled "Polymeric Gene Delivery System". PCT/US/0307 describes a biocompatible, preferably biodegradable polymeric matrix for containing an exogenous gene under the control of an appropriate promoter. The polymeric matrix can be used to achieve sustained release of the exogenous gene in the patient.

The polymeric matrix preferably is in the form of a microparticle such as a microsphere (wherein the a nucleic acid, asthma/allergy medicament, and/or allergen is dispersed throughout a solid polymeric matrix) or a microcapsule (wherein the a nucleic acid, asthma/allergy medicament, and/or allergen is stored in the core of a polymeric shell). Other forms of the polymeric matrix for containing the a nucleic acid, asthma/allergy medicament, and/or allergen include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nucleic acid, asthma/allergy medicament, and/or allergen are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time.

In another embodiment the chemical/physical vector is a biocompatible microsphere that is suitable for delivery, such as oral or mucosal delivery. Such microspheres are disclosed in Chickering et al., *Biotech. And Bioeng.*, (1996) 52:96-101 and Mathiowitz et al., *Nature*, (1997) 386:.410-414 and PCT Patent Application WO97/03702.

Both non-biodegradable and biodegradable polymeric matrices can be used to deliver the nucleic acid, asthma/allergy medicament, and/or allergen to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver a nucleic acid in a form that is more efficiently taken up by the cell or, more preferably, in combination with one or more of the above-described vectors.

Other exemplary compositions that can be used to facilitate uptake by a target cell of the nucleic acid, asthma/allergy medicament, and/or allergen include calcium phosphate and other chemical mediators of intracellular transport, microinjection compositions, electroporation and homologous recombination compositions (e.g., for integrating a nucleic acid into a preselected location within the target cell chromosome).

The immunostimulatory nucleic acid and/or the asthma/allergy medicament the antigen and/or other therapeutics may be administered alone (e.g. in saline or buffer) or using any delivery vectors known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998).

The immunostimulatory nucleic acid and asthma/allergy medicament can be combined with other therapeutic agents such as adjuvants to enhance immune responses even further. The immunostimulatory nucleic acid, asthma/allergy medicament and other therapeutic agent may be administered simultaneously or sequentially. When the other therapeutic agents are administered simultaneously they can be administered in the same or separate formulations, but are administered at the same time. The other therapeutic agents are administered sequentially with one another and with the immunostimulatory nucleic acid and asthma/allergy medicament, when the administration of the other therapeutic agents and the immunostimulatory nucleic acid and asthma/allergy medicament is temporally separated. The separation in time between the administration of these compounds may be a matter of minutes or it may be longer. Other therapeutic agents include but are not limited to non-nucleic acid adjuvants, cytokines, antibodies, antigens, etc.

A "non-nucleic acid adjuvant" is any molecule or compound except for the immunostimulatory nucleic acids described herein which can stimulate the humoral and/or cellular immune response. Non-nucleic acid adjuvants include, for instance, adjuvants that create a depo effect, immune stimulating adjuvants, adjuvants that create a depo effect and stimulate the immune system and mucosal adjuvants.

An "adjuvant that creates a depo effect" as used herein is an adjuvant that causes an antigen or allergen to be slowly released in the body, thus prolonging the exposure of immune cells to the antigen or allergen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montamide adjuvants (e.g., Montamide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An "immune stimulating adjuvant" is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the $21^{st}$ peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland); and Leishmania elongation factor (a purified *Leishmania* protein; Corixa Corporation, Seattle, Wash.).

"Adjuvants that create a depo effect and stimulate the immune system" are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "non-nucleic acid mucosal adjuvant" as used herein is an adjuvant other than an immunostimulatory nucleic acid that is capable of inducing a mucosal immune response in a subject when administered to a mucosal surface in conjunction with an antigen or allergen. Mucosal adjuvants include but are not limited to Bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler BD, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*)(Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worster, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montamide adjuvants (e.g., Montamide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the immunostimulatory nucleic acids and asthma/allergy medicaments. The cytokines can be administered directly with immunostimulatory nucleic acids or may be administered in the form of a nucleic acid vector that encodes the cytokine, such that the cytokine can be expressed in vivo. In one embodiment, the cytokine is administered in the form of a plasmid expression vector. The term "cytokine" is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18 granulocyte-macrophage colony stimulating factor (GM-CSF), granulocyte colony stimulating factor (GCSF), interferon-γ (γ-IFN), IFN-a, tumor necrosis factor (TNF), TGF-β, FLT-3 ligand, and CD40 ligand. Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. In some embodiments it is preferred that the cytokine be a Th1 cytokine.

The term "effective amount" of an immunostimulatory nucleic acid and an asthma/allergy medicament refers to the amount necessary or sufficient to realize a desired biologic effect. For example, an effective amount of an immunostimulatory nucleic acid and an asthma/allergy medicament for treating or preventing asthma or preventing is that amount necessary to prevent the development of IgE in response to an allergen or initiator upon exposure to the allergen or initiator is that amount necessary to cause the shift from Th2 to Th1 response in response to an allergen or initiator.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular immunostimulatory nucleic acid or asthma/allergy medicament being administered (e.g. the type of nucleic acid, i.e. a CpG nucleic acid, the number of unmethylated CpG motifs or their location in the nucleic acid, the degree of modification of the backbone to the oligonucleotide the type of medicament), the size of the subject, or the severity of the disease or condition. One of ordinary skill in the art can empirically determine the effective amount of a particular immunostimulatory nucleic acid and/or asthma/allergy medicament and/or other therapeutic agent without necessitating undue experimentation.

Depending upon the aspect of the invention, the immunostimulatory nucleic acid and asthma/allergy medicament may be administered in a synergistic amount effective to treat or prevent asthma or allergy. A synergistic amount is that amount which produces a physiological response that is greater than the sum of the individual effects of either the immunostimulatory nucleic acid or the asthma/allergy medicament alone. For instance, in some embodiments of the invention, the physiological effect is a reduction in IgE levels. A synergistic amount is that amount which produces a reduction in IgE that is greater than the sum of the IgE reduced by either the immunostimulatory nucleic acid or the asthma/allergy medicament alone. In other embodiments, the physiological result is a shift from Th2 cytokines, such as IL-4 and IL-5, to Th1 cytokines, such as IFN-γ and IL-12. The synergistic amount in this case is that amount which produces the shift to a Th1 cytokine that is greater than the sum of the shift produced by either the immunostimulatory nucleic acid or the asthma/allergy medicament alone. In other embodiments the physiological result is a decrease in eosinophilia, hyperreactivity, or lung function.

In some embodiments of the invention, the immunostimulatory nucleic acid is administered in an effective amount for preventing bacterial or viral infection. Immunostimulatory nucleic acids are known to be useful for preventing bacterial and viral infections. Bacterial and viral infections exacerbate and/or induce allergy and/or asthma. In this aspect of the invention, the immunostimulatory nucleic acid is administered to the subject in an amount effective to prevent bacterial and viral infection and the asthma/allergy medicament is administered to the subject when symptoms of allergy or asthma appear. Thus, the immunostimulatory nucleic acid is administered to the subject and then the asthma/allergy medicament is subsequently administered to the subject or they are administered together at the same time. This method is particularly useful in subjects such as children and immunocompromised subjects, or elderly subjects, who are particularly susceptible to bacterial or viral disease.

In aspects of the invention directed at treating subjects in anticipation of an asthmatic or allergic event or season (e.g., in anticipation of the hay-fever season), the subjects may be administered an immunostimulatory nucleic acid in an effective amount for preventing the asthma or allergy. In related embodiments of this method, an asthma/allergy medicament is also administered to the subject. In these latter instances, the amount of the immunostimulatory nucleic acid administered may be that amount necessary to reduce the effective dose of the asthma/allergy medicament which is required to treat or prevent the asthma or allergy.

Thus, in these embodiments, the immunostimulatory nucleic acid potentiates the effect of the asthma/allergy medicament. The ability to potentiate the effect of an asthma/allergy medicament is useful since it allows for a reduction in the administered dose of an asthma/allergy medicament with the same or better therapeutic result. As an example, if the dose of the medicament is lowered, then so too are the side-effects of the medicament such as, for example, drowsiness, nervousness, dizziness or, in some instances, sleeplessness. Similarly, the administration of a lowered dose of the asthma/allergy medicament may make the medicament more compatible with the administration of other medicaments such as those which are currently not simultaneously prescribed or administered with asthma or allergy medicaments. In some instances, these include certain medicaments which are prescribed for depression, psychiatric or emotional conditions or Parkinson's disease and which contain monoamine oxidase inhibitor (MAOI). Similarly, the ability to potentiate the effect of the asthma/allergy medicament, thereby leading to a decreased effective dose, is useful for treating a wide range of subjects who have previously been contraindicated for such treatment, including subjects with heart disease or diabetes, subjects who have difficulty in urinating due to prostate gland enlargement, and subjects who are pregnant or who are nursing (i.e., breast-feeding). Thus, the invention provides a method for administering to a subject a dose of an asthma/allergy medicament which if administered alone, or if administered without previous administration of an immunostimulatory nucleic acid to the same subject, would be ineffective (and would be considered sub-therapeutic).

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day.

In some instances, a sub-therapeutic dosage of the immunostimulatory nucleic acid and the asthma/allergy medicament are used. It has been discovered according to the invention, that when the two classes of drugs are used together, they can be administered in sub-therapeutic doses and still produce a desirable therapeutic result, a "sub-therapeutic dose" as used herein refers to a dosage which is less than that dosage which would produce a therapeutic result in the subject, if administered alone. Thus, the sub-therapeutic dose of an asthma/allergy medicament is one which would not produce the desired therapeutic result in the subject. Therapeutic doses of asthma/allergy medicaments are well known in the field of medicine for the treatment of asthma and allergy. These dosages have been extensively described in references such as Remington's Pharmaceutical Sciences, 18th ed., 1990; as well as many other medical references relied upon by the medical profession as guidance for the treatment of asthma and allergy. Therapeutic dosages of immunostimulatory nucleic acids, have also been described in the art and methods for identifying therapeutic dosages in subjects are described in more detail above.

In other aspects, the method of the invention involves administering a high dose of an asthma/allergy medicament to a subject, without inducing side effects. Ordinarily, when an asthma/allergy medicament is administered in a high dose, a variety of side effects can occur. (Discussed in more detail above, as well as in the medical literature). As a result of these side effects, the asthma/allergy medicament is not administered in such high doses, no matter what therapeutic benefits are derived. It was discovered, according to the invention, that such high doses of asthma/allergy medicaments which ordinarily induce side effects can be administered without inducing the side effects as long as the subject also receives an immunostimulatory nucleic acid. The type and extent of the side effects ordinarily induced by the asthma/allergy medicament will depend on the particular asthma/allergy medicament used.

In other embodiments of the invention, the immunostimulatory nucleic acid is administered on a routine schedule. The asthma/allergy medicament may also be administered on a routine schedule, but alternatively, may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the immunostimulatory nucleic acid on a daily basis, every two days, every three days, every four days, every five days, every six days, a weekly basis, a bi-weekly basis, a monthly basis, a bimonthly basis or any set number of days or weeks there-between, every two months, three months, four months, five months, six months, seven months, eight months, nine months, ten months, eleven months, twelve months, etc. Alternatively, the predetermined routine schedule may involve administration of the immunostimulatory nucleic acid on a daily basis for the first week, followed by a monthly basis for several months, and then every three months after that. Any particular combination would be covered by the routine schedule as long as it is determined ahead of time that the appropriate schedule involves administration on a certain day.

In some aspects of the invention, the immunostimulatory nucleic acid is administered to the subject in anticipation of an asthmatic or allergic event in order to prevent an asthmatic or allergic event. The asthmatic or allergic event may be, but need not be limited to, an asthma attack, seasonal allergic rhinitis (e.g., hay-fever, pollen, ragweed hypersensitivity) or perennial allergic rhinitis (e.g., hypersensitivity to allergens such as those described herein). In some instances, the immunostimulatory nucleic acid is administered substantially prior to an asthmatic or an allergic event. As used herein, "substantially prior" means at least six months, at least five months, at least four months, at least three months, at least two months, at least one month, at least three weeks, at least two weeks, at least one week, at least 5 days, or at least 2 days prior to the asthmatic or allergic event.

Similarly, the asthma/allergy medicament may be administered immediately prior to the asthmatic or allergic event (e.g., within 48 hours, within 24 hours, within 12 hours, within 6 hours, within 4 hours, within 3 hours, within 2 hours, within 1 hour, within 30 minutes or within 10 minutes of an asthmatic or allergic event), substantially simultaneously with the asthmatic or allergic event (e.g., during the time the subject is in contact with the allergen or is experiencing the asthma or allergy symptoms) or following the asthmatic or allergic event.

In some embodiments, the immunostimulatory nucleic acid and the asthma/allergy medicament are both administered to a subject. The timing of administration of both may vary. In some embodiments, it is preferred that the asthma/allergy medicament be administered subsequent to the administration of the immunostimulatory nucleic acid. In some embodiments, the immunostimulatory nucleic acid is administered to the subject prior to as well as either substantially simultaneously with or following the administration of the asthma/allergy medicament. The administration of the immunostimulatory nucleic acid and the asthma/allergy medicament may also be mutually exclusive of each other so that at any given time during the treatment period, only one of these agents is active in the subject. Alternatively, and preferably in some instances, the administration of the two agents overlaps such that both agents are active in the subject at the same time.

In some embodiments, the immunostimulatory nucleic acid is administered on a weekly or biweekly basis and the asthma/allergy medicament is administered more frequently (e.g., on a daily basis). However, if the dose of immunostimulatory nucleic acid is reduced sufficiently, it is possible that the immunostimulatory nucleic acid is administered as frequently as the asthma/allergy medicament, albeit at a reduced dose.

In other aspects, the invention relates to kits that are useful in the treatment of asthma and/or allergy. One kit of the invention includes a sustained release vehicle containing an immunostimulatory nucleic acid and a container housing an asthma/allergy medicament and instructions for timing of administration of the immunostimulatory nucleic acid in the asthma/allergy medicament. A sustained release vehicle is used herein in accordance with its prior art meaning of any device which slowly releases the immunostimulatory nucleic acid.

Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The asthma/allergy medicament is housed in at least one container. The container may be a single container housing all of the asthma/allergy medicament together or it may be multiple containers or chambers housing individual dosages of the asthma/allergy medicament, such as a blister pack. The kit also has instructions for timing of administration of the asthma/allergy medicament. The instructions would direct the subject having asthma/allergy or at risk of asthma/allergy to take the asthma/allergy medicament at the appropriate time. For instance, the appropriate time for delivery of the medicament may be as the symptoms occur. Alternatively, the appropriate time for administration of the medicament may be on a routine schedule such as monthly or yearly.

Another kit of the invention includes at least one container housing an immunostimulatory nucleic acid and at least one container housing an asthma/allergy medicament and instructions for administering the compositions in effective amounts for inducing a synergistic immune response in the subject. The immunostimulatory nucleic acid and asthma/allergy medicament may be housed in single containers or in separate compartments or containers, such as single dose compartments. The instructions in the kit direct the subject to take the immunostimulatory nucleic acid and the asthma/allergy medicament in amounts which will produce a synergistic immune response. The drugs may be administered simultaneously or separately as long as they are administered close enough in time to produce a synergistic response.

In other aspects of the invention, a composition is provided. The composition includes an immunostimulatory nucleic and an asthma/allergy medicament formulated in a pharmaceutically-acceptable carrier and present in the composition in an effective amount for preventing or treating an immune or inflammatory response associated with exposure to a mediator of asthma or allergy. The effective amount for preventing or treating an immune or inflammatory response is that amount which prevents, inhibits completely or partially the induction of the immune or inflammatory response or prevents an increase in the immune or inflammatory response associated with asthma or allergy. An immune or inflammatory response associated with asthma or allergy includes an induction in IgE, an increase in Th2 cytokines, etc. A mediator of asthma or allergy includes asthma initiators and allergens. An example of a composition is one which comprises an immunostimulatory nucleic acid, such as a CpG nucleic acid, and an asthma/allergy medicament, such as an anti-IgE agent (e.g., an anti-IgE antibody or antibody fragment). Such a composition can be administered to a subject on a routine basis such as monthly, bimonthly, or quarterly.

For any compound described herein a therapeutically effective amount can be initially determined from cell culture assays. For instance the effective amount of immunostimulatory nucleic acid useful for inducing B cell activation can be assessed using the in vitro assays with respect to stimulation index in comparison to known immunostimulatory acids. The stimulation index can be used to determine an effective amount of the particular oligonucleotide for the particular subject, and the dosage can be adjusted upwards or downwards to achieve the desired levels in the subject. Therapeutically effective amounts can also be determined from animal models. A therapeutically effective dose can also be determined from human data for immunostimulatory nucleic acids which have been tested in humans (human clinical trials have been initiated) and for compounds which are known to exhibit similar pharmacological activities, such as other adjuvants, e.g., LT and other antigens for vaccination purposes. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan. Most of the asthma/allergy medicaments have been identified. These amounts can be adjusted when they are combined with immuno-stimulatory nucleic acids by routine experimentation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

Asthma/allergy medicaments and immunostimulatory nucleic acids can be administered by any ordinary route for administering medications. Preferably, they are inhaled, ingested or administered by local routes (such as nasal drops) or by systemic routes. Systemic routes include oral and parenteral. Inhaled medications are preferred in some embodiments because of the direct delivery to the lung, the site of inflammation, primarily in asthmatic patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. As used herein, delivery to the nasal passages or the lungs via nasal drops or inhalation are referred to as local administration. Although it is possible that delivery to the lung (e.g., via inhalation) can eventually result in systemic delivery of the agent, the administration is still considered "local" in the sense that the majority of the agent is initially presented to the lung tissue or the nasal passages, prior to any secondary systemic effects. In some preferred embodiments, the immunostimulatory nucleic acid is administered locally, such as for example by nasal drops or inhalation.

For use in therapy, an effective amount of the immunostimulatory nucleic acid can be administered to a subject by any mode that delivers the nucleic acid to the desired surface, e.g., mucosal, systemic. "Administering" the pharmaceutical composition of the present invention may be accomplished by any means known to the skilled artisan. Preferred routes of administration include but are not limited to oral, parenteral, intramuscular, intranasal, intratracheal, inhalation, ocular, vaginal, and rectal.

For oral administration, the compounds (i.e., immunostimulatory nucleic acids, asthma/allergy medicament, other therapeutic agent) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the therapeutic, such as the immunostimulatory capacity of the nucleic acids (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The immunostimulatory nucleic acids and asthma/allergy medicament may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an immunostimulatory nucleic acid and optionally asthma/allergy medicament and/or other therapeutic agents optionally included in a pharmaceutically-acceptable carrier. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for treating an asthmatic event in a hypo-responsive subject having allergic asthma, comprising:

administering to a hypo-responsive subject having allergic asthma a CpG immunostimulatory nucleic acid having the formula $$5'\ N_1X_1X_2CGX_3X_4N_2\ 3'$$

wherein the cytosine of the CG dinucleotide is unmethylated, $X_1$ and $X_2$ are both purines and $X_3$ and $X_4$ are both pyrimidines, and $N_1$ and $N_2$ are nucleic acid sequences composed of 0-25 nucleotides each, in an effective amount for treating an asthmatic event, wherein the hypo-responsive subject is refractory to an asthma/allergy medicament, and wherein the CpG immunostimulatory nucleic acid is 8-100 nucleotides.

2. The method of claim 1, wherein the immunostimulatory nucleic acid has a modified backbone.

3. The method of claim 2, wherein the modified backbone is a phosphate modified backbone.

4. The method of claim 3, wherein the phosphate modified backbone is a phosphorothioate modified backbone.

5. The method of claim 1, further comprising administering to the hypo-responsive subject an asthma/allergy medicament.

6. The method of claim 5, wherein the asthma/allergy medicament is administered in a sub-therapeutic amount.

7. The method of claim 5, wherein the asthma/allergy medicament is an asthma medicament.

8. The method of claim 5, wherein the asthma/allergy medicament is an allergy medicament.

9. The method of claim 5, wherein the asthma/allergy medicament is selected from the group consisting of a steroid and an immunomodulator.

10. The method of claim 9, wherein the steroid is selected from the group consisting of beclomethasone, fluticasone, tramcinolone, budesonide and budesonide.

11. The method of claim 9, wherein the immunomodulator is selected from the group consisting of an anti-inflammatory agent, a leukotriene antagonist, an IL-4 mutein, a soluble IL-4 receptor, an immunosuppressant, an anti-IL-4 antibody, an IL-4 antagonist, an anti-IL-5 antibody, a soluble IL-13 receptor-Fc fusion protein, an anti-IL-9 antibody, a CCR3 antagonist, a CCR5 antagonist, a VLA-4 inhibitor and a downregulator of IgE.

12. The method of claim 11, wherein the downregulator of IgE is an anti-Ig antibody or a fragment thereof.

13. The method of claim 11, wherein the immunosuppressant is a tolerizing peptide vaccine.

14. The method of claim 5, wherein the asthma/allergy medicament is a medicament selected from the group consisting of a PDE-4 inhibitor, a bronchodilator/beta-2 agonist, a K+ channel opener, a VLA-4 antagonist, a neurokin antagonist, a thromboxane A2 synthesis inhibitor, xanthanine, an arachidonic acid antagonist, a 5 lipoxygenase inhibitor, a thromboxane A2 receptor antagonist, a thromboxane A2 antagonist, an inhibitor of 5-lipox activation protein and a protease inhibitor.

15. The method of claim 14, wherein the bronchodilator/beta-2 agonist is selected from the group consisting of salmeterol, salbutamol, terbutaline, D2522/formoterol, fenoterol and orciprenaline.

16. The method of claim 5, wherein the asthma/allergy medicament is a medicament selected from the group consisting of an anti-histamine and a prostaglandin inducer.

17. The method of claim 16, wherein the anti-histamine is selected from the group consisting of loratidine, cetirizine, buclizine, a ceterizine analogue, fexofenadine, terfenadine, desloratadine, norastemizole, epinastine, ebastine, ebastine, astemizole, levocabastine, azelastine, tranilast, terfenadine, mizolastine, betatastine, CS 560 and HSR 609.

18. The method of claim 16, wherein the prostaglandin inducer is S-5751.

19. The method of claim 5, wherein the immunostimulatory nucleic acid is administered concurrently with the asthma/allergy medicament.

20. The method of claim 1, wherein $X_1X_2$ are GA.

21. The method of claim 20, wherein $X_3X_4$ are TT.

* * * * *

UNITED STATES PATENT AND TRADEMARK OFFICE
CERTIFICATE OF CORRECTION

PATENT NO. : 7,585,847 B2  Page 1 of 1
APPLICATION NO. : 09/776479
DATED : September 8, 2009
INVENTOR(S) : Bratzler et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 309 days Delete the phrase "by 309 days" and insert -- by 647 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,585,847 B2
APPLICATION NO. : 09/776479
DATED : September 8, 2009
INVENTOR(S) : Bratzler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,847 B2 | |
| APPLICATION NO. | : 09/776479 | |
| DATED | : September 8, 2009 | |
| INVENTOR(S) | : Robert L. Bratzler et al. | |

It is certified that error appears in the above-identified patent and that said Letters Patent is hereby corrected as shown below:

This certificate supersedes the Certificate of Correction issued September 14, 2010. The Certificate of Correction is vacated since decision dated April 21, 2010, which corrects the patent term adjustment "by 993 days" was issued in error. The [*] Notice is corrected to reflect the decision dated March 15, 2010, which correctly determined the patent term adjustment --by 647 days--.

On the Title Page:

The first or sole Notice should read

--Subject to any disclaimer, the term of this patent is extended or adjusted under 35 U.S.C. 154(b) by 647 days.--

Signed and Sealed this
Twelfth Day of April, 2011

David J. Kappos
*Director of the United States Patent and Trademark Office*